United States Patent
Brunel et al.

(10) Patent No.: US 10,780,101 B2
(45) Date of Patent: Sep. 22, 2020

(54) AMIDE DERIVATIVES OF SQUALAMINE FOR THE TREATMENT OF INFECTIONS

(71) Applicant: VIRBAC, Carros (FR)

(72) Inventors: Jean-Michel Brunel, Marseilles (FR); Marine Blanchet, Etauliers (FR); Jean-Pascal Marc, Saint Paul de Vence (FR)

(73) Assignee: VIRBAC, Carros (FR)

( * ) Notice: Subject to any disclaimer, the term of this patent is extended or adjusted under 35 U.S.C. 154(b) by 0 days.

(21) Appl. No.: 16/333,484

(22) PCT Filed: Sep. 15, 2017

(86) PCT No.: PCT/EP2017/073267
§ 371 (c)(1),
(2) Date: Mar. 14, 2019

(87) PCT Pub. No.: WO2018/050815
PCT Pub. Date: Mar. 22, 2018

(65) Prior Publication Data
US 2019/0262362 A1 Aug. 29, 2019

(30) Foreign Application Priority Data

Sep. 15, 2016 (FR) ...................... 16 58650

(51) Int. Cl.
| | | |
|---|---|---|
| A61K 31/575 | (2006.01) |
| A61P 31/04 | (2006.01) |
| C07J 9/00 | (2006.01) |
| C07J 41/00 | (2006.01) |

(52) U.S. Cl.
CPC ............... *A61K 31/575* (2013.01); *C07J 9/00* (2013.01); *C07J 41/0005* (2013.01); *C07J 9/005* (2013.01); *C07J 41/0061* (2013.01)

(58) Field of Classification Search
CPC ........... A61K 31/575; C07J 9/00; C07J 41/00; A61P 31/04
See application file for complete search history.

(56) References Cited

U.S. PATENT DOCUMENTS 5,856,535 A 1/1999 Zasloff et al.

FOREIGN PATENT DOCUMENTS

WO 2011067501 A1 6/2011

OTHER PUBLICATIONS

International Search Report (IRS) for PCT/EP2017/073267 dated Oct. 16, 2017 with English Translation (7 pages).
Written Opinoin for PCT/EP2017/073267 dated Oct. 16, 2017 with English Translation (13 pages).
A.M. Bellini et al., "Antimicrobial Activity of Basic Cholane Derivatives Part IX", Arch. Pharm. (Weinheim), vol. 323, 1990, pp. 201-205.
Chen et al. "A Bioconjugate Approach toward Squalamine Mimics: Insight into the Mechansim of Biological Action", Bionjugate Chem. vol. 17, No. 6 (2006), pp. 1582-1591.

*Primary Examiner* — Brenda L Coleman
(74) *Attorney, Agent, or Firm* — Shumaker, Loop & Kendrick, LLP

(57) ABSTRACT

A compound of formula (I)

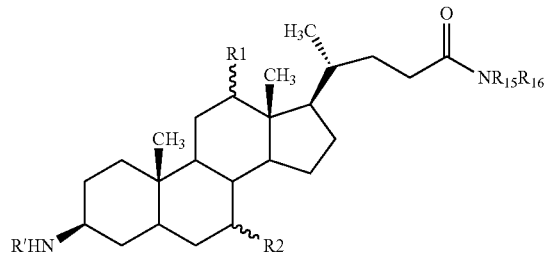

in which R' represents a group $-(CR_aR_b)_n-X-(CR_cR_d)_m-[Y-(CR_eR_f)_o]_t-NR_9R_{10}$ and X and Y independently represent a group $-NR11-$, a group $-O-$ or a divalent 5-membered or 6-membered heterocyclic group comprising at least one nitrogen atom, and also the stereoisomers, mixtures of stereoisomers, and/or pharmaceutically acceptable salts thereof. Also disclosed are pharmaceutical or veterinary compositions containing the compound of formula (I) and also to the use thereof as medicament, more particularly in the treatment of bacterial, fungal, viral or parasitic infections. Also further disclosed are pharmaceutical or veterinary compositions including the compound of formula (I) in combination with an antibiotic other than such a compound of formula (I).

16 Claims, No Drawings

AMIDE DERIVATIVES OF SQUALAMINE FOR THE TREATMENT OF INFECTIONS

TECHNICAL FIELD

The present invention relates to squalamine analogs for their use in the treatment of bacterial, fungal, viral or parasitic infections in man or animals, and also to pharmaceutical or veterinary compositions comprising same.

BACKGROUND

In 1993, squalamine, a natural steroid isolated predominantly from the tissues of a small shark *Squalus acanthias*, proved to be a very active substance essentially having antiangiogenic activity against cells and antiviral and antibacterial activity.

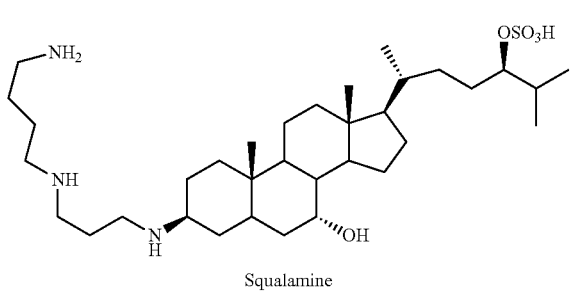

Squalamine

Chemically, squalamine is a novel molecule of amphiphilic nature. It thus includes an apolar central part (a backbone of cholestane type) and two polar ends (a polyamine chain and a sulfate group).

Initially, this water-soluble polyaminosterol raised interest for its antiangiogenic and antimicrobial properties on a variety of Gram-positive bacteria (*Staphylococcus aureus, Enterococcus faecalis*) and Gram-negative bacteria (*Escherichia coli, Pseudomonas aeruginosa*), fungi (*Candida albicans, Candida tropicalis*) and protozoans.

Since the natural source of squalamine is limited, synthetic aminosteroid analog derivatives of squalamine were sought. Derivatives or analogs including a polyamine chain in position 3 or 7 of the 10,13-dimethyl, 17-octane cholestane or cholestene rings, optionally hydroxylated in position 7 or 3, respectively, were especially described. In particular, derivatives of formulae IIa-IIb-IIc-IId and II-1 below were described as having antibacterial activity similar to that of squalamine with respect to various multi-resistant Gram-positive and Gram-negative bacteria.

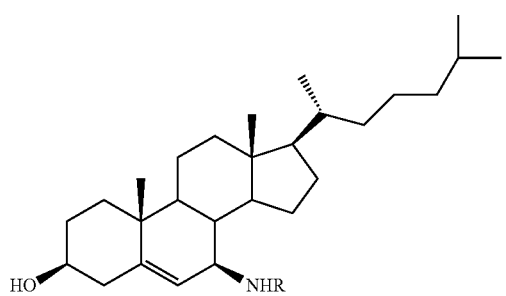

IIa

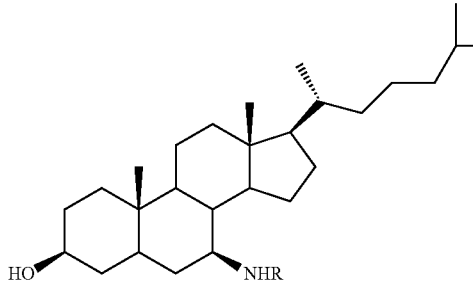

IIb

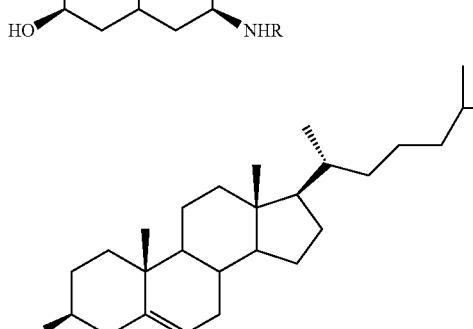

IIc

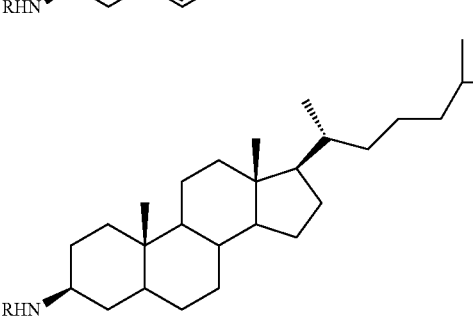

IId

An application of these derivatives for a curative treatment of pulmonary infections via the aerosol route was more particularly suggested. However, the Applicant has observed that these compounds had substantial cytotoxicity and that the compounds of formulae IIc and IId had low activity against certain Gram-negative bacteria such as *E. coli*.

Antibacterial aminosteroid derivatives of polyamino cholestane or cholestene type for local topical application are known in particular from WO 2011/067501, for the rapid cutaneo-mucous decolonization of *Staphylococcus aureus*, especially in ointment or cream form.

U.S. Pat. No. 5,856,535 moreover discloses aminosterol esters, some of which have, inter alia, angiogenesis-inhibiting activity, antiproliferative activity or antibacterial activity. However, none of the compounds described in said document are in particular amides.

The documents Wen-Hua Chen et al. "A bioconjugate approach toward squalamine mimics: insight into the mechanism of the biological action", Bioconjugate Chemistry, vol. 17, No. 6, 1582-1591 and A M Bellini et al. "Antimicrobial activity of basic cholane derivatives part IX", Archiv des Pharmazie, vol. 323, No. 4, 201-205, are also known. However, these documents describe not only compounds that are structurally remote from the compounds of the present invention, but also compounds which do not have advantageous antimicrobial activities.

Squalamine analog compounds which have good antibacterial activity against Gram-positive and Gram-negative bacteria, while at the same time being advantageously less cytotoxic than squalamine, have now been discovered. By virtue of its chemical structure, this novel family of molecules has better chemical stability than the compounds described in U.S. Pat. No. 5,856,535.

SUMMARY

These compounds have advantageous activity for preventing and/or inhibiting and/or treating bacterial, fungal, viral or parasitic infections in man or animals. These compounds are also compounds of choice as antibiotic substitutes. According to a particular embodiment of the invention, it is intended for domestic mammals such as ruminants, horses, pigs, dogs and cats, and wild animals. According to an even more particular embodiment, it is intended for pets, even more precisely for dogs and cats, or for rodents, and is more particularly intended for dogs and cats.

The compounds according to the invention afford excellent activity against bacteria, while at the same time preventing the appearance of resistance, which is a major advantage since the problem of the appearance of resistance to conventional antibiotics has become a public health problem. By virtue of their mechanism of action, which is different from that of antibiotics, the compounds of the invention are thus excellent substitutes for antibiotics.

DETAILED DESCRIPTION

Thus, according to a first aspect, the present invention relates to a compound of formula (I)

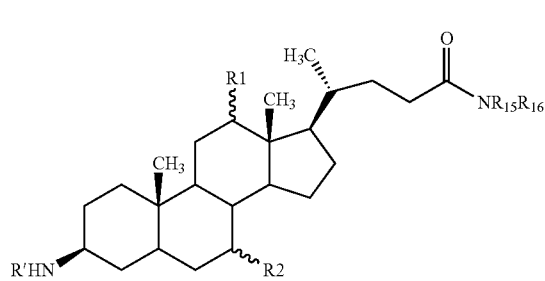

(I)

in which
R1 and R2 independently represent a hydrogen atom, an SO$_3$H group or a hydroxyl group,
R' represents a group —(CR$_a$R$_b$)$_n$—X—(CR$_c$R$_d$)$_m$—[Y—(CR$_e$R$_f$)$_o$]$_t$—NR$_9$R$_{10}$,
R$_a$, R$_b$, R$_c$, R$_d$, R$_e$ and R$_f$ independently represent a hydrogen atom, a (C$_1$-C$_8$)alkyl group or a (C$_6$-C$_{10}$)aryl group,
X and Y independently represent a group —NR11-, a group —O— or a divalent 5-membered or 6-membered heterocyclic group comprising at least one nitrogen atom,
R9 and R10 independently represent a hydrogen atom, a (C$_1$-C$_8$)alkyl group or form, together with the nitrogen atom that bears them, a 5-membered or 6-membered heterocyclic group, optionally substituted with one or two groups =O or =S,
R11 represents a hydrogen atom, a (C$_1$-C$_8$)alkyl group or a —(CH$_2$)$_s$—NH$_2$ group,
R15 and R16 independently represent a hydrogen atom, a (C$_1$-C$_8$)alkyl group or a (C$_6$-C$_{10}$)aryl group, n, m, o and s independently represent an integer between 1 and 5,
t is equal to 0, 1, 2 or 3,
and also the stereoisomers, mixtures of stereoisomers, and/or pharmaceutically acceptable salts thereof.

In the context of the present invention:
The "alkyl" radicals represent straight-chain or branched, saturated hydrocarbon-based radicals, of 1 to 8 carbon atoms, especially of 1 to 6 carbon atoms, preferably of 1 to 4 carbon atoms. Mention may be made especially, when they are linear, of methyl, ethyl, propyl, butyl, pentyl and hexyl radicals. Mention may be made especially, when they are branched, of isopropyl, tert-butyl, 2-methylbutyl, 2-methylpentyl and 1-methylpentyl radicals.

For the purposes of the present patent application, the term "aryl" group means a monocyclic or bicyclic hydrocarbon-based aromatic system of 6 to 10 carbon atoms. Among the aryl radicals, mention may be made especially of the phenyl or naphthyl radical, and even more particularly the phenyl radical.

For the purposes of the present patent application, the term "heterocyclic" group means a monocyclic or bicyclic, saturated, unsaturated or aromatic hydrocarbon-based system comprising one or more heteroatoms such as O, N or S. The heterocyclic groups especially include heteroaryl or heterocycloalkyl groups.

The "heteroaryl" groups denote monocyclic or bicyclic, 5-membered to 7-membered (ring atoms), especially 5-membered to 6-membered, aromatic systems comprising one or more heteroatoms chosen from nitrogen, oxygen and sulfur. Among the heteroaryl radicals, mention may be made of imidazolyl, pyrazinyl, thienyl, oxazolyl, furazanyl and pyrrolyl.

The "heterocycloalkyl" radicals denote 5-membered to 7-membered (ring atoms), especially 5-membered to 6-membered, saturated monocyclic or bicyclic systems comprising one or more heteroatoms chosen from N, O and S. Among the heterocycloalkyls, mention may be made especially of pyrazolidine, piperidine, morpholine and piperazine.

As used herein, the term "pharmaceutically acceptable" refers to compounds, compositions and/or dosage forms which are, within the scope of a valid medical judgement, suitable for use in contact with the cells of humans and lower animals without toxicity, irritation, an undue allergic response and the like, and are proportionate to a reasonable advantage/risk ratio.

The expression "pharmaceutically acceptable salts" refers to the addition salts of pharmaceutically acceptable inorganic and organic acids, and the addition salts of pharmaceutically acceptable bases, of the compounds of the present invention. These salts include acid addition salts, i.e. organic or mineral acid salts of a compound including a basic function such as an amine, or basic addition salts, i.e. alkaline or organic salts of a compound including an acid function such as a carboxylic acid. These salts may be prepared in situ during the final isolation and/or purification of the compounds. In particular, the acid addition salts may be prepared by separately reacting the purified compound with an organic or inorganic acid and isolating the salt thus formed. Among the examples of acid addition salts are hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulfamate, malonate, salicylate, propionate, methylenebis-b-hydroxynaphthoate, gentisic acid, isethionate, di-p-toluoyltartrate, methanesulfonate, ethanesulfonate, benzenesulfonate, p-toluenesulfonate, cyclohexyl sulfamates and quinatelauryl sulfonate salts, and similar salts. (See, for example, S. M. Berge et al. "Pharmaceutical Salts", J. Pharm. Sci, 66, pages 1-19 (1977)).

The basic addition salts may also be prepared by separately reacting the purified compound in its acid form with an organic or inorganic base and isolating the salt thus formed. Examples of basic addition salts comprise the sodium, potassium, calcium, barium, zinc, magnesium and aluminum salts. The sodium and potassium salts are preferred. The basic addition salts may especially be prepared from alkali metal or alkaline-earth metal hydrides or hydroxides which comprise sodium hydride, sodium hydroxide, potassium hydroxide, calcium hydroxide, aluminum hydroxide, lithium hydroxide, magnesium hydroxide and zinc hydroxide.

Among the compounds of general formula (I), a first subgroup of compounds is formed from compounds for which R1 and R2 independently represent a hydrogen atom or a hydroxyl group.

Among the compounds of general formula (I), a second subgroup of compounds is formed from compounds for which R15 and R16 independently represent a hydrogen atom or a $(C_1-C_4)$alkyl group.

Among the compounds of general formula (I), a third subgroup of compounds is formed from compounds for which X is an —NH— group or a 1,4-piperidyl group.

Among the compounds of general formula (I), a fourth subgroup of compounds is formed from compounds for which R9 and R10 represent a hydrogen atom.

Among the compounds of general formula (I), a fifth subgroup of compounds is formed from compounds for which $R_a$, $R_b$, $R_c$, $R_d$, $R_e$ and $R_f$ represent a hydrogen atom.

Among the compounds of general formula (I), a sixth subgroup of compounds is formed from compounds for which Y is a group —NR11-, with R11 representing a hydrogen atom, a $(C_1-C_4)$alkyl group or a —$(CH_2)_s$—$NH_2$ group in which s is equal to 1, 2 or 3.

Among the compounds of general formula (I), a seventh subgroup of compounds is formed from compounds for which m is equal to 2, 3, 4 or 5, more preferentially 2 or 3.

Among the compounds of general formula (I), an eighth subgroup of compounds is formed from compounds for which n is equal to 2, 3, 4 or 5, more preferentially 2, 3 or 4 and even more preferentially 2 or 3.

Among the compounds of general formula (I), a ninth subgroup of compounds is formed from compounds for which m is other than 4.

Among the compounds of general formula (I), a tenth subgroup of compounds is formed from compounds for which o is equal to 2 or 3.

Among the compounds of general formula (I), an eleventh subgroup of compounds is formed from compounds for which the group —NHR' is chosen from:

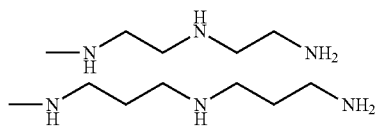

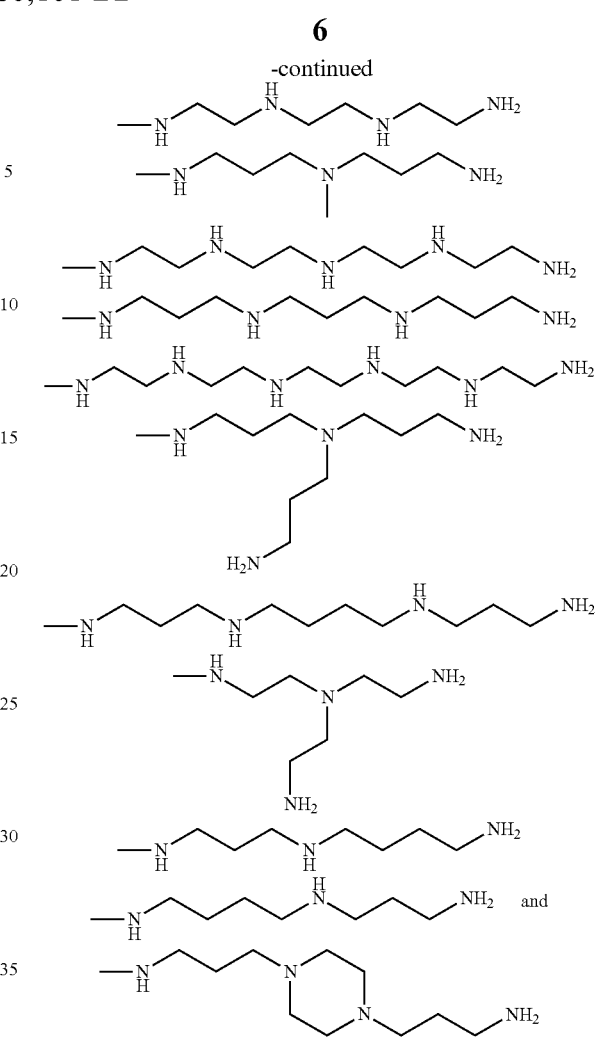

According to a preferred variant, the compounds of formula (I) are synthesized from the following bile acids:

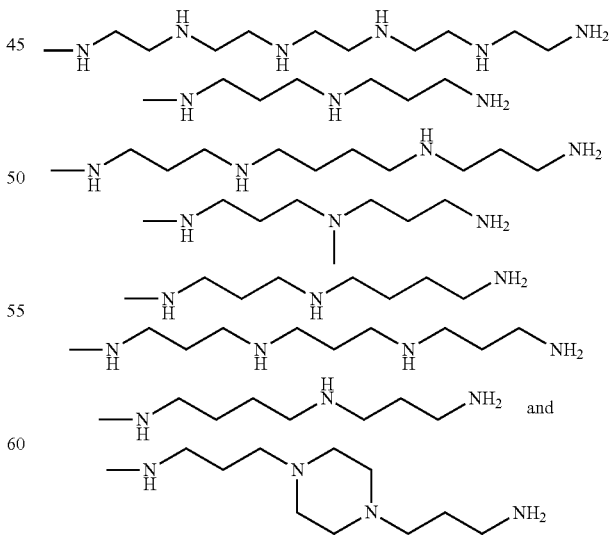

The subgroups defined above, taken separately or in combination, also form part of the invention.

Consequently, the present invention relates to a compound as defined previously, characterized in that it is defined by at least one of the following subgroups:
first subgroup of compounds of formula (I) for which R1 and R2 independently represent a hydrogen atom or a hydroxyl group,
second subgroup of compounds of formula (I) for which R15 and R16 independently represent a hydrogen atom or a $(C_1$-$C_4)$alkyl group,
third subgroup of compounds of formula (I) for which X is an —NH— group, a 6-membered heterocyclic group including one or two nitrogen atoms, preferably a 1,4-piperazinylene group or a 1,4-piperidinylene group,
fourth subgroup of compounds of formula (I) for which R9 and R10 represent a hydrogen atom,
fifth subgroup of compounds of formula (I) for which $R_a$, $R_b$, $R_c$, $R_d$, $R_e$ and $R_f$ represent a hydrogen atom,
sixth subgroup of compounds of formula (I) for which Y is a group —NR11-, with R11 representing a hydrogen atom, a $(C_1$-$C_4)$alkyl group or a —$(CH_2)_s$—$NH_2$ group in which s is equal to 1, 2 or 3,
seventh subgroup of compounds of formula (I) for which m is equal to 2, 3, 4 or 5, more preferentially 2 or 3,
eighth subgroup of compounds of formula (I) for which n is equal to 2, 3, 4 or 5, more preferentially 2, 3 or 4,
ninth subgroup of compounds of formula (I) for which m is other than 4,
tenth subgroup of compounds of formula (I) for which o is equal to 2 or 3,
eleventh subgroup of compounds of formula (I) for which the group —NHR' is chosen from:

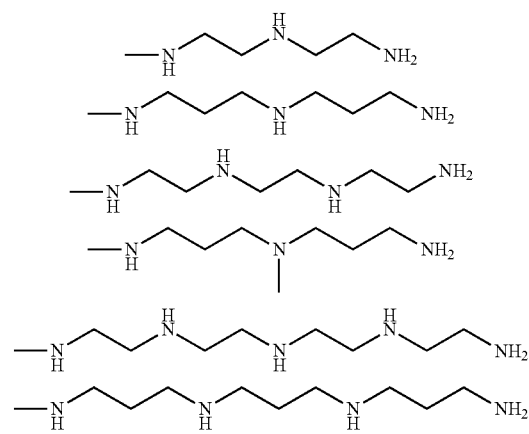

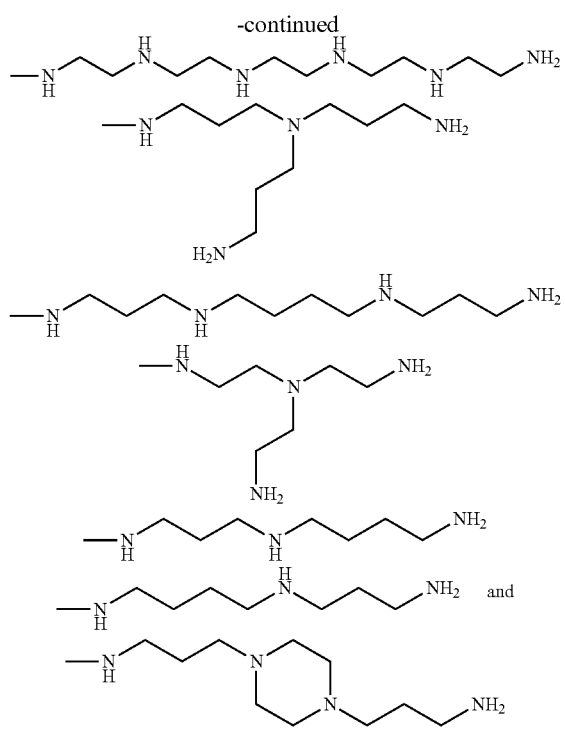

or by the combination of the subgroups as defined above.

According to a particular embodiment, the present invention relates to a compound as defined previously, characterized in that it represents formula (I')

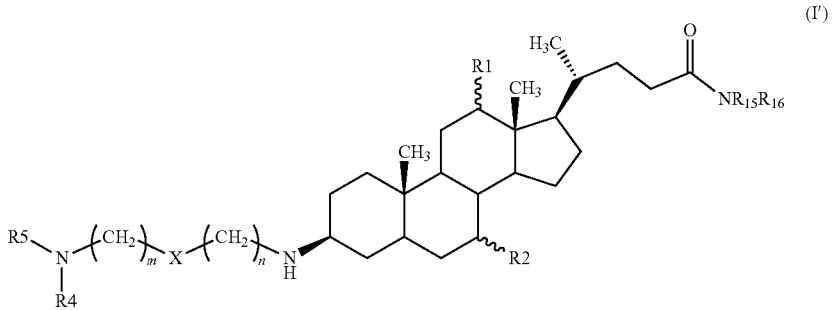

in which
R1 and R2 are as defined in claim 1 or 2,
R15 and R16 independently represent a hydrogen atom or a $(C_1$-$C_8)$alkyl group,
n represents the integer 2, 3 or 4,
m represents the integer 2, 3 or 4,
X represents a group —NR11- or a divalent 5-membered or 6-membered heterocyclic group comprising one or two nitrogen atoms, such as a 1,4-piperazinylene group or a 1,4-piperidinylene group,
R4 and R11 independently represent a hydrogen atom, a $(C_1$-$C_8)$alkyl group or a —$(CH_2)_s$—$NH_2$ group,
R5 represents a hydrogen atom, a —$(CH_2)_p$—$NH_2$ group, a —$(CH_2)_p$—NH—$(CH_2)_q$—$NH_2$ group or a —$(CH_2)_p$—NH—$(CH_2)_q$—NH—$(CH_2)_r$—$NH_2$ group,
p, q, r and s independently represent an integer which may range between 1 and 5,
and also the stereoisomers, mixtures of stereoisomers, and/or pharmaceutically acceptable salts thereof.

Among the compounds of formulae (I) and (I'), preference is given to the compounds for which n and m are equal to 3.

According to a particular embodiment, the present invention relates to a compound as defined previously, characterized in that R15 and R16 independently represent a hydrogen atom or a ($C_1$-$C_4$)alkyl group such as a methyl or an isopropyl.

According to a particular embodiment, the present invention relates to a compound as defined previously, characterized in that n is equal to 2 and m is equal to 3, n is equal to 2 and m is equal to 2, n is equal to 3 and m is equal to 4 or n is equal to 3 and m is equal to 3.

According to a particular embodiment, the present invention relates to a compound as defined previously, characterized in that X represents a group —NR11- or a 1,4-piperazinylene group and R4 and R11 independently represent a hydrogen atom, a methyl group or a —$(CH_2)_s$—$NH_2$ group, in which s is equal to 2 or 3.

According to a particular embodiment, the present invention relates to a compound as defined previously, characterized in that R5 represents a hydrogen atom, a —$(CH_2)_p$—$NH_2$ group, a —$(CH_2)_p$—NH—$(CH_2)_q$—$NH_2$ group or a —$(CH_2)_p$—NH—$(CH_2)_q$—NH—$(CH_2)_r$—$NH_2$ group, in which p is equal to 2 or 3, q is equal to 2 and r is equal to 2.

According to a particular embodiment, n is equal to m.

The present invention also relates to a compound of formula (Ia)

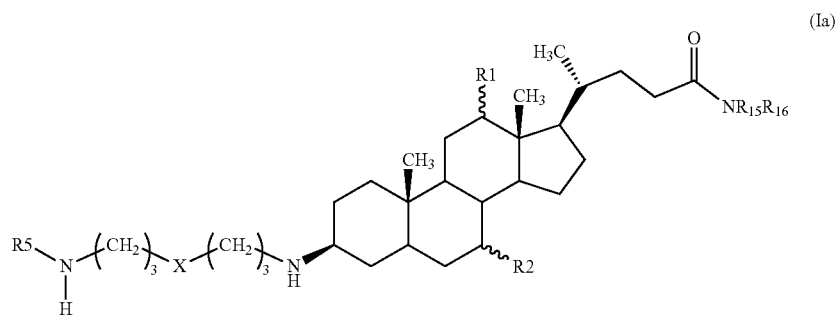

in which
R15, R16, R1 and R2 are as defined previously,
X represents an —NH— group or a 1,4-piperazinylene group,
R5 represents a hydrogen atom or a —$(CH_2)_p$—$NH_2$ group, in which p is equal to 2 or 3,
and also the stereoisomers, mixtures of stereoisomers, and/or pharmaceutically acceptable salts thereof.

According to a preferred embodiment, the present invention relates to the compounds of formula (Ia) for which R15 is a hydrogen atom and R16 is a methyl or isopropyl group or alternatively R15 and R16 are both an ethyl group.

The present invention also relates to a compound of formula (Ib)

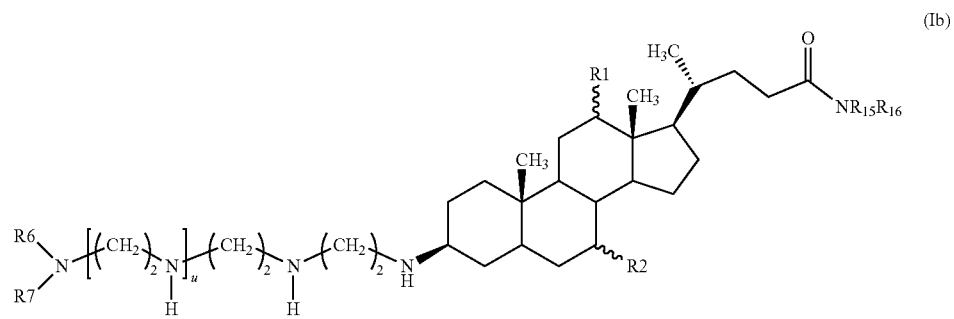

in which
R15, R16, R1 and R2 are as defined previously,
u is equal to 0, 1, 2 or 3, preferentially equal to 1, 2 or 3,
R6 and R7 independently represent a hydrogen atom or a ($C_1$-$C_8$)alkyl group, preferably a hydrogen atom or a ($C_1$-$C_4$)alkyl group,
and also the stereoisomers, mixtures of stereoisomers, and/or pharmaceutically acceptable salts thereof.

The present invention also relates to a compound of formula (Ic)

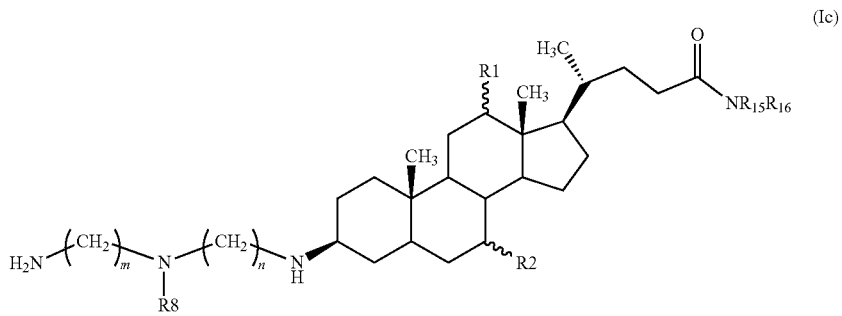

(Ic)

in which
R15, R16, R1, R2, n and m are as defined previously, and R8 represents a (C₁-C₈)alkyl group, preferably a methyl group, or a —(CH₂)$_s$—NH₂ group, with s being an integer which may range between 1 and 5, preferably equal to 2 or 3,
and also the stereoisomers, mixtures of stereoisomers, and/or pharmaceutically acceptable salts thereof.

According to a preferred embodiment, the present invention relates to the compounds of formula (Ic) for which, when R8 represents a —(CH₂)$_s$NH₂ group, then n=m=s.

According to a preferred embodiment, the present invention relates to the compounds of formula (Ic) for which, when R8 represents a methyl group, then n is equal to m.

The present invention also relates to a compound of formula (Id)

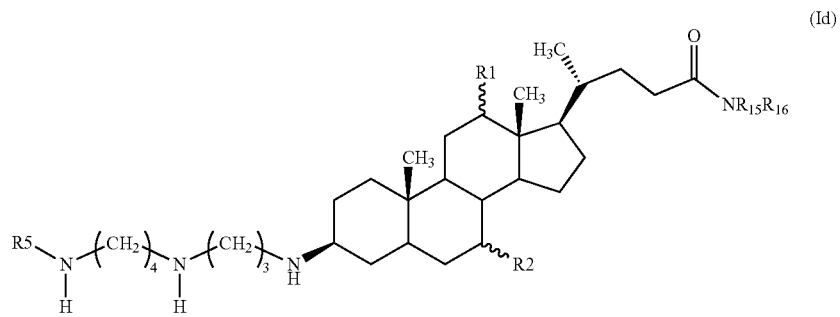

(Id)

in which
R15, R16, R1 and R2 are as defined previously,
R5 represents a —(CH₂)$_p$—NH₂ group, in which p is equal to 2 or 3,
and also the stereoisomers, mixtures of stereoisomers, and/or pharmaceutically acceptable salts thereof.

The present invention also relates to a compound of formula (Ie)

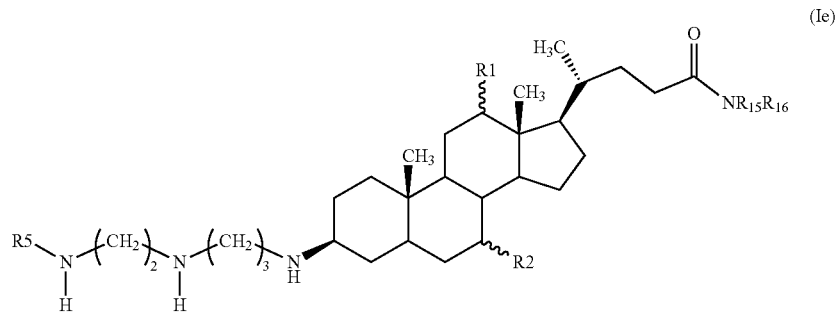

(Ie)

in which

R15, R16, R1 and R2 are as defined previously,

R5 represents a —$(CH_2)_p$—$NH_2$ group, in which p is equal to 2 or 3, and also the stereoisomers, mixtures of stereoisomers, and/or pharmaceutically acceptable salts thereof.

According to a particularly preferred embodiment, the present invention relates to a compound of formula (Ia) and of formula (Ic) as defined above. As compounds representing this particular embodiment, mention may be made in particular of compounds (5) and (15) as defined below.

According to a preferred embodiment of the present invention, a compound of formula (I) is chosen from:

(1) 3β-norspermino-N-isopropyldeoxycholamide,
(2) 3β-norspermidino-N-isopropyldeoxycholamide,
(3) 3β-(1,4-bis(3-aminopropyl)piperazine)-N-isopropyldeoxycholamide,
(4) 3β-norspermino-N-isopropylcholamide,
(5) 3β-norspermidino-N-isopropylcholamide,
(6) 3β-(1,4-bis(3-aminopropyl)piperazine)-N-isopropyldeoxycholamide,
(7) 3β-norspermino-N-isopropylchenodeoxycholamide,
(8) 3β-norspermidino-N-isopropylchenodeoxycholamide,
(9) 3β-(1,4-bis(3-aminopropyl)piperazine)-N-isopropylchenodeoxycholamide,
(10) 3β-norspermino-N-methylchenodeoxycholamide,
(11) 3β-norspermidino-N-methylchenodeoxycholamide,
(12) 3β-(1,4-bis(3-aminopropyl)piperazine)-N-methylchenodeoxycholamide,
(13) 3β-norspermidino-N,N-diethylchenodeoxycholamide,
(14) 3β-norspermino-N-isopropylursodeoxycholamide,
(15) 3β-norspermidino-N-isopropylursodeoxycholamide,
(16) 3β-(1,4-bis(3-aminopropyl)piperazine)-N-isopropylursodeoxycholamide,
(17) 3β-norspermino-N-isopropyllithocholamide,
(18) 3β-norspermidino-N-isopropyllithocholamide,
(19) 3β-(1,4-bis(3-aminopropyl)piperazine)-N-isopropyllithocholamide,
(20) 3β-(pentaethylenehexamine)-N-isopropyldeoxycholamide,
(21) 3β-(pentaethylenehexamine)-N-isopropylcholamide,
(22) 3β-(pentaethylenehexamine)-N-isopropylchenodeoxycholamide,
(23) 3β-(pentaethylenehexamine)-N-isopropylursodeoxycholamide,
(24) N-isopropyl-3β-pentaethylenehexaminedeoxycholamide,
(25) 3β-(1,4-bis(3-aminopropyl)piperazine)-N-isopropyldeoxycholamide,
(26) 3β-(bis(3-aminopropyl)methylamine)-N-isopropylcholamide,
(27) 3β-(bis(3-aminopropyl)methylamine)-N-isopropylchenodeoxycholamide,
(28) 3β-(bis(3-aminopropyl)methylamine)-N-isopropylursodeoxycholamide,
(29) 3β-(bis(3-aminopropyl)methylamine)-N-isopropyllithocholamide,
(30) 3β-spermino-N-isopropyldeoxycholamide,
(31) 3β-spermino-N-isopropylcholamide,
(32) 3β-spermino-N-isopropylchenodeoxycholamide,
(33) 3β-spermino-N-methyldeoxycholamide,
(34) 3β-spermino-N,N-diethylchenodeoxycholamide,
(35) 3β-spermino-N-isopropylursodeoxycholamide,
(36) 3β-spermino-N-isopropyllithocholamide,
(37) 3β-norspermidino-N-diisopropylchenodeoxycholamide,
(38) 3β-norspermidino-N-cyclohexylchenodeoxycholamide,
(39) 3β-norspermino-N,N-diethylchenodeoxycholamide,
(40) 3β-norspermino-N,N-diisopropylchenodeoxycholamide,
(42) 3β-(tris(3-aminopropyl)amine)-N-isopropyldeoxycholamide,
(43) 3β-(tris(3-aminopropyl)amine)-N-isopropylcholamide,
(44) 3β-(tris(3-aminopropyl)amine)-N,N-diethylchenodeoxycholamide,
(45) 3β-(tris(2-aminoethyl)amine)-N-isopropylchenodeoxycholamide,
(46) 3β-(tris(3-aminopropyl)amine)-N-isopropylchenodeoxycholamide,
(47) 3β-(tris(3-aminopropyl)amine)-N-cyclohexylchenodeoxycholamide,
(48) 3β-(tris(3-aminopropyl)amine)-N-isopropylursodeoxycholamide,
(49) 3β-(tris(3-aminopropyl)amine)-N-isopropyllithocholamide,
(50) 3β-spermino-N,N-diisopropylchenodeoxycholamide,
(51) 3β-spermino-N-cyclohexylchenodeoxycholamide,
(52) 3β-spermidino-N-isopropylchenodeoxycholamide,
(53) 3β-(bis(3-aminopropyl)ethylenediamine)-N,N-diethylchenodeoxycholamide,
(54) 3β-(bis(3-aminopropyl)ethylenediamine)-N,N-diisopropylchenodeoxycholamide,
(55) 50/50 mixture of 3β-spermidino-N-isopropylchenodeoxycholamide and of 3β-N-[4'N-(3'-aminopropyl)aminobutyl]amino-N-isopropylchenodeoxycholamide,
(56) 3β-(tris(3-aminopropyl)amine)-N,N-diisopropylchenodeoxycholamide, or a pharmaceutically acceptable salt thereof.

The compounds of the invention may exist in the form of free bases or of addition salts with pharmaceutically acceptable acids.

According to a particular embodiment of the invention, such addition salts of pharmaceutically acceptable acids comprise the hydrobromide, tartrate, citrate, trifluoroacetate, ascorbate, hydrochloride, triflate, maleate, mesylate, formate, acetate and fumarate, and more particularly the hydrochloride.

The compounds of formulae (I), (I'), (Ia), (Ib), (Ic), (Id) and (Ie) and also compounds (1) to (56) may be in the form of solvates such as hydrates. The invention comprises these solvates.

A compound of formula (I), (I'), (Ia), (Ib), (Ic), (Id) or (Ie) may comprise one or more asymmetric carbon atoms. They may thus exist in the form of enantiomers or diastereoisomers. These enantiomers and diastereoisomers, and also mixtures thereof, including racemic mixtures, are included in the scope of the present invention. In general, in the context of the present invention, when a bond is represented by the symbol ⁓, this means that the group borne by the carbon under consideration may be behind or in front of the plane of representation of the molecule. Thus, the stereochemistry resulting from the carbon bearing this group may be S or R.

According to another aspect, the present invention relates to a compound of formula (I), (I'), (Ia), (Ib), (Ic), (Id) or (Ie) or a compound (1) to (56) or a pharmaceutically acceptable salt thereof, for its use as a medicament.

According to another aspect, the present invention relates to a compound of formula (I), (I'), (Ia), (Ib), (Ic), (Id) or (Ie) for its use for preventing and/or inhibiting and/or treating bacterial, fungal, viral or parasitic infections in man or animals.

According to the present invention, the term "preventing" or "prevention" means reducing the risk of appearance or slowing down the appearance of a given phenomenon, namely a bacterial, fungal, viral or parasitic infection.

The compounds of the present invention may be prepared via conventional processes of organic synthesis performed by a person skilled in the art. The general reaction scheme described below represents a general method that is useful for preparing the compounds of the present invention and is not intended to limit the scope or usefulness thereof.

Thus, the compounds of the invention may be prepared by application or adaptation of any method known per se and/or within the scope of a person skilled in the art, especially those described by Larock in Comprehensive Organic Transformations, VCH Pub., 1989, or by application or adaptation of the processes described in the examples that follow.

According to a particular embodiment, the compounds of the invention may be prepared according to the synthetic scheme 1 below.

for example at a temperature of between 20° C. and 100° C., to obtain a compound of formula (II).

Still according to this scheme 1, the compound of formula (II) thus obtained is subjected to a reductive amination by reaction with a compound of formula R'NH$_2$, in which R' is as defined previously, in the presence of a reducing agent such as titanium tetraisopropoxide, zirconium tetraisopropoxide, NaBH$_3$CN, NaBH$_4$ or a mixture thereof, preferentially the titanium tetraisopropoxide/NaBH$_4$ couple, for example at a temperature of between −120° C. and −10° C., preferentially −80° C. and −10° C., to obtain the compound of formula (I).

Optionally, said process may also comprise the step consisting in isolating the product obtained.

The compound thus prepared may be recovered from the reaction mixture via the conventional means. For example, the compounds may be recovered by distilling the solvent from the reaction mixture or, if necessary, after distillation of the solvent from the solution mixture, pouring the residue

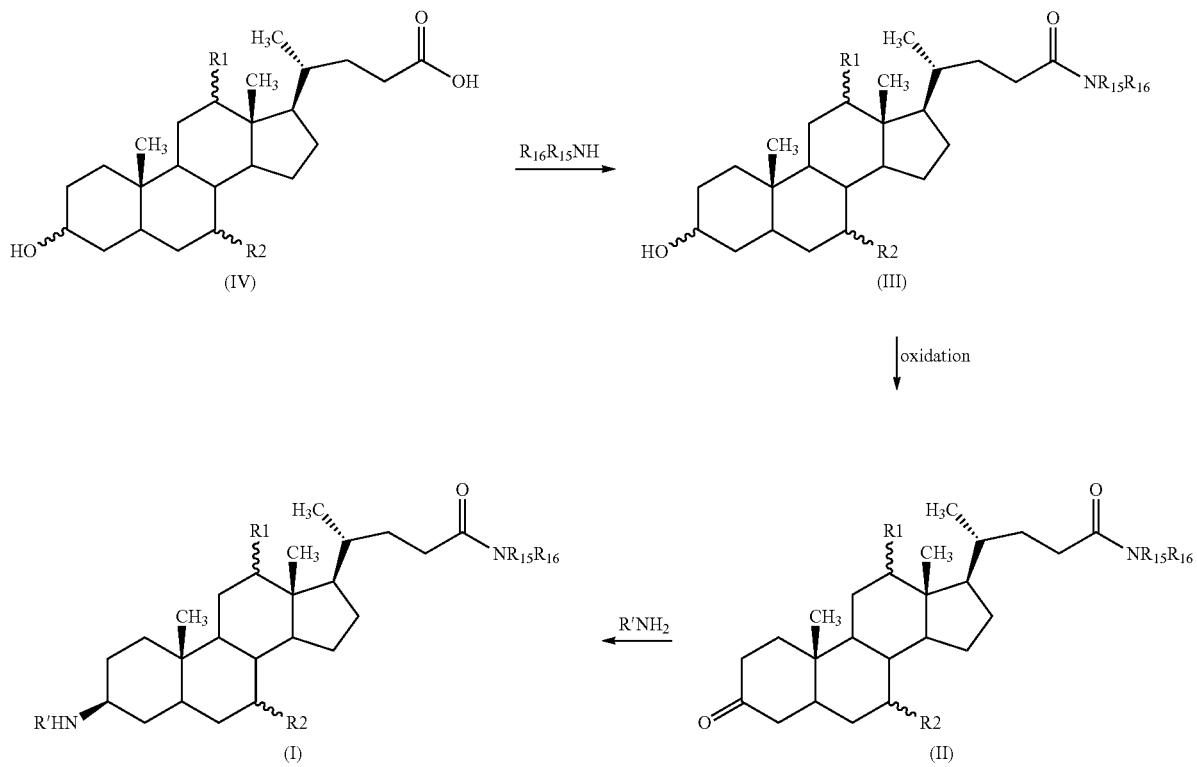

Scheme 1

According to this scheme 1, a compound of formula (IV), in which R1 and R2 are as defined previously, is reacted, in a solvent such as CH$_2$Cl$_2$, THF or dioxane, for example in the presence of a coupling agent such as HOBT/DCC, BOP or methyl chloroformate, with a compound of formula R15R16NH, in which R15 and R16 are as defined previously, for example at a temperature of between −20° C. and 20° C., to obtain a compound of formula (III).

Still according to this scheme 1, the compound of formula (III) thus obtained is subjected to oxidation in the presence of a ligand, for example aluminum tri-tert-butoxide, aluminum triisopropoxide or Ag$_2$CO$_3$, in a solvent such as, for example, benzene, toluene, cyclohexane or trifluorotoluene, into water, followed by extraction with a water-immiscible organic solvent, and distilling the solvent from the extract. In addition, the product may, if so desired, be further purified via various techniques, such as recrystallization, reprecipitation or various chromatography techniques, especially column chromatography or preparative thin-layer chromatography.

The starting compound of formula (IV) is available or may be prepared according to the methods known to those skilled in the art and/or may be prepared by applying the processes as described in the Examples or obvious chemical equivalents thereof.

According to a preferred variant, the compounds of formula (I) are synthesized from the compounds of formula (IV) as defined above or from the following bile acids:

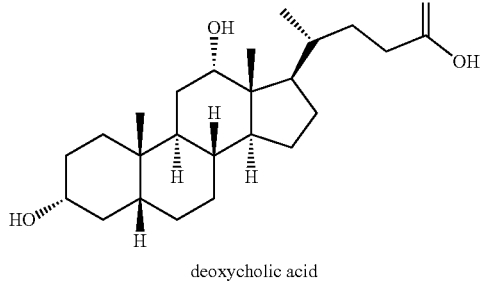

deoxycholic acid

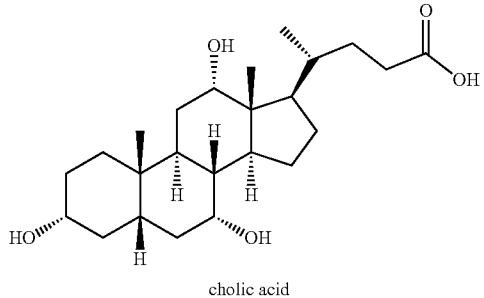

cholic acid

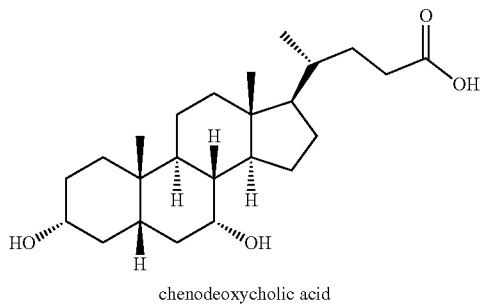

chenodeoxycholic acid

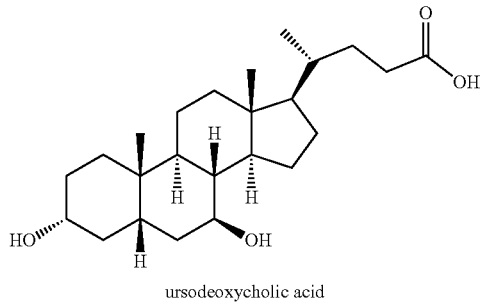

ursodeoxycholic acid

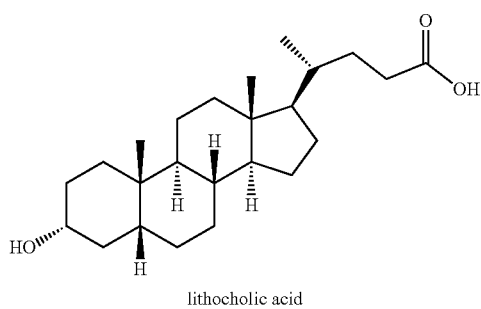

lithocholic acid

Thus, according to another subject, the present invention also relates to the process for preparing the compounds of formula (I) described previously, comprising a step of reductive amination of the compound of formula (II)

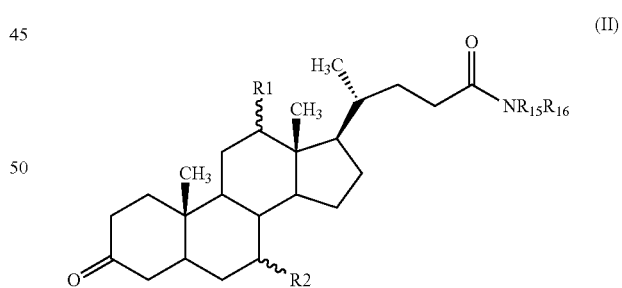

(II)

in which R15, R16, R1 and R2 are as defined previously, with an amine of formula R'NH2 in which R' is as defined previously, in the presence of a reducing agent which may be chosen from titanium tetraisopropoxide, zirconium tetraisopropoxide, NaBH$_3$CN, NaBH$_4$ or a mixture thereof, preferentially the titanium tetraisopropoxide/NaBH$_4$ couple, to obtain said compound of formula (I).

The chemical structures and the spectroscopic data of a few compounds of formula (I) of the invention are illustrated, respectively, in table I and table II below.

TABLE 1
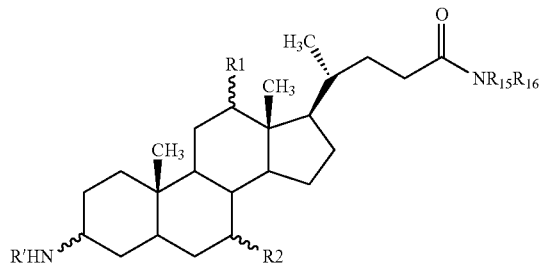
(I)
Formula (Ia)
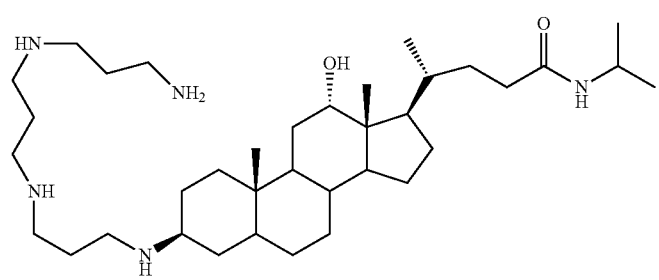 [SMILES: CC(C)NC(=O)CC[C@@H](C)[C@H]1CCC2C3CCC4C[C@@H](NCCCNCCCNCCCN)CC[C@]4(C)C3C[C@H](O)[C@@]21C]
1
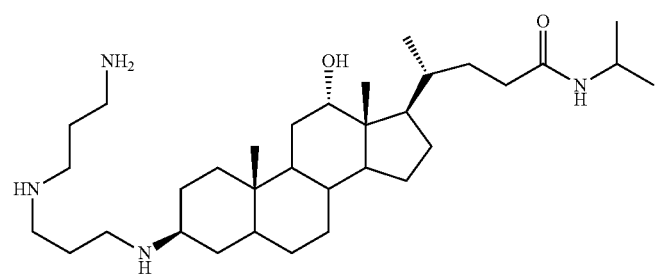 [SMILES: CC(C)NC(=O)CC[C@@H](C)[C@H]1CCC2C3CCC4C[C@@H](NCCCNCCCN)CC[C@]4(C)C3C[C@H](O)[C@@]21C]
2
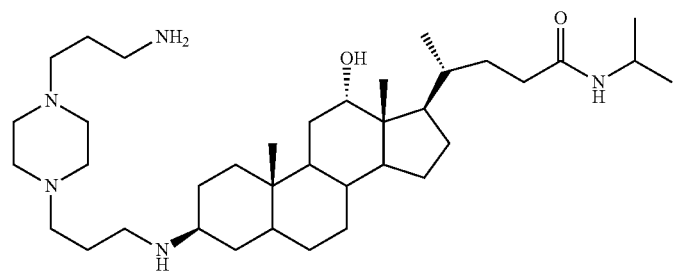 [SMILES: CC(C)NC(=O)CC[C@@H](C)[C@H]1CCC2C3CCC4C[C@@H](NCCCN5CCN(CCCN)CC5)CC[C@]4(C)C3C[C@H](O)[C@@]21C]
3
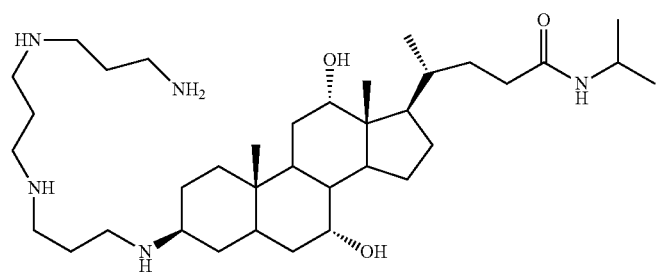 [SMILES: CC(C)NC(=O)CC[C@@H](C)[C@H]1CCC2C3C(C[C@H](O)[C@@]21C)[C@@]1(C)CC[C@H](NCCCNCCCNCCCN)CC1C[C@H]3O]
4

TABLE 1-continued
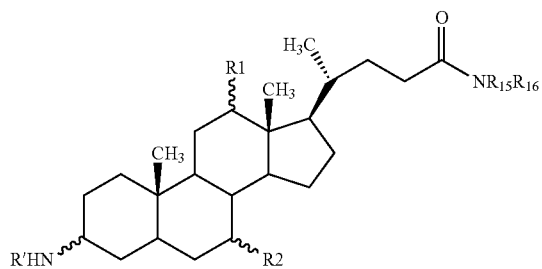
(I)
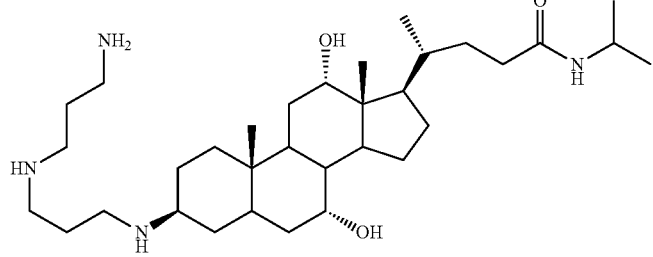
5
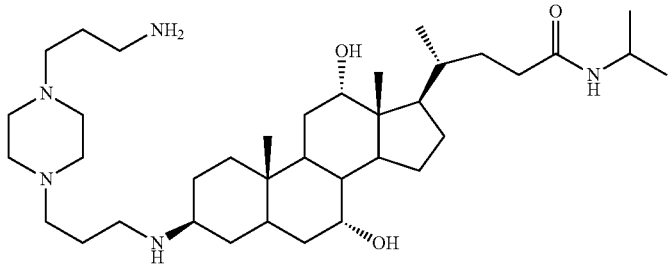 [SMILES: CC(C)NC(=O)CC[C@@H](C)[C@H]1CCC2C3C(C[C@H](O)[C@@]21C)[C@@]1(C)CC[C@H](NCCCN2CCN(CCCN)CC2)CC1C[C@H]3O]
6
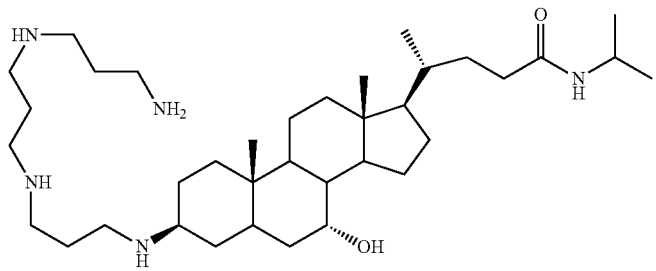 [SMILES: CC(C)NC(=O)CC[C@@H](C)[C@H]1CCC2C3C(CC[C@@]21C)[C@@]1(C)CC[C@H](NCCCNCCCNCCCN)CC1C[C@H]3O]
7
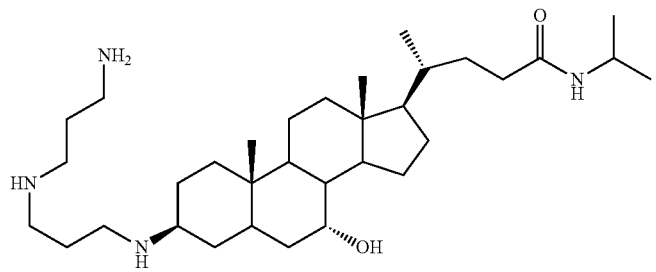 [SMILES: CC(C)NC(=O)CC[C@@H](C)[C@H]1CCC2C3C(CC[C@@]21C)[C@@]1(C)CC[C@H](NCCCNCCCN)CC1C[C@H]3O]
8

TABLE 1-continued
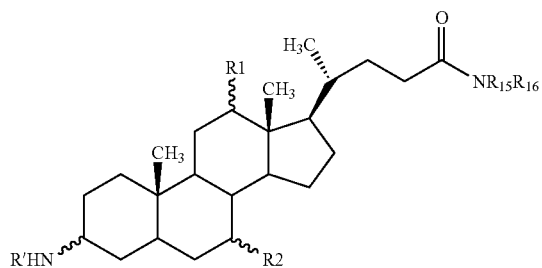
(I)
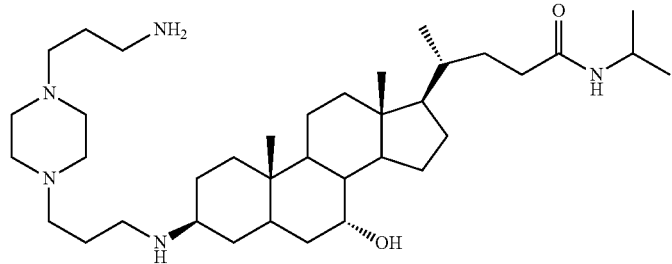 [SMILES: CC(C)NC(=O)CC[C@@H](C)[C@H]1CCC2C3C(CC[C@@]21C)[C@@]1(C)CC[C@H](NCCCN2CCN(CCCN)CC2)CC1C[C@H]3O]
9
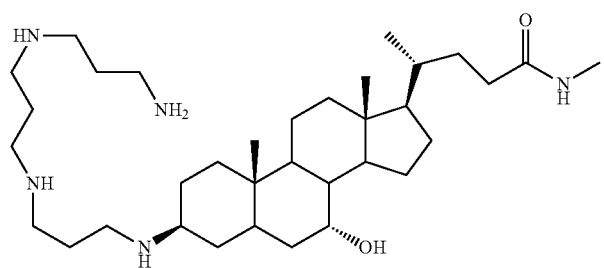 [SMILES: CNC(=O)CC[C@@H](C)[C@H]1CCC2C3C(CC[C@@]21C)[C@@]1(C)CC[C@H](NCCCNCCCNCCCN)CC1C[C@H]3O]
10
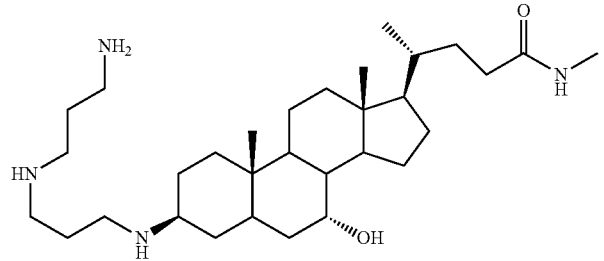 [SMILES: CNC(=O)CC[C@@H](C)[C@H]1CCC2C3C(CC[C@@]21C)[C@@]1(C)CC[C@H](NCCCNCCCN)CC1C[C@H]3O]
11
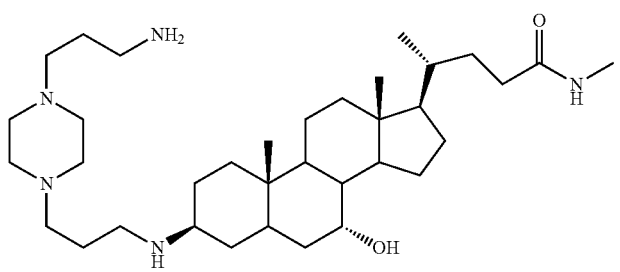 [SMILES: CNC(=O)CC[C@@H](C)[C@H]1CCC2C3C(CC[C@@]21C)[C@@]1(C)CC[C@H](NCCCN2CCN(CCCN)CC2)CC1C[C@H]3O]
12

TABLE 1-continued
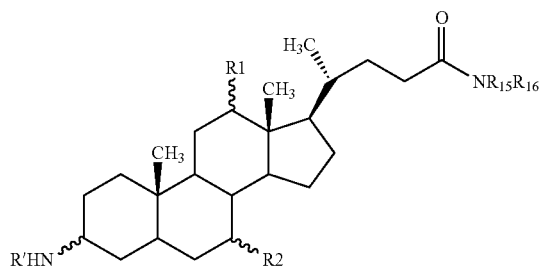
(I)
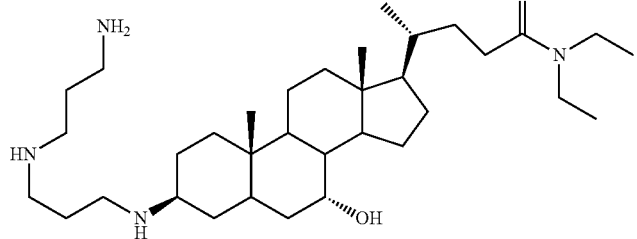
13
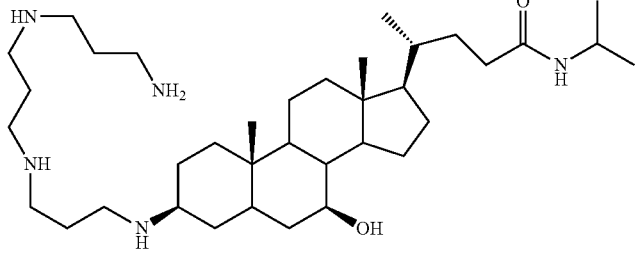
14
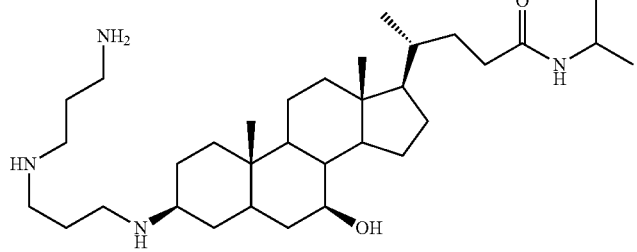
15
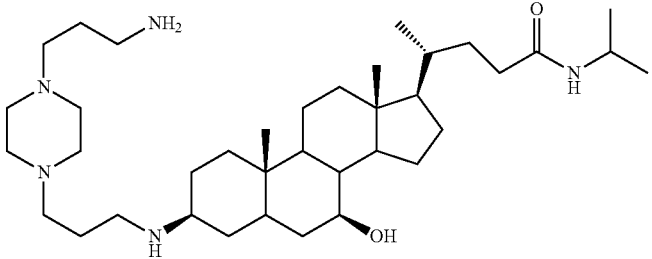 [SMILES: CC(C)NC(=O)CC[C@@H](C)[C@H]1CCC2C3C(CC[C@@]21C)[C@@]1(C)CC[C@H](NCCCN2CCN(CCCN)CC2)CC1C[C@@H]3O]
16

TABLE 1-continued
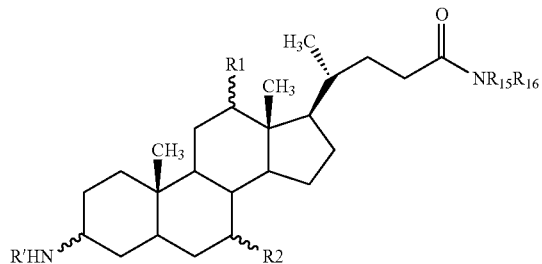
(I)
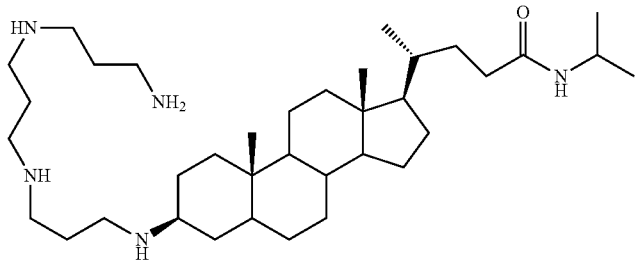 [SMILES: CC(C)NC(=O)CC[C@@H](C)[C@H]1CCC2C3CCC4C[C@@H](NCCCNCCCNCCCN)CC[C@]4(C)C3CC[C@@]21C]
17
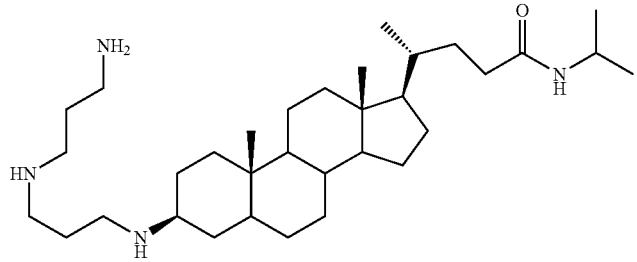 [SMILES: CC(C)NC(=O)CC[C@@H](C)[C@H]1CCC2C3CCC4C[C@@H](NCCCNCCCN)CC[C@]4(C)C3CC[C@@]21C]
18
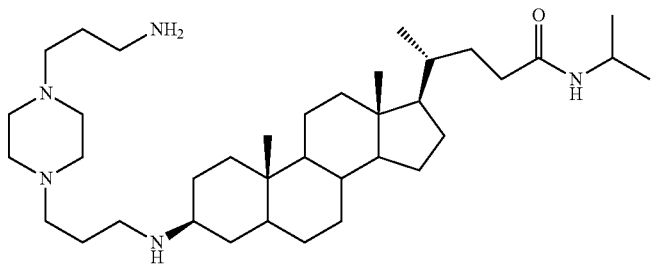 [SMILES: CC(C)NC(=O)CC[C@@H](C)[C@H]1CCC2C3CCC4C[C@@H](NCCCN5CCN(CCCN)CC5)CC[C@]4(C)C3CC[C@@]21C]
19
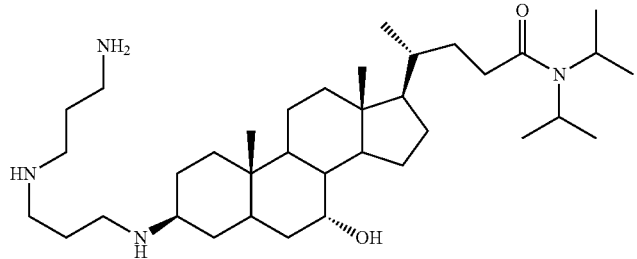 [SMILES: CC(C)N(C(=O)CC[C@@H](C)[C@H]1CCC2C3C(CC[C@@]21C)[C@@]1(C)CC[C@H](NCCCNCCCN)CC1C[C@H]3O)C(C)C]
37

TABLE 1-continued
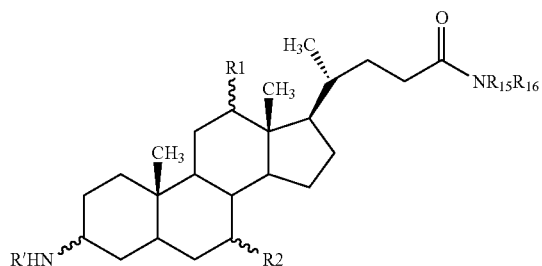
(I)
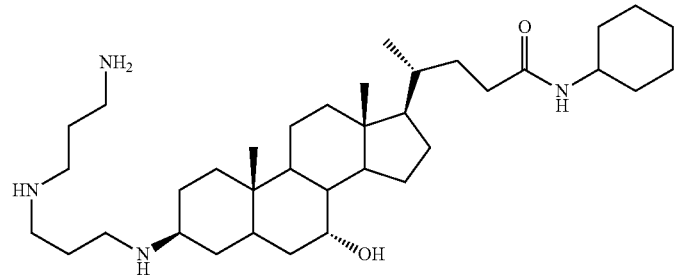 [SMILES: C[C@H](CCC(=O)NC1CCCCC1)[C@H]1CCC2C3C(CC[C@@]21C)[C@@]1(C)CC[C@H](NCCCNCCCN)CC1C[C@H]3O]
38
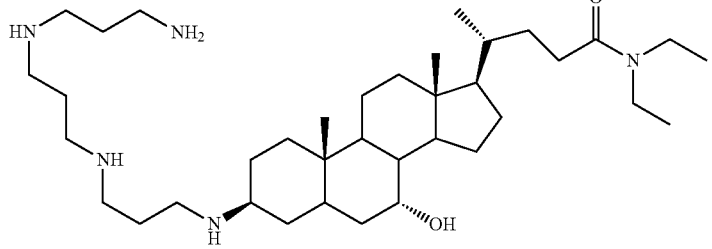
39
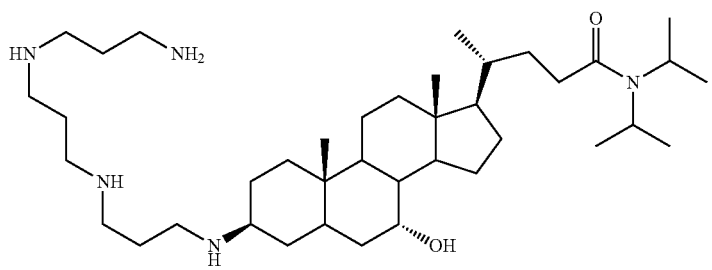 [SMILES: CC(C)N(C(=O)CC[C@@H](C)[C@H]1CCC2C3C(CC[C@@]21C)[C@@]1(C)CC[C@H](NCCCNCCCNCCCN)CC1C[C@H]3O)C(C)C]
40
Formula (Ib)
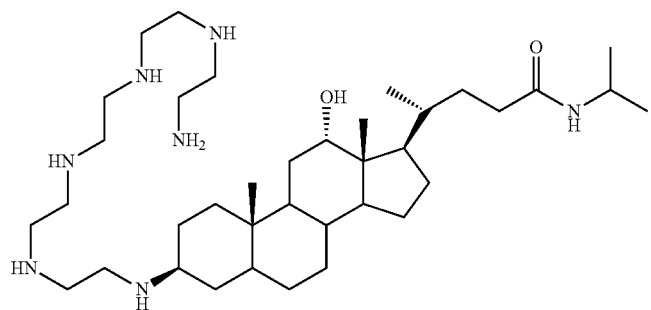 [SMILES: CC(C)NC(=O)CC[C@@H](C)[C@H]1CCC2C3CCC4C[C@@H](NCCNCCNCCNCCNCCN)CC[C@]4(C)C3C[C@H](O)[C@@]21C]
20

TABLE 1-continued
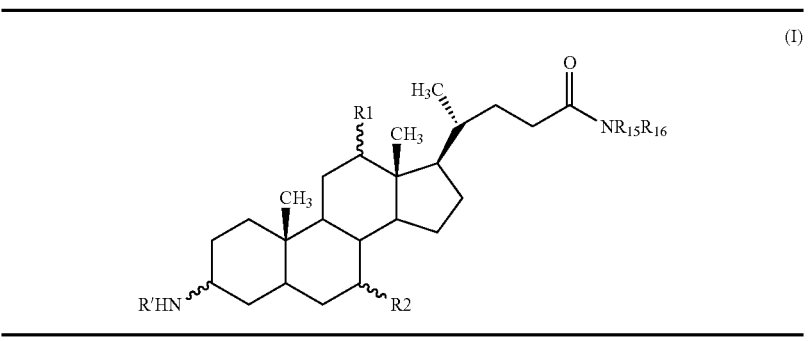
(I)
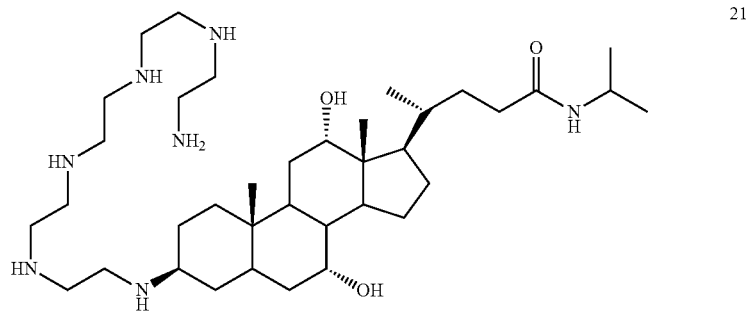
21
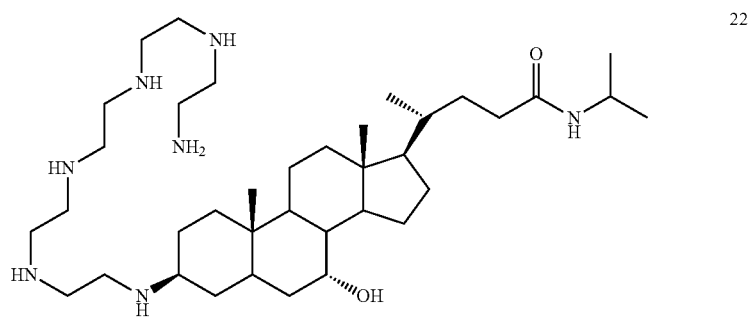
22
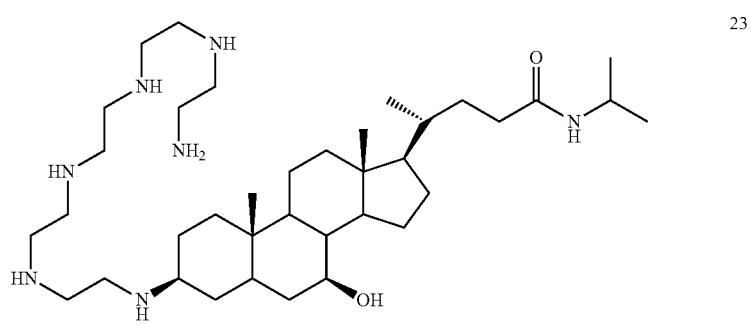
23
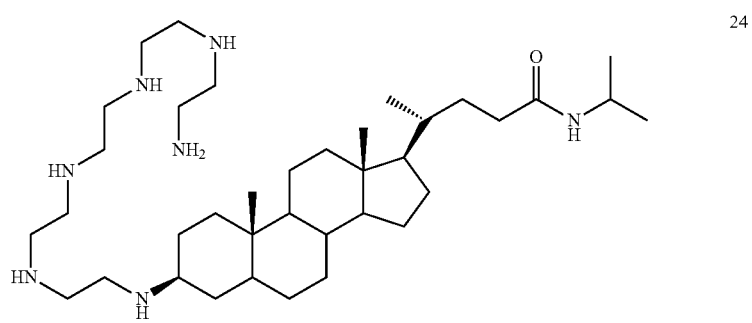
24

TABLE 1-continued
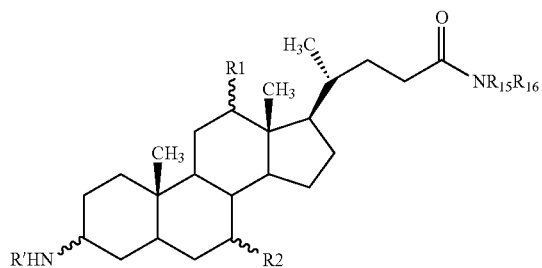
(I)
| Formula (Ic) |
|---|
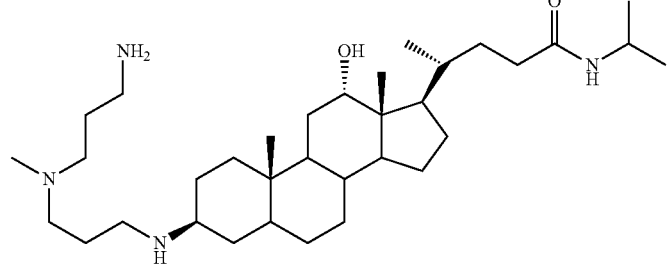
25
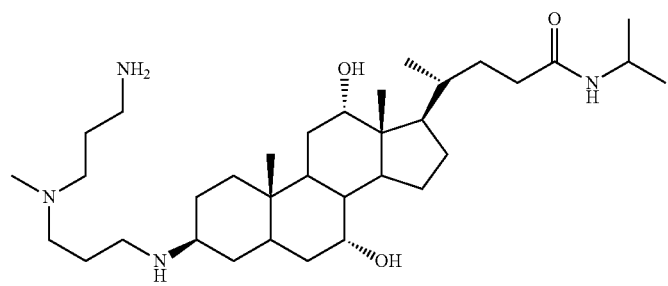 [SMILES: CC(C)NC(=O)CC[C@@H](C)[C@H]1CCC2C3C(C[C@H](O)[C@@]21C)[C@@]1(C)CC[C@H](NCCCN(C)CCCN)CC1C[C@H]3O]
26
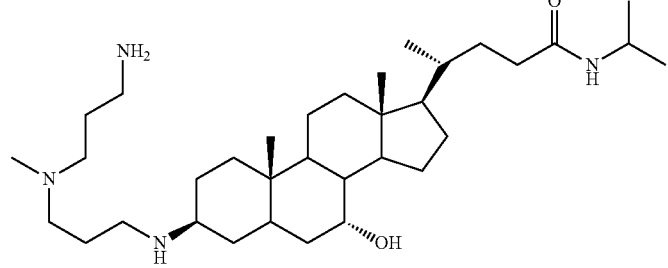
27
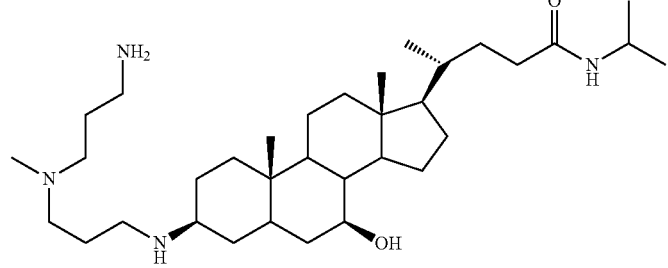
28

TABLE 1-continued
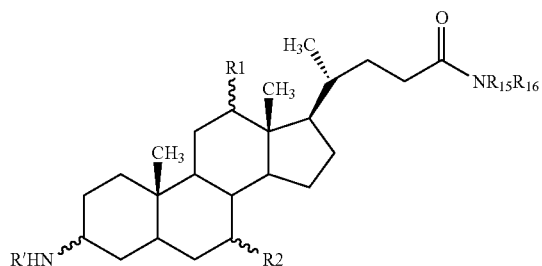
(I)
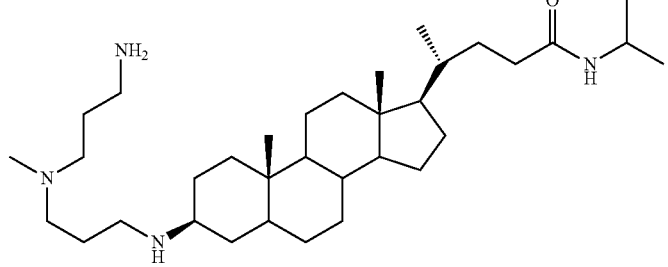
29
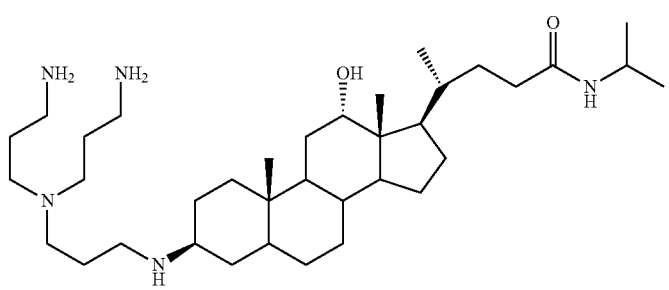 [SMILES: CC(C)NC(=O)CC[C@@H](C)[C@H]1CCC2C3CCC4C[C@@H](NCCCN(CCCN)CCCN)CC[C@]4(C)C3C[C@H](O)[C@@]21C]
42
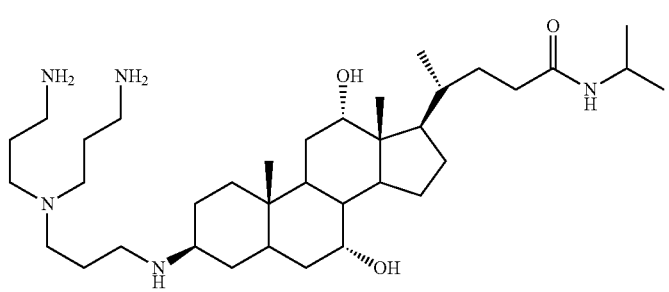 [SMILES: CC(C)NC(=O)CC[C@@H](C)[C@H]1CCC2C3C(C[C@H](O)[C@@]21C)[C@@]1(C)CC[C@H](NCCCN(CCCN)CCCN)CC1C[C@H]3O]
43
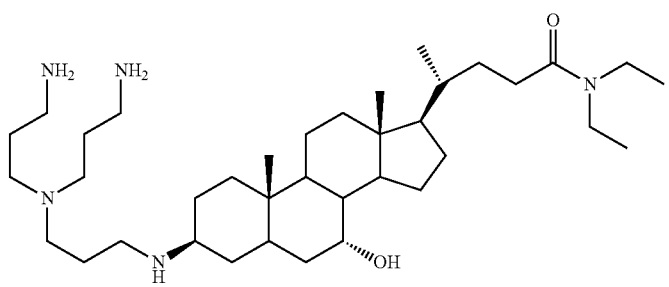 [SMILES: CCN(CC)C(=O)CC[C@@H](C)[C@H]1CCC2C3C(CC[C@@]21C)[C@@]1(C)CC[C@H](NCCCN(CCCN)CCCN)CC1C[C@H]3O]
44

TABLE 1-continued
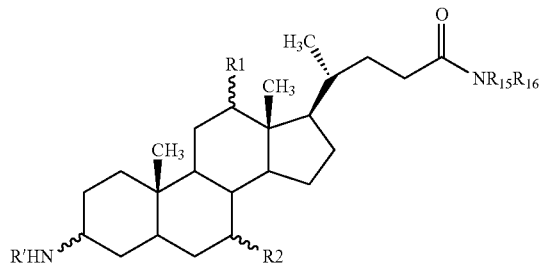
(I)
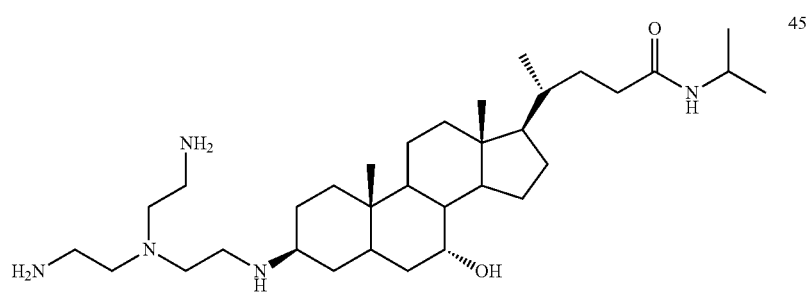
45
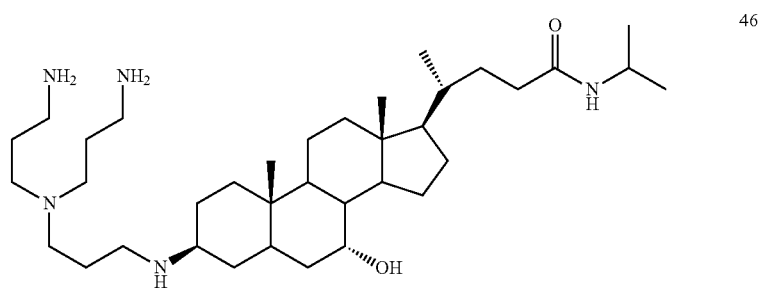
46
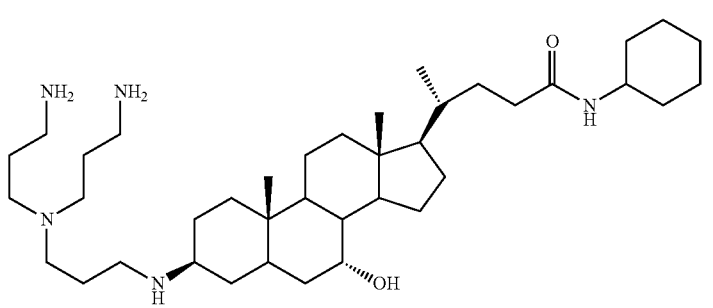 [SMILES: C[C@H](CCC(=O)NC1CCCCC1)[C@H]1CCC2C3C(CC[C@@]21C)[C@@]1(C)CC[C@H](NCCCN(CCCN)CCCN)CC1C[C@H]3O]
47
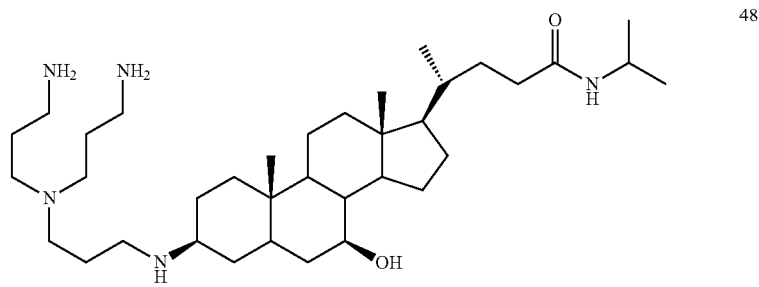
48

TABLE 1-continued
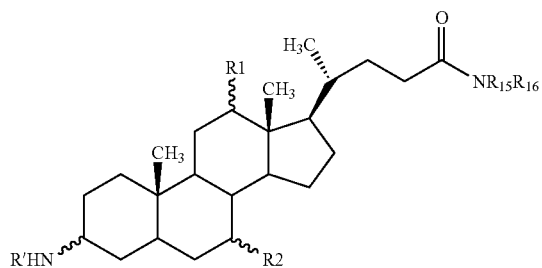
(I)
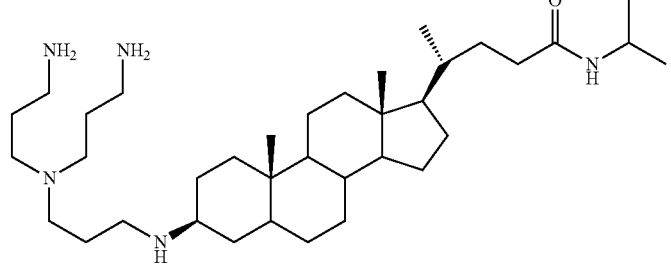
49
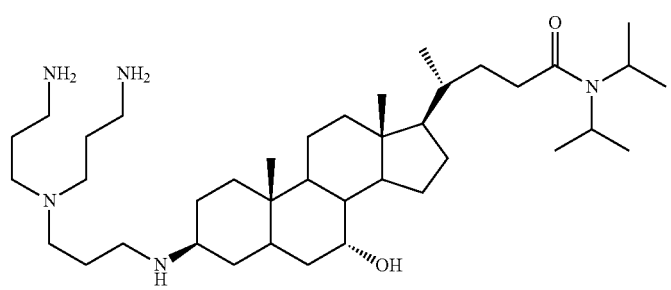 [SMILES: CC(C)N(C(=O)CC[C@@H](C)[C@H]1CCC2C3C(CC[C@@]21C)[C@@]1(C)CC[C@H](NCCCN(CCCN)CCCN)CC1C[C@H]3O)C(C)C]
56
Formula (Id)
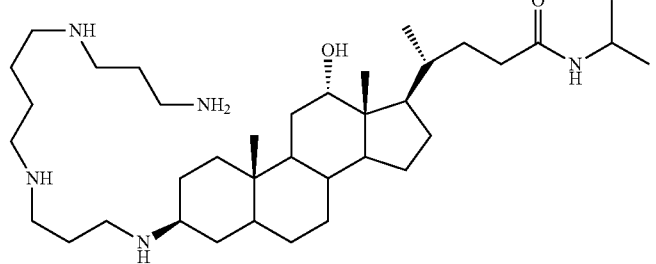
30
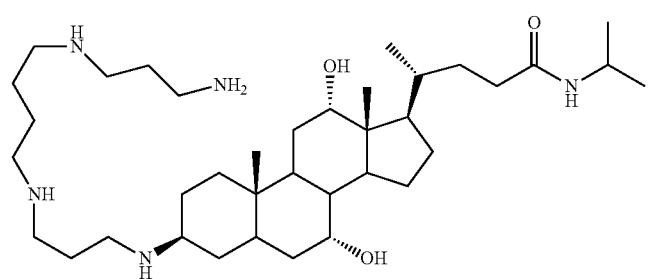 [SMILES: CC(C)NC(=O)CC[C@@H](C)[C@H]1CCC2C3C(C[C@H](O)[C@@]21C)[C@@]1(C)CC[C@H](NCCCNCCCCNCCCN)CC1C[C@H]3O]
31

TABLE 1-continued
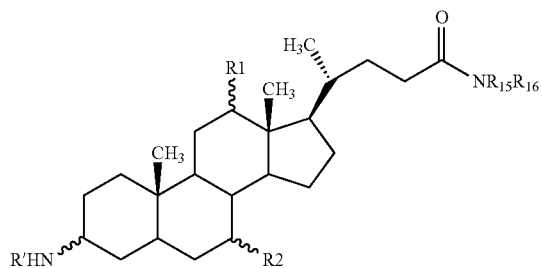
(I)
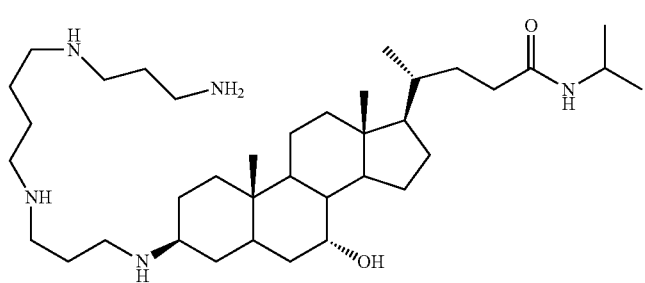 [SMILES: CC(C)NC(=O)CC[C@@H](C)[C@H]1CCC2C3C(CC[C@@]21C)[C@@]1(C)CC[C@H](NCCCNCCCCNCCCN)CC1C[C@H]3O]
32
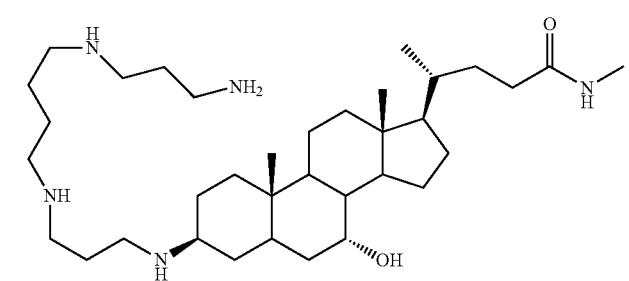 [SMILES: CNC(=O)CC[C@@H](C)[C@H]1CCC2C3C(CC[C@@]21C)[C@@]1(C)CC[C@H](NCCCNCCCCNCCCN)CC1C[C@H]3O]
33
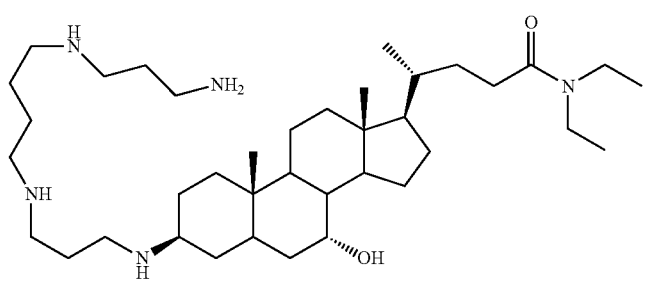 [SMILES: CCN(CC)C(=O)CC[C@@H](C)[C@H]1CCC2C3C(CC[C@@]21C)[C@@]1(C)CC[C@H](NCCCNCCCCNCCCN)CC1C[C@H]3O]
34
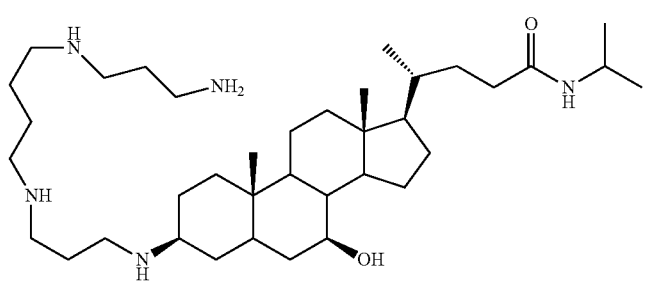 [SMILES: CC(C)NC(=O)CC[C@@H](C)[C@H]1CCC2C3C(CC[C@@]21C)[C@@]1(C)CC[C@H](NCCCNCCCCNCCCN)CC1C[C@@H]3O]
35

TABLE 1-continued
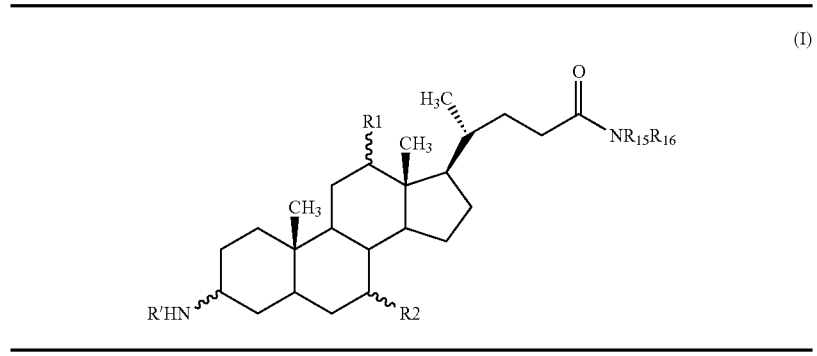
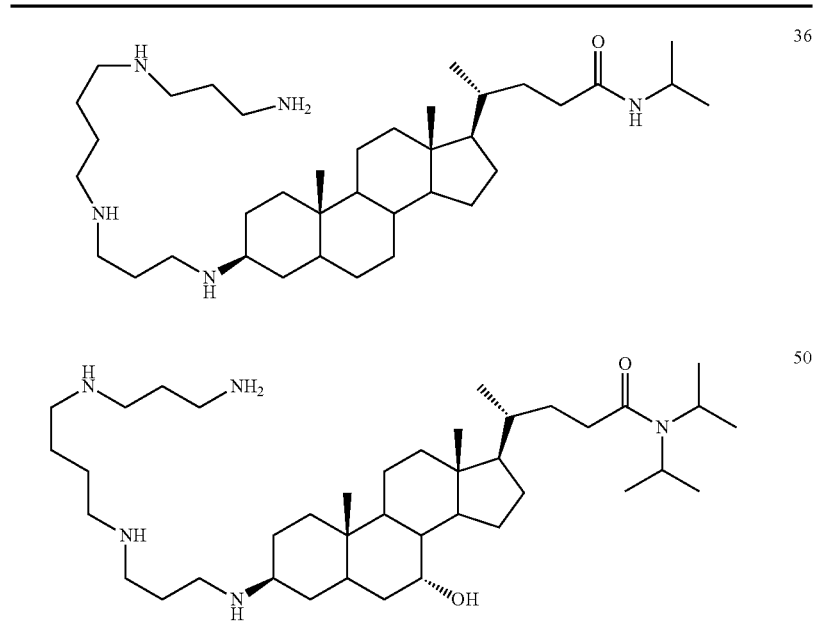

TABLE 1-continued
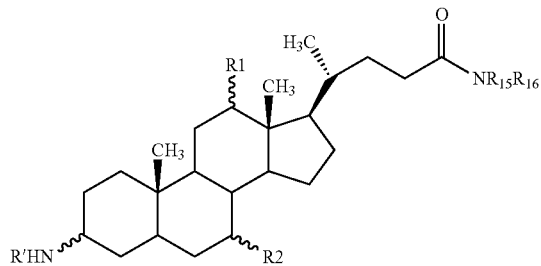
Formula (Ic)
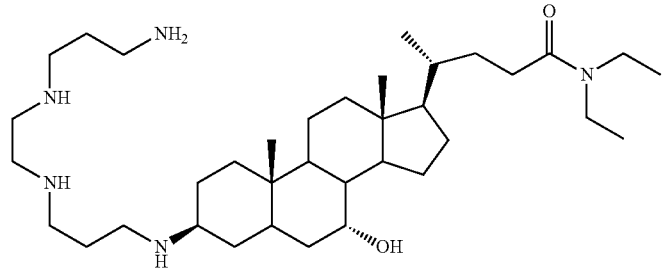 [SMILES: CCN(CC)C(=O)CC[C@@H](C)[C@H]1CCC2C3C(CC[C@@]21C)[C@@]1(C)CC[C@H](NCCCNCCNCCCN)CC1C[C@H]3O] 53
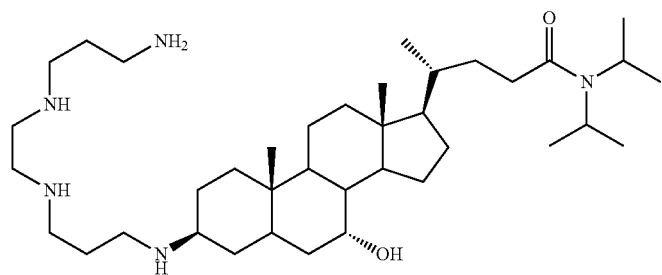 [SMILES: CC(C)N(C(=O)CC[C@@H](C)[C@H]1CCC2C3C(CC[C@@]21C)[C@@]1(C)CC[C@H](NCCCNCCNCCCN)CC1C[C@H]3O)C(C)C] 54
The invention also covers a 50/50 mixture of 3β-spermidino-N-isopropylchenodeoxycholamide and of 3β-N-[4'N-(3'-aminopropyl)aminobutyl]amino-N-isopropylchenodeoxycholamide, referred to as compound (55) in the description that follows.
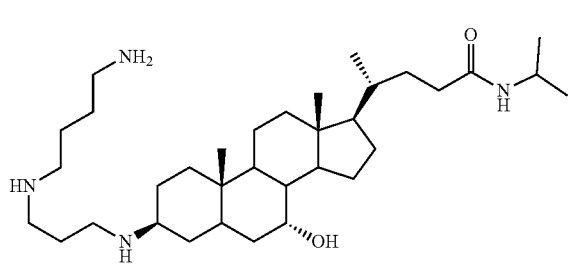 55
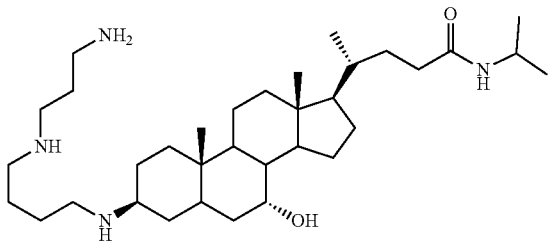

TABLE II

The chemical structures synthesized were all confirmed by proton ($^1$H) and/or carbon ($^{13}$C) NMR analysis in deuterated chloroform $CDCl_3$ or deuterated methanol $CD_3OD$ on a machine of Brüker AC 300 type. The chemical shifts δ are expressed in ppm. The recording frequencies of the nuclei and the references used are as follows:
$^1$H NMR: 300 MHz, $Si(CH_3)_4$
$^{13}$C NMR: 75 MHz, $Si(CH_3)_4$ Ex. Characterization 1. $^1$H NMR (250 MHz, $CD_3OD$): δ (ppm) = 3.94 (m, 2H), 2.71-2.59 (m, 13H), 2.21-0.70 (m, 54H). $^{13}$C NMR (63 MHz, $CD_3OD$): δ (ppm) = 175.93, 74.19, 59.07, 49.31, 49.00, 48.24, 47.74, 45.85, 44.08, 42.41, 40.78, 37.59, 37.12, 37.01, 35.95, 35.92, 34.94, 34.58, 34.36, 33.56, 30.50, 30.30, 29.98, 28.84, 28.64, 28.27, 27.64, 25.04, 24.08, 22.82, 22.76, 17.85, 13.35

2. $^1$H NMR (250 MHz, $CD_3OD$): δ (ppm) = 3.99-3.89 (m, 2H), 2.72-2.51 (m, 9H), 2.25-0.70 (m, 51H). $^{13}$C NMR (63 MHz, $CD_3OD$): δ (ppm) = 175.55, 72.85, 59.06, 49.33, 49.06, 48.42, 48.25, 47.76, 45.84, 44.06, 42.41, 40.75, 37.58, 37.10, 37.01, 35.91, 34.95, 34.47, 34.37, 33.55, 33.34, 30.33, 29.98, 28.84, 28.62, 28.19, 27.64, 25.04, 24.07, 22.82, 22.76, 17.84, 13.35

3. $^1$H NMR (250 MHz, $CD_3OD$): δ (ppm) = 3.99-3.89 (m, 2H), 2.69-2.38 (m, 17H), 2.27-0.70 (m, 50H). $^{13}$C NMR (63 MHz, $CD_3OD$): δ (ppm) = 175.87, 74.13, 59.06, 58.03, 57.50, 54.10, 54.03, 49.30, 48.21, 47.75, 46.29, 44.04, 42.38, 41.16, 37.58, 37.01, 35.92, 34.92, 34.64, 34.35, 33.53, 30.55, 30.00, 28.85, 28.65, 28.34, 27.65, 27.42, 25.06, 24.12, 22.85, 22.79, 17.87, 13.38

4. $^1$H NMR (250 MHz, $CD_3OD$): δ (ppm) = 3.96-3.95 (m, 2H), 3.80 (m, 1H), 2.76-2.69 (m, 13H), 2.54-0.72 (m, 53H). $^{13}$C NMR (63 MHz, $CD_3OD$): δ (ppm) = 175.88, 74.01, 69.00, 59.32, 57.39, 54.01, 48.21, 47.64, 45.53, 43.55, 43.13, 42.39, 41.16, 41.00, 40.54, 37.07, 36.92, 36.73, 36.38, 35.98, 34.43, 33.56, 32.12, 29.65, 28.89, 28.02, 27.45, 24.38, 23.44, 22.84, 22.78, 17.93, 13.16

5. $^1$H NMR (250 MHz, $CD_3OD$): δ (ppm) = 3.97-3.94 (m, 2H), 3.80 (m, 1H), 2.90-2.59 (m, 9H), 2.29-0.71 (m, 50H). $^{13}$C NMR (63 MHz, $CD_3OD$): δ (ppm) = 175.91, 74.00, 68.98, 59.23, 49.00, 48.22, 47.62, 45.64, 43.42, 43.19, 42.40, 41.15, 40.42, 37.07, 36.74, 36.30, 35.89, 34.43, 33.56, 31.66, 29.69, 28.87, 28.32, 28.05, 27.14, 24.34, 23.36, 22.82, 22.76, 17.90, 13.15

6. $^1$H NMR (250 MHz, $CD_3OD$): δ (ppm) = 3.94 (m, 2H), 3.79 (m, 1H), 2.76-2.39 (m, 23H), 2.28-0.71 (m, 43H). $^{13}$C NMR (63 MHz, $CD_3OD$): δ (ppm) = 175.93, 74.03, 69.03, 59.34, 57.97, 57.44, 54.10, 54.02, 47.66, 46.24, 46.08, 43.65, 43.14, 42.41, 41.21, 41.09, 37.28, 37.07, 36.42, 36.02, 34.43, 33.56, 30.11, 29.74, 28.87, 28.06, 27.92, 26.67, 24.38, 23.48, 22.83, 22.76, 17.91, 13.16

7. $^1$H NMR (250 MHz, $CD_3OD$): δ (ppm) = 3.94 (m, 1H), 3.80 (m, 1H), 2.92-2.74 (m, 13H), 2.20-0.69 (m, 54H). $^{13}$C NMR (63 MHz, $CD_3OD$): δ (ppm) = 175.88, 68.97, 59.31, 57.60, 51.74, 48.54, 45.26, 43.83, 43.42, 42.43, 41.21, 40.91, 40.32, 37.06, 36.65, 36.06, 35.88, 34.40, 34.21, 33.56, 30.84, 29.44, 29.04, 27.99, 27.01, 24.74, 23.55, 22.81, 22.73, 21.91, 19.07, 12.33

8. $^1$H NMR (250 MHz, $CD_3OD$): δ (ppm) = 3.95 (m, 1H), 3.80 (m, 1H), 2.75-2.63 (m, 9H), 2.27-0.70 (m, 51H). $^{13}$C NMR (63 MHz, $CD_3OD$): δ (ppm) = 175.82, 69.03, 59.40, 57.51, 51.69, 48.94, 48.28, 45.64, 43.82, 43.61, 42.41, 41.20, 40.94, 40.63, 37.05, 36.76, 36.03, 34.36, 34.19, 33.55, 32.81, 29.57, 29.45, 28.01, 24.77, 23.72, 22.83, 22.76, 21.91, 19.11, 12.37

9. $^1$H NMR (250 MHz, $CD_3OD$): δ (ppm) = 3.94 (m, 1H), 3.81 (m, 1H), 3.09-2.82 (m, 17H), 2.20-0.70 (m, 50H). $^{13}$C NMR (63 MHz, $CD_3OD$): δ (ppm) = 175.88, 68.81, 59.37, 57.67, 55.76, 52.43, 52.27, 52.16, 52.09, 51.82, 51.99, 43.83, 43.09, 42.44, 41.24, 40.90, 40.75, 37.07, 36.67, 36.46, 34.43, 34.24, 34.16, 33.56, 30.91, 30.89, 29.46, 25.36, 24.74, 23.55, 22.80, 22.73, 19.08, 12.33

10. $^1$H NMR (250 MHz, $CD_3OD$): δ (ppm) = 3.79 (m, 1H), 3.65 (s, 3H), 2.73-2.61 (m, 13H), 2.24-0.69 (m, 48H). $^{13}$C NMR (63 MHz, $CD_3OD$): δ (ppm) = 176.40, 69.03, 59.45, 57.44, 52.18, 51.67, 48.95, 48.43, 45.73, 43.81, 43.69, 41.20, 40.96, 40.72, 37.57, 37.21, 36.80, 36.10, 34.18, 33.21, 32.39, 31.97, 30.13, 30.02, 29.41, 28.29, 24.79, 23.79, 21.95, 19.00, 12.42

11. $^1$H NMR (250 MHz, $CD_3OD$): δ (ppm) = 3.79 (m, 1H), 3.65 (s, 3H), 2.72-2.63 (m, 9H), 2.44-0.69 (m, 45H). $^{13}$C NMR (63 MHz, $CD_3OD$): δ (ppm) = 176.38, 68.95, 59.31, 57.34, 52.02, 51.57, 48.86, 48.19, 45.55, 43.70, 43.54, 41.10, 40.85, 40.55, 37.00, 36.79, 36.67, 35.93, 34.09, 32.77, 32.28, 31.87, 29.57, 29.29, 27.97, 24.67, 23.63, 21.83, 18.87, 12.28

12. $^1$H NMR (250 MHz, $CD_3OD$): δ (ppm) = 3.79 (m, 1H), 3.65 (s, 3H), 2.71-0.42 (m, 17H), 2.32-0.70 (m, 44H). $^{13}$C NMR (63 MHz, $CD_3OD$): δ (ppm) = 176.46, 69.03, 59.36, 58.05, 57.47, 54.13, 53.99, 52.18, 51.69, 46.18, 43.82, 43.66, 41.22, 41.12, 40.97, 37.58, 37.18, 37.18, 36.90, 36.79, 36.07, 34.21, 32.39, 31.97, 30.35, 29.40, 28.36, 26.93, 24.77, 23.75, 21.93, 18.98, 12.40

13. $^1$H NMR (250 MHz, $CD_3OD$): δ (ppm) = 3.79 (m, 1H), 3.38 (m, 4H), 2.72-2.59 (m, 8H), 2.38-0.70 (m, 51H). $^{13}$C NMR (63 MHz, $CD_3OD$): δ (ppm) = 175.42, 69.07, 59.48, 57.47, 51.66, 49.08, 48.42, 45.79, 43.83, 43.74, 41.62, 41.21, 40.98, 40.79, 37.86, 37.30, 37.18, 36.83, 36.11, 34.18, 33.58, 33.23, 31.15, 30.41, 29.48, 28.54, 24.80, 23.82, 21.94, 19.25, 14.84, 13.47, 12.42

14. $^1$H NMR (250 MHz, $CD_3OD$): δ (ppm) = 3.94 (m, 1H), 3.46 (m, 1H), 2.89-2.65 (m, 13H), 2.54-0.71 (m, 54H). $^{13}$C NMR (63 MHz, $CD_3OD$): δ (ppm) = 175.87, 72.04, 58.88, 57.64, 56.75, 48.31, 46.72, 45.74, 44.94, 44.66, 44.46, 42.42, 41.70, 40.80, 40.56, 38.82, 36.97, 36.68, 35.85, 35.75, 34.97, 34.40, TABLE II-continued The chemical structures synthesized were all confirmed by proton ($^1$H) and/or carbon ($^{13}$C) NMR analysis in deuterated chloroform CDCl$_3$ or deuterated methanol CD$_3$OD on a machine of Brüker AC 300 type. The chemical shifts δ are expressed in ppm. The recording frequencies of the nuclei and the references used are as follows:
$^1$H NMR: 300 MHz, Si(CH$_3$)$_4$
$^{13}$C NMR: 75 MHz, Si(CH$_3$)$_4$

| Ex. | Characterization |
|---|---|
|  | 33.60, 32.19, 29.84, 29.71, 29.66, 28.10, 24.25, 22.81, 22.76, 22.54, 19.22, 12.80 |
| 15 | $^1$H NMR (250 MHz, CD$_3$OD): δ (ppm) = 3.94 (m, 1H), 3.47 (m, 1H), 2.85-2.49 (m, 9H), 2.24-0.71 (m, 51H). $^{13}$C NMR (63 MHz, CD$_3$OD): δ (ppm) = 175.87, 72.06, 58.89, 57.65, 56.74, 48.94, 48.39, 45.85, 44.95, 44.67, 44.50, 42.42, 41.72, 40.81, 40.70, 38.87, 36.97, 36.75, 35.86, 35.78, 35.25, 34.39, 33.60, 33.06, 30.26, 29.84, 28.10, 24.28, 22.81, 22.76, 22.54, 19.23, 12.80 |
| 16 | $^1$H NMR (250 MHz, CD$_3$OD): δ (ppm) = 3.94 (m, 1H), 3.47 (m, 1H), 2.70-2.38 (m, 17H), 2.20-0.71 (m, 50H). $^{13}$C NMR (63 MHz, CD$_3$OD): δ (ppm) = 175.74, 72.01, 58.86, 58.05, 57.67, 56.74, 54.13, 54.03, 46.41, 44.94, 44.65, 44.48, 44.39, 42.38, 41.73, 41.16, 40.81, 38.93, 36.97, 36.80, 35.89, 35.78, 35.49, 34.39, 33.59, 30.51, 29.87, 28.33, 28.11, 27.37, 24.37, 22.87, 22.81, 22.56, 19.29, 12.87 |
| 17 | $^1$H NMR (250 MHz, CD$_3$OD): δ (ppm) = 3.94 (m, 1H), 2.96-2.77 (m, 13H), 2.52-0.69 (m, 55H). $^{13}$C NMR (63 MHz, CD$_3$OD): δ (ppm) = 175.89, 59.07, 58.00, 57.69, 47.93, 44.06, 42.44, 41.91, 41.59, 39.96, 37.29, 36.99, 36.03, 34.40, 33.53, 29.42, 29.01, 28.75, 28.24, 26.01, 25.37, 23.96, 23.93, 22.79, 22.73, 22.07, 19.03, 12.61 |
| 18 | $^1$H NMR (250 MHz, CD$_3$OD): δ (ppm) = 3.94 (m, 1H), 2.74-2.62 (m, 9H), 2.25-0.69 (m, 52H). $^{13}$C NMR (63 MHz, CD$_3$OD): δ (ppm) = 175.86, 59.04, 58.06, 57.63, 48.92, 48.37, 45.83, 44.07, 43.92, 42.43, 41.97, 41.67, 40.67, 37.37, 37.05, 36.98, 36.26, 34.35, 33.52, 32.90, 30.02, 29.44, 28.55, 28.11, 27.80, 25.42, 24.28, 22.81, 22.75, 22.11, 19.06, 12.65 |
| 19 | $^1$H NMR (250 MHz, CD$_3$OD): δ (ppm) = 3.94 (m, 1H), 2.72-2.39 (m, 15H), 2.23-0.96 (m, 53H). $^{13}$C NMR (63 MHz, CD$_3$OD): δ (ppm) = 175.88, 59.01, 58.12, 58.02, 57.66, 57.50, 54.14, 54.02, 46.36, 44.09, 43.90, 42.43, 42.00, 41.69, 41.09, 37.37, 37.06, 36.99, 36.27, 34.40, 34.35, 33.53, 30.17, 29.44, 28.55, 28.28, 27.83, 27.12, 25.42, 24.28, 22.81, 22.75, 22.11, 19.05, 12.65 |
| 20 | $^1$H NMR (250 MHz, CD$_3$OD): δ (ppm) = 3.99-3.89 (m, 2H), 2.85-2.54 (m, 21H), 2.27-0.70 (m, 50H). $^{13}$C NMR (63 MHz, CD$_3$OD): δ (ppm) = 175.87, 74.06, 59.10, 57.27, 55.25, 55.05, 54.99, 54.27, 54.18, 49.31, 48.23, 47.74, 46.97, 46.32, 46.18, 43.95, 42.38, 37.55, 36.99, 35.84, 34.94, 34.39, 33.52, 29.98, 28.84, 28.55, 27.60, 25.02, 24.02, 22.84, 22.78, 22.27, 17.86, 13.37 |
| 21 | $^1$H NMR (250 MHz, CD$_3$OD): δ (ppm) = 3.96-3.91 (m, 1H), 3.79 (m, 1H), 2.85-2.46 (m, 24H), 2.24-0.93 (m, 43H), 0.71 (s, 3H). $^{13}$C NMR (63 MHz, CD$_3$OD): δ (ppm) = 175.95, 74.10, 69.11, 59.54, 55.35, 54.48, 54.27, 54.07, 49.68, 48.19, 47.66, 47.07, 46.21, 43.73, 43.11, 42.41, 41.89, 41.21, 39.08, 37.77, 37.14, 37.06, 36.48, 36.06, 34.40, 33.55, 29.70, 28.87, 28.34, 28.04, 24.38, 23.52, 22.82, 22.76, 17.91, 13.15 |
| 22 | $^1$H NMR (250 MHz, CD$_3$OD): δ (ppm) = 3.94 (m, 1H), 3.79 (m, 1H), 2.85-2.43 (m, 23H), 2.37-0.69 (m, 48H). $^{13}$C NMR (63 MHz, CD$_3$OD): δ (ppm) = 175.87, 69.10, 59.59, 58.60, 57.52, 55.37, 54.48, 54.28, 54.08, 51.70, 43.84, 42.42, 41.92, 41.23, 40.97, 39.11, 37.23, 37.05, 36.82, 36.10, 34.37, 34.21, 33.56, 29.44, 28.64, 28.59, 24.78, 23.76, 22.83, 22.76, 21.94, 19.10, 12.36 |
| 23 | $^1$H NMR (250 MHz, CD$_3$OD): δ (ppm) = 3.94 (m, 1H), 3.47 (m, 1H), 2.84-2.46 (m, 22H), 2.26-0.71 (m, 49H). $^{13}$C NMR (63 MHz, CD$_3$OD): δ (ppm) = 175.81, 72.04, 57.68, 56.74, 54.29, 54.26, 49.93, 47.10, 46.93, 46.37, 46.23, 44.94, 44.66, 44.50, 42.41, 41.93, 41.73, 40.83, 39.12, 38.90, 36.97, 36.77, 35.78, 34.39, 33.59, 29.85, 28.41, 28.10, 24.33, 22.84, 22.78, 22.54, 19.25, 12.83 |
| 24 | $^1$H NMR (250 MHz, CD$_3$OD): δ (ppm) = 3.95 (m, 1H), 2.84-2.53 (m, 22H), 2.27-0.69 (m, 50H). $^{13}$C NMR (63 MHz, CD$_3$OD): δ (ppm) = 175.80, 58.07, 57.63, 54.28, 52.23, 44.06, 43.91, 42.41, 41.99, 41.81, 41.67, 37.37, 36.97, 36.27, 34.39, 34.34, 33.51, 29.43, 28.58, 28.42, 28.32, 27.83, 25.44, 24.33, 22.84, 22.78, 22.11, 19.09, 12.69 |
| 25 | $^1$H NMR (250 MHz, CD$_3$OD): δ (ppm) = 3.99-3.91 (m, 2H), 2.68-0.70 (m, 62H). $^{13}$C NMR (63 MHz, CD$_3$OD): δ (ppm) = 175.84, 74.13, 59.10, 57.14, 56.62, 56.57, 49.29, 47.69, 46.19, 44.06, 42.47, 42.37, 41.13, 37.58, 36.99, 35.91, 34.92, 34.66, 34.33, 33.53, 31.06, 30.98, 29.98, 28.84, 28.65, 28.33, 27.92, 27.65, 25.06, 24.14, 22.86, 22.80, 17.87, 13.39 |
| 26 | $^1$H NMR (250 MHz, CD$_3$OD): δ (ppm) = 3.94-3.89 (m, 2H), 2.75-2.40 (m, 14H), 2.24-0.85 (m, 45H), 0.71 (s, 3H). $^{13}$C NMR (63 MHz, CD$_3$OD): δ (ppm) = 175.98, 74.08, 69.06, 59.99, 57.30, 56.64, 56.60, 50.72, 48.22, 47.67, 42.43, 41.05, 37.09, 37.03, 36.43, 36.00, 34.43, 34.37, 33.56, 30.61, 30.52, 28.89, 27.61, 24.36, 23.46, 22.81, 22.74, 17.89, 13.15 |
| 27 | $^1$H NMR (250 MHz, CD$_3$OD): δ (ppm) = 3.94 (m, 1H), 3.79 (m, 1H), 2.70-0.69 (m, 51H). $^{13}$C NMR (62 MHz, CD$_3$OD): δ (ppm) = 175.80, 69.04, 59.50, 57.50, 57.13, 56.55, 51.69, 46.04, 43.82, 43.69, 42.43, 42.39, 41.21, 41.05, 40.96, 37.60, 37.21, 37.04, 36.80, 36.08, 34.35, 34.19, 33.54, 30.69, 29.45, 28.35, 27.52, 24.78, 23.77, 22.84, 22.77, 21.93, 19.12, 12.39 |
| 28 | $^1$H NMR (250 MHz, CD$_3$OD): δ (ppm) = 3.94 (m, 1H), 3.47 (m, 1H), 2.75-2.32 (m, 12H), 2.24-0.71 (m, 50H). $^{13}$C NMR (62 MHz, CD$_3$OD): δ (ppm) = 175.84, |

TABLE II-continued

The chemical structures synthesized were all confirmed by proton ($^1$H) and/or carbon ($^{13}$C) NMR analysis in deuterated chloroform CDCl$_3$ or deuterated methanol CD$_3$OD on a machine of Brüker AC 300 type. The chemical shifts δ are expressed in ppm. The recording frequencies of the nuclei and the references used are as follows:
$^1$H NMR: 300 MHz, Si(CH$_3$)$_4$
$^{13}$C NMR: 75 MHz, Si(CH$_3$)$_4$

| Ex. | Characterization |
|---|---|
|  | 72.05, 58.94, 57.64, 57.01, 56.73, 56.57, 46.17, 44.93, 44.82, 44.66, 44.48, 42.41, 41.70, 41.05, 40.80, 36.95, 35.77, 34.41, 34.39, 33.59, 30.54, 30.42, 29.84, 28.09, 27.74, 24.30, 22.83, 22.76, 19.24, 12.82 |
| 29 | $^1$H NMR (250 MHz, CD$_3$OD): δ (ppm) = 3.94 (m, 1H), 2.75-2.37 (m, 10H), 2.24-0.69 (m, 53H). $^{13}$C NMR (62 MHz, CD$_3$OD): δ (ppm) = 175.81, 58.05, 57.59, 56.57, 46.26, 44.06, 43.98, 42.49, 42.41, 41.97, 41.66, 41.14, 37.39, 37.22, 36.97, 36.31, 34.37, 33.51, 31.09, 31.04, 29.43, 27.82, 25.44, 24.36, 22.83, 22.77, 22.11, 19.08, 12.69 |
| 30 | $^1$H NMR (250 MHz, CD$_3$OD): δ (ppm) = 3.94-3.91 (m, 2H), 2.83-2.53 (m, 13H), 2.26-0.70 (m, 56H). $^{13}$C NMR (63 MHz, CD$_3$OD): δ (ppm) = 175.93, 74.12, 59.03, 49.98, 49.30, 48.27, 47.76, 45.42, 43.93, 42.41, 40.37, 37.56, 37.01, 35.81, 34.94, 34.41, 33.55, 31.13, 29.98, 28.84, 28.74, 28.51, 27.61, 27.43, 25.03, 23.91, 22.82, 22.76, 17.86, 13.34 |
| 31 | $^1$H NMR (250 MHz, CD$_3$OD): δ (ppm) = 3.96-3.94 (m, 2H), 3.79 (m, 1H), 2.85-2.68 (m, 13H), 2.54-0.71 (m, 55H). $^{13}$C NMR (63 MHz, CD$_3$OD): δ (ppm) = 175.91, 74.02, 69.02, 59.34, 50.08, 48.66, 48.21, 47.64, 45.47, 43.52, 43.12, 42.40, 41.16, 40.48, 37.08, 36.87, 36.65, 36.49, 36.35, 35.95, 34.44, 33.56, 31.65, 29.68, 28.87, 28.64, 28.02, 27.84, 27.78, 27.36, 24.36, 23.41, 22.82, 22.76, 17.91, 13.14 |
| 32 | $^1$H NMR (250 MHz, CD$_3$OD): δ (ppm) = 3.89 (m, 1H), 3.74 (m, 1H), 2.70-2.41 (m, 13H), 2.17-0.64 (m, 56H). $^{13}$C NMR (63 MHz, CD$_3$OD): δ (ppm) = 175.82, 69.03, 59.40, 57.55, 51.70, 50.44, 50.33, 48.27, 45.61, 43.83, 43.63, 42.41, 41.22, 40.95, 40.63, 37.06, 36.76, 36.04, 34.37, 34.21, 33.56, 32.53, 29.46, 29.37, 28.10, 27.98, 24.78, 23.71, 22.83, 22.76, 21.94, 19.11, 12.37 |
| 33 | $^1$H NMR (250 MHz, CD$_3$OD): δ (ppm) = 3.79 (m, 1H), 3.65 (s, 3H), 2.75-2.64 (m, 13H), 2.27-0.69 (m, 50H). $^{13}$C NMR (63 MHz, CD$_3$OD): δ (ppm) = 176.47, 69.04, 59.40, 57.46, 52.17, 51.69, 50.46, 50.36, 48.27, 45.62, 43.81, 43.63, 41.20, 40.95, 40.63, 37.27, 37.11, 36.90, 36.76, 36.03, 34.19, 32.61, 32.39, 31.97, 29.46, 29.40, 28.11, 28.04, 24.77, 23.72, 21.93, 18.96, 12.37 |
| 34 | $^1$H NMR (250 MHz, CD$_3$OD): δ (ppm) = 3.79 (m, 1H), 3.38 (m, 4H), 2.73-2.62 (m, 13H), 2.40-0.70 (m, 55H). $^{13}$C NMR (63 MHz, CD$_3$OD): δ (ppm) = 175.43, 69.05, 59.44, 57.50, 51.67, 50.57, 50.49, 48.89, 48.34, 45.69, 43.83, 43.75, 43.68, 41.62, 41.20, 40.97, 40.70, 37.54, 37.18, 36.79, 36.07, 34.18, 33.23, 33.07, 31.17, 29.89, 29.48, 28.25, 24.79, 23.76, 21.94, 19.23, 14.83, 13.45, 12.40 |
| 35 | $^1$H NMR (250 MHz, CD$_3$OD): δ (ppm) = 3.94 (m, 1H), 3.47 (m, 1H), 2.98-2.52 (m, 15H), 2.33-0.71 (m, 54H). $^{13}$C NMR (63 MHz, CD$_3$OD): δ (ppm) = 175.86, 72.04, 58.87, 57.65, 56.76, 55.13, 50.29, 45.73, 45.66, 44.94, 44.66, 44.44, 42.42, 41.69, 40.80, 40.56, 38.81, 36.97, 36.65, 35.74, 34.42, 33.60, 32.03, 29.83, 29.56, 28.02, 24.32, 22.82, 22.76, 22.54, 19.23, 12.80 |
| 36 | $^1$H NMR (250 MHz, CD$_3$OD): δ (ppm) = 3.94 (m, 1H), 2.98-2.69 (m, 13H), 2.20-0.69 (m, 57H). $^{13}$C NMR (63 MHz, CD$_3$OD): δ (ppm) = 175.85, 59.05, 57.98, 57.65, 49.71, 49.65, 47.94, 45.00, 44.05, 43.58, 42.43, 41.88, 41.59, 39.91, 37.28, 36.98, 36.29, 36.03, 34.38, 33.53, 29.43, 28.88, 27.39, 27.33, 25.38, 24.51, 24.00, 22.81, 22.74, 22.06, 19.04, 12.63 |
| 37 | $^1$H NMR (250 MHz, CD$_3$OD): δ (ppm) = 4.05 (m, 1H), 3.80 (m, 1H), 3.53 (m, 1H), 2.79-2.63 (m, 8H), 2.52-0.95 (m, 54H), 0.71 (s, 3H). $^{13}$C NMR (63 MHz, CD$_3$OD): δ (ppm) = 175.27, 69.02, 59.41, 57.49, 51.69, 50.64, 48.95, 48.27, 47.11, 45.69, 43.84, 43.59, 41.19, 40.95, 40.65, 37.25, 37.10, 37.04, 36.74, 36.00, 34.21, 33.54, 33.38, 32.80, 29.54, 29.37, 27.89, 24.78, 23.70, 21.93, 21.30, 21.12, 19.23, 12.39. |
| 38 | $^1$H NMR (250 MHz, CD$_3$OD): δ (ppm) = 3.79 (m, 1H), 3.61 (m, 1H), 2.87-2.61 (m, 9H), 2.47-0.95 (m, 52H), 0.69 (s, 3H). $^{13}$C NMR (63 MHz, CD$_3$OD): δ (ppm) = 175.86, 69.08, 59.44, 57.54, 51.70, 49.75, 48.34, 45.71, 43.84, 43.66, 41.21, 40.95, 40.70, 37.41, 37.14, 37.06, 36.79, 36.05, 34.37, 34.21, 34.02, 33.94, 33.61, 33.11, 29.80, 29.47, 28.15, 26.81, 26.35, 24.78, 23.73, 21.93, 19.11, 12.37 |
| 39 | $^1$H NMR (250 MHz, CD$_3$OD): δ (ppm) = 3.79 (m, 1H), 3.38 (m, 4H), 2.83-2.60 (m, 13H), 2.46-0.95 (m, 50H), 0.70 (s, 3H). $^{13}$C NMR (63 MHz, CD$_3$OD): δ (ppm) = 175.42, 69.06, 59.47, 57.48, 51.66, 48.99, 48.93, 45.76, 43.83, 43.74, 41.62, 41.20, 40.97, 40.76, 37.74, 37.19, 36.82, 36.10, 34.18, 33.48, 33.23, 31.14, 30.25, 29.89, 29.49, 28.43, 24.80, 23.79, 21.94, 19.23, 14.83, 13.46, 12.40 |
| 40 | $^1$H NMR (250 MHz, CD$_3$OD): δ (ppm) = 4.06 (m, 1H), 3.79 (m, 1H), 3.53 (m, 1H), 2.88-2.61 (m, 12H), 2.49-0.95 (m, 57H), 0.70 (s, 3H). $^{13}$C NMR (63 MHz, CD$_3$OD): δ (ppm) = 175.31, 69.06, 59.45, 57.51, 51.71, 50.68, 48.95, 48.43, 47.13, 45.71, 43.85, 43.67, 41.21, 40.97, 40.72, 37.39, 37.28, 37.13, 36.79, 36.04, 34.21, 33.56, 33.40, 33.16, 31.12, 30.12, 29.78, 28.13, 24.79, 23.71, 21.93, 21.28, 21.10, 19.21, 12.36 |
| 42 | $^1$H NMR (250 MHz, CD$_3$OD): δ (ppm) = 3.97-3.91 (m, 2H), 2.78-2.49 (m, 13H), 2.25-0.95 (m, 51H), 0.71 (s, 3H). $^{13}$C NMR (63 MHz, CD$_3$OD): δ (ppm) = 175.93, 74.13, 59.15, 53.41, 52.83, 49.35, 48.25, 47.75, 46.14, 43.96, 42.41, |

TABLE II-continued

The chemical structures synthesized were all confirmed by proton ($^1$H) and/or carbon ($^{13}$C) NMR analysis in deuterated chloroform $CDCl_3$ or deuterated methanol $CD_3OD$ on a machine of Brüker AC 300 type. The chemical shifts δ are expressed in ppm. The recording frequencies of the nuclei and the references used are as follows:
$^1$H NMR: 300 MHz, $Si(CH_3)_4$
$^{13}$C NMR: 75 MHz, $Si(CH_3)_4$ Ex. Characterization 41.01, 37.55, 37.01, 35.85, 34.95, 34.38, 34.14, 33.53, 30.11, 30.05, 29.98, 28.84, 28.55, 27.91, 27.61, 27.24, 25.02, 24.02, 22.82, 22.76, 17.85, 13.35.

43 $^1$H NMR (250 MHz, $CD_3OD$): δ (ppm) = 3.97-3.91 (m, 2H), 3.79 (m, 1H), 2.83-2.39 (m, 15H), 2.27-0.94 (m, 48H), 0.71 (s, 3H). $^{13}$C NMR (63 MHz, $CD_3OD$): δ (ppm) = 175.93, 74.05, 69.04, 59.40, 53.67, 52.87, 52.77, 48.19, 47.64, 46.02, 43.61, 43.15, 42.41, 41.18, 41.01, 37.08, 36.41, 36.00, 34.41, 33.57, 30.20, 29.71, 28.89, 28.05, 27.83, 26.91, 24.36, 23.46, 22.82, 22.76, 17.90, 13.15.

44 $^1$H NMR (250 MHz, $CD_3OD$): δ (ppm) = 3.80 (m, 1H), 3.41-3.35 (m, 4H), 2.80-2.53 (m, 13H), 2.43-0.96 (m, 50H), 0.70 (s, 3H). $^{13}$C NMR (63 MHz, $CD_3OD$): δ (ppm) = 175.41, 68.97, 59.41, 57.50, 53.29, 52.77, 51.69, 45.66, 43.82, 43.75, 43.46, 41.62, 41.18, 40.91, 40.74, 37.17, 36.68, 35.93, 34.19, 33.23, 31.19, 29.46, 29.21, 27.40, 26.48, 24.77, 23.66, 21.93, 19.24, 14.84, 13.47, 12.41.

45 $^1$H NMR (250 MHz, $CD_3OD$): δ (ppm) = 3.94 (m, 1H), 3.80 (m, 1H), 2.83-2.57 (m, 13H), 2.27-0.93 (m, 45H), 0.69 (s, 3H). $^{13}$C NMR (63 MHz, $CD_3OD$): δ (ppm) = 175.89, 69.06, 59.41, 57.64, 57.53, 57.49, 56.98, 54.03, 51.77, 44.82, 43.85, 43.53, 42.43, 41.24, 41.20, 40.95, 39.99, 37.05, 36.71, 35.95, 34.41, 34.27, 33.56, 29.45, 27.67, 24.74, 23.60, 22.80, 22.73, 21.90, 19.07, 12.34.

46 $^1$H NMR (250 MHz, $CD_3OD$): δ (ppm) = 3.94 (m, 1H), 3.79 (m, 1H), 2.83-2.37 (m, 15H), 2.24-0.95 (m, 49H), 0.69 (s, 3H). $^{13}$C NMR (63 MHz, $CD_3OD$): δ (ppm) = 175.77, 69.01, 59.56, 57.47, 53.55, 52.83, 51.68, 46.23, 43.81, 43.68, 42.38, 41.13, 40.94, 37.67, 37.22, 37.03, 36.81, 36.11, 34.33, 34.19, 33.54, 30.61, 29.46, 28.40, 27.38, 24.78, 23.80, 22.86, 22.79, 21.94, 19.13.

47 $^1$H NMR (250 MHz, $CD_3OD$): δ (ppm) = 3.79 (m, 1H), 3.61 (m, 1H), 2.80-2.47 (m, 13H), 2.21-0.95 (m, 57H), 0.69 (s, 3H). $^{13}$C NMR (63 MHz, $CD_3OD$): δ (ppm) = 175.88, 69.09, 59.57, 57.54, 53.56, 52.85, 51.71, 49.76, 46.22, 43.84, 43.71, 41.13, 40.97, 37.19, 37.05, 36.82, 36.07, 34.37, 34.22, 34.02, 33.94, 33.60, 30.60, 29.47, 28.36, 27.34, 26.81, 26.34, 24.77, 23.73, 21.94, 19.10, 12.36

48 $^1$H NMR (250 MHz, $CD_3OD$): δ (ppm) = 3.94 (m, 1H), 3.47 (m, 1H), 2.89-2.52 (m, 13H), 2.37-0.96 (m, 50H), 0.71 (s, 3H). $^{13}$C NMR (63 MHz, $CD_3OD$): δ (ppm) = 175.88, 72.05, 59.99, 57.67, 56.71, 53.38, 52.84, 46.23, 44.94, 44.66, 44.42, 42.43, 40.96, 40.82, 38.80, 36.98, 35.75, 34.40, 33.60, 29.84, 28.10, 24.25, 22.81, 22.75, 19.21, 12.79

49 $^1$H NMR (250 MHz, $CD_3OD$): δ (ppm) = 3.94 (m, 1H), 2.97-2.50 (m, 12H), 2.25-0.86 (m, 53H), 0.69 (s, 3H). $^{13}$C NMR (63 MHz, $CD_3OD$): δ (ppm) = 175.87, 59.16, 58.08, 57.63, 53.52, 53.31, 52.85, 46.12, 44.07, 43.92, 43.84, 42.43, 41.99, 41.66, 40.89, 37.36, 37.20, 36.98, 36.33, 36.23, 34.37, 33.90, 33.52, 29.62, 29.43, 27.79, 27.10, 25.41, 24.22, 22.81, 22.75, 22.10, 19.05, 12.66

50 $^1$H NMR (250 MHz, $CD_3OD$): δ (ppm) = 4.05 (m, 1H), 3.80 (m, 1H), 3.53 (m, 1H), 2.80-2.61 (m, 13H), 2.45-0.95 (m, 58H), 0.70 (s, 3H). $^{13}$C NMR (63 MHz, $CD_3OD$): δ (ppm) = 175.28, 69.07, 59.45, 57.47, 51.67, 50.62, 50.52, 48.89, 48.35, 47.11, 45.71, 43.84, 43.68, 41.19, 40.96, 40.72, 37.56, 37.25, 36.85, 36.79, 36.09, 35.83, 34.19, 33.54, 33.38, 33.21, 29.96, 29.54, 28.30, 24.79, 23.75, 21.93, 21.30, 21.12, 19.23, 12.39

51 $^1$H NMR (250 MHz, $CD_3OD$): δ (ppm) = 3.79 (m, 1H), 3.61 (m, 1H), 2.76-2.62 (m, 13H), 2.49-0.95 (m, 57H), 0.69 (s, 3H). $^{13}$C NMR (63 MHz, $CD_3OD$): δ (ppm) = 175.83, 69.04, 59.43, 57.56, 51.70, 50.55, 50.44, 49.74, 48.32, 45.69, 43.83, 43.63, 41.21, 40.95, 40.69, 37.30, 37.05, 36.76, 36.05, 34.39, 34.21, 34.00, 33.92, 33.60, 32.93, 29.56, 29.46, 28.26, 28.06, 26.80, 26.34, 24.77, 23.71, 21.92, 19.12, 12.38.

52 $^1$H NMR (250 MHz, $CD_3OD$): δ (ppm) = 3.94 (m, 1H), 3.80 (m, 1H), 2.82-2.60 (m, 9H), 2.42-0.96 (m, 50H), 0.69 (s, 3H). $^{13}$C NMR (63 MHz, $CD_3OD$): δ (ppm) = 175.90, 69.00, 59.37, 57.63, 51.76, 50.06, 48.65, 45.53, 43.84, 43.45, 42.44, 41.84, 41.73, 41.23, 40.91, 40.60, 37.09, 36.67, 36.35, 34.42, 34.24, 33.57, 30.03, 29.46, 28.25, 27.70, 27.21, 24.74, 23.55, 22.80, 22.73, 21.89, 19.07, 12.33

53 $^1$H NMR (250 MHz, $CD_3OD$): δ (ppm) = 3.79 (m, 1H), 3.38 (m, 4H), 2.71-2.60 (m, 13H), 2.46-0.95 (m, 48H), 0.70 (s, 3H). $^{13}$C NMR (63 MHz, $CD_3OD$): δ (ppm) = 175.50, 69.12, 59.49, 57.50, 51.67, 49.87, 45.69, 43.84, 43.76, 41.64, 41.21, 40.97, 40.73, 37.79, 37.25, 37.20, 36.83, 36.08, 34.19, 33.66, 33.24, 31.16, 30.49, 29.49, 28.48, 24.79, 23.76, 21.93, 19.20, 14.80, 13.42, 12.36.

54 $^1$H NMR (250 MHz, $CD_3OD$): δ (ppm) = 4.05 (m, 1H), 3.79 (m, 1H), 3.53 (m, 1H), 2.82-2.61 (m, 13H), 2.47-0.95 (m, 54H), 0.70 (s, 3H). $^{13}$C NMR (63 MHz, $CD_3OD$): δ (ppm) = 175.15, 69.00, 59.49, 57.41, 51.63, 50.63, 50.60, 50.17, 48.44, 47.07, 45.72, 43.82, 43.73, 41.18, 40.97, 40.73, 37.79, 37.25, 36.82, 36.12, 34.16, 33.62, 33.50, 33.35, 30.52, 29.57, 28.50, 24.82, 23.86, 21.96, 21.34, 21.17, 19.28, 12.46.

55 $^1$H NMR (250 MHz, $CD_3OD$): δ (ppm) = 3.94 (m, 1H), 3.79 (m, 1H), 2.81-2.48 (m, 9H), 2.40-0.86 (m, 50H), 0.69 (s, 3H). $^{13}$C NMR (63 MHz, $CD_3OD$):

TABLE II-continued

The chemical structures synthesized were all confirmed by proton ($^1$H) and/or carbon ($^{13}$C) NMR analysis in deuterated chloroform CDCl$_3$ or deuterated methanol CD$_3$OD on a machine of Brüker AC 300 type. The chemical shifts δ are expressed in ppm. The recording frequencies of the nuclei and the references used are as follows:
$^1$H NMR: 300 MHz, Si(CH$_3$)$_4$
$^{13}$C NMR: 75 MHz, Si(CH$_3$)$_4$ Ex. Characterization δ (ppm) = 175.79, 69.06, 59.48, 59.45, 57.50, 51.68, 50.69, 50.66, 49.01, 48.40, 47.42, 45.77, 43.83, 43.76, 42.56, 42.39, 41.22, 40.97, 40.79, 37.87, 37.30, 37.06, 36.84, 36.12, 34.35, 34.19, 33.59, 33.56, 31.74, 30.46, 29.46, 28.57, 28.47, 27.97, 24.79, 23.82, 22.86, 22.78, 21.95, 19.13, 12.40.

56 $^1$H NMR (250 MHz, CD$_3$OD): δ (ppm) = 4.06 (m, 1H), 3.80 (m, 1H), 3.53 (m, 1H), 2.80-2.47 (m, 13H), 2.39-0.95 (m, 56H), 0.71 (s, 3H). $^{13}$C NMR (63 MHz, CD$_3$OD): δ (ppm) = 175.29, 69.07, 59.58, 57.47, 53.58, 52.86, 51.70, 50.68, 47.12, 46.26, 43.84, 43.71, 41.16, 40.98, 40.75, 37.26, 36.08, 34.21, 33.53, 33.38, 30.69, 29.56, 28.43, 27.42, 24.79, 23.76, 21.92, 21.29, 21.11, 19.22, 12.38

The abbreviations used for denoting the $^1$H spectrum are as follows:
s = singlet
d = doublet
t = triplet
q = quartet
m = multiplet Among said compounds of formula (I), compounds (1), (2), (5), (13), (15), (33) and (34) or a pharmaceutically acceptable salt thereof, especially the hydrochlorides thereof, are particularly advantageous.

The examples that follow illustrate in detail the preparation of the compounds according to the invention. The structures of the products obtained were confirmed at least by the NMR spectra.

EXAMPLES

All the syntheses were performed with solvents purified according to the usual methods. The commercial reagents are used directly without prior purification.

"Yld" means yield.

Example 1: Preparation of the Compounds of Formula (III) as Defined Above

Example 1.1 N-isopropyldeoxycholamide 1

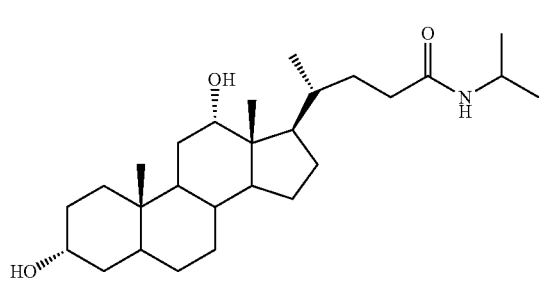

2 g (5.1 mmol) of deoxycholic acid dissolved in 20 mL of THF are placed in a two-necked round-bottomed flask equipped with a magnetic bar. 1.7 equivalents of HOBT (1.36 g, 8.8 mmol) and 1 equivalent of DCC (1.04 g, 5.1 mmol) are then added. 600 µL of isopropylamine (13 mmol) are also added and the mixture is stirred for 24 hours at room temperature. After evaporating off the THF and taking up the residue in 40 mL of CH2Cl2, the precipitate is filtered off and washed with ethyl acetate. The filtrate is concentrated under vacuum and purified by chromatography on silica gel (eluent: ethyl acetate/methanol (9/1)). The desired product 1 is obtained in the form of a white solid (1.9 g).

$^1$H NMR (250 MHz, CDCl$_3$): δ (ppm)=4.17 (m, 2H), 2.39-0.63 (m, 45H). $^{13}$C NMR (63 MHz, CDCl$_3$): δ (ppm) =173.39; 73.17; 71.59; 50.36; 48.93; 48.06; 46.76; 42.09; 41.23; 36.26; 35.96; 35.35; 34.14; 33.68; 33.68; 33.51; 33.44; 31.68; 30.65; 28.47; 27.60; 27.17; 26.19; 25.62; 24.95; 23.75; 23.10; 22.68; 17.31; 12.69. Yld: 79%. C$_{27}$H$_{47}$NO$_3$ Compounds 2-7 were prepared according to the procedure taking the appropriate starting bile acid.

Example 1.2 N-isopropylchenodeoxycholamide 2

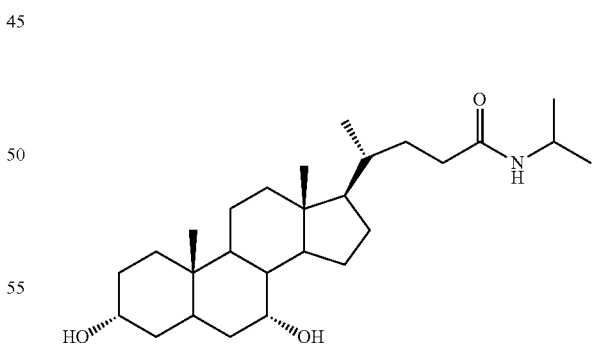

$^1$H NMR (250 MHz, CDCl$_3$): δ (ppm)=3.96 (m, 2H), 3.69 (m, 1H), 3.31 (m, 1H), 2.30-0.75 (m, 41H), 0.50 (s, 3H). $^{13}$C NMR (63 MHz, CDCl$_3$): δ (ppm)=172.88, 72.02, 68.53, 60.46, 55.80, 50.45, 42.69, 41.49, 41.28, 39.83, 39.64, 39.41, 35.47, 35.33, 35.06, 34.60, 33.75, 32.83, 31.82, 30.64, 28.23, 23.71, 22.83, 20.59, 18.42, 14.22, 11.78. Yld: 67%. C$_{27}$H$_{47}$NO$_3$

Example 1.3 N-methylchenodeoxycholamide 3

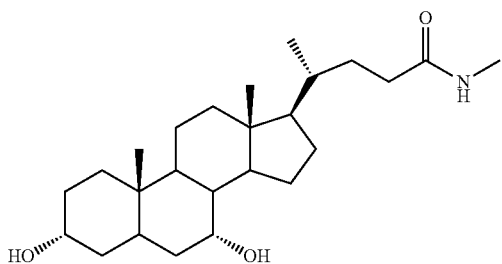

$^1$H NMR (250 MHz, CDCl$_3$): δ (ppm)=3.78 (m, 1H), 3.60 (s, 3H), 3.39 (m, 1H), 2.35-2.06 (m, 3H), 1.98-0.73 (m, 31H), 0.59 (s, 3H). $^{13}$C NMR (63 MHz, CDCl$_3$): δ (ppm) =189.68, 174.82, 71.99, 66.51, 55.78, 51.54, 50.46, 42.69, 41.49, 39.86, 39.64, 39.41, 35.39, 35.08, 34.62, 32.84, 31.02, 30.67, 28.17, 23.71, 22.80, 20.59, 18.28, 11.78. Yld: 57%. C$_{25}$H$_{42}$NO$_3$

Example 1.4 N-isopropyllithocholamide 4

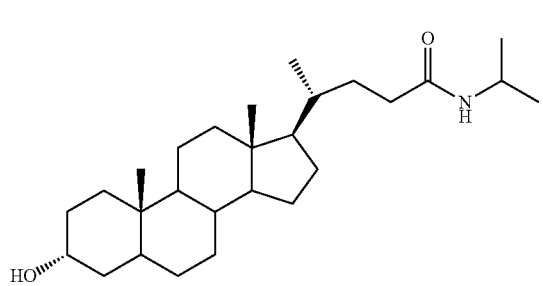

$^1$H NMR (250 MHz, CDCl$_3$): δ (ppm)=4.11-3.40 (m, 3H), 2.11-0.55 (m, 44H). $^{13}$C NMR (63 MHz, CDCl$_3$): δ (ppm) =171.71, 71.87, 58.53, 56.01, 42.76, 42.09, 41.21, 40.43, 40.20, 36.45, 35.88, 35.50, 35.38, 34.58, 34.00, 33.84, 31.81, 30.55, 28.29, 27.20, 26.43, 24.98, 24.22, 23.40, 22.88, 20.84, 18.43, 12.05. Yld: 92%. C$_{27}$H$_{47}$NO$_2$

Example 1.5 N-isopropylcholamide 5

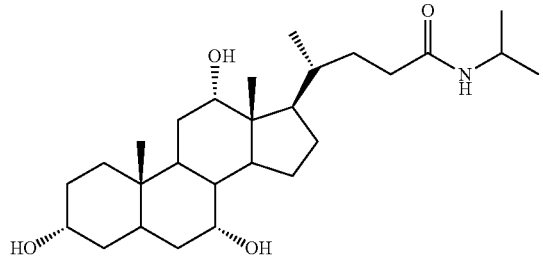

$^1$H NMR (250 MHz, CDCl$_3$): δ (ppm)=4.19-385 (m, 3H), 3.42 (m, 1H), 2.22-0.87 (m, 40H), 0.66 (s, 3H). $^{13}$C NMR (63 MHz, CDCl$_3$): δ (ppm)=173.88, 73.24, 71.86, 68.50, 60.46, 49.07, 46.27, 41.50, 41.33, 39.33, 35.35, 34.78, 34.86, 33.81, 33.06, 31.78, 30.18, 28.01, 27.57, 26.22, 24.91, 23.26, 22.63, 22.39, 21.09, 17.41, 14.20, 12.40 Yld: 83%. C$_{27}$H$_{47}$NO$_4$

Example 1.6 N-isopropylursodeoxycholamide 6

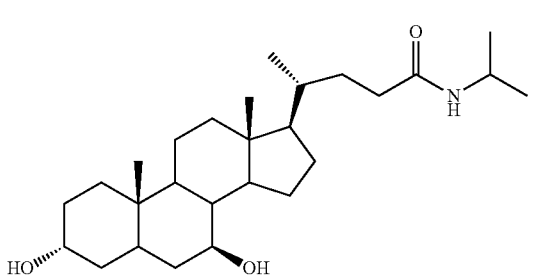

$^1$H NMR (250 MHz, CDCl$_3$): δ (ppm)=4.01-3.92 (m, 1H), 3.59-3.33 (m, 2H), 2.20-0.79 (m, 41H), 0.52 (s, 3H). $^{13}$C NMR (63 MHz, CDCl$_3$): δ (ppm)=173.72, 71.38, 71.35, 55.69, 54.78, 43.68, 43.51, 42.14, 41.51, 40.09, 39.24, 37.14, 36.91, 35.42, 34.93, 34.01, 33.69, 31.97, 30.15, 28.66, 26.87, 25.51, 24.84, 23.38, 22.67, 21.16, 18.45, 12.07. Yld: 70%. C$_{27}$H$_{47}$NO$_3$

Example 1.7 N,N-diethylchenodeoxycholamide 7

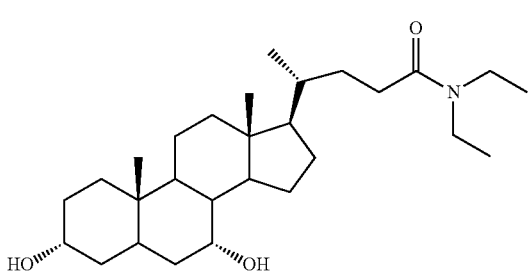

$^1$H NMR (250 MHz, CDCl$_3$): δ (ppm)=4.03 (m, 1H), 3.76-3.57 (m, 2H), 3.37-3.22 (m, 5H), 2.31-0.83 (m, 38H), 0.59 (s, 3H). $^{13}$C NMR (63 MHz, CDCl$_3$): δ (ppm)=173.38, 72.36, 68.85, 67.57, 60.94, 56.44, 50.94, 43.16, 42.55, 42.07, 40.58, 40.21, 39.93, 36.13, 35.92, 35.56, 35.20, 33.33, 32.08, 31.13, 30.47, 28.75, 24.19, 23.35, 21.57, 21.13, 19.07, 14.96, 14.71, 13.61, 12.30. Yld: 70%. C$_{28}$H$_{49}$NO$_3$

Example 2: Preparation of the Compounds of Formula (II) as Defined Above

Example 2.1 3-oxo-N-isopropyldeoxycholamide 8

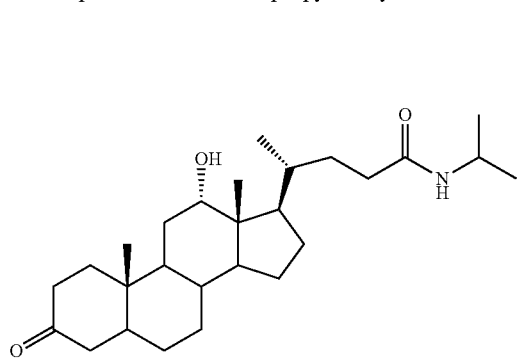

2 g (5 mmol) of N-isopropyldeoxycholamide 1 dissolved in 40 mL of toluene and 30 mL of acetone are placed in a two-necked round-bottomed flask equipped with a magnetic bar and on which is mounted Dean-Stark equipment. 2.2 equivalents of aluminum tri-tert-butoxide (2.7 g, 11 mmol) are then added. The mixture is maintained at the reflux point of toluene for 8 hours. After cooling, the mixture is washed three times with 30 mL of 2N sulfuric acid and then with 30 mL of water. After drying over anhydrous sodium sulfate and filtering, the filtrate is evaporated under vacuum. The crude product thus obtained is purified by chromatography on silica gel (eluent: ethyl acetate). The desired product 8 is obtained in the form of a white solid. $^1$H NMR (250 MHz, CDCl$_3$): δ (ppm)=4.09-4.01 (m, 2H), 2.78-0.68 (m, 43H). $^{13}$C NMR (63 MHz, CDCl$_3$): δ (ppm)=213.51, 172.55, 72.85, 48.06, 47.24, 46.52, 44.23, 42.28, 41.16, 37.08, 36.82, 35.63, 35.12, 34.34, 33.74, 33.69, 31.61, 28.87, 27.44, 26.48, 25.41, 23.52, 22.78, 22.75, 22.32, 17.42, 12.72. Yld: 49%. C$_{27}$H$_{45}$NO$_3$ Compounds 9-12 were all produced according to the same procedure as that developed for the synthesis of compound 8 described above, taking the appropriate starting diol (compounds 2, 5-7) prepared previously.

Example 2.2 3-oxo-N-isopropylchenodeoxycholamide 9

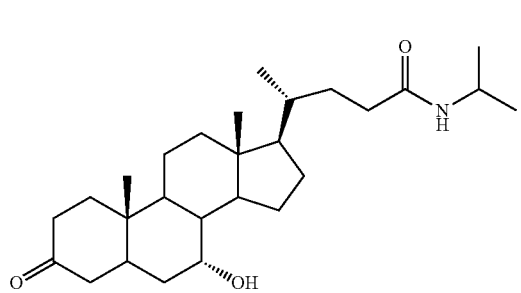

$^1$H NMR (250 MHz, CDCl$_3$): δ (ppm)=4.07 (m, 1H), 3.91 (m, 1H), 2.44-0.64 (m, 43H). $^{13}$C NMR (63 MHz, CDCl$_3$): δ (ppm)=213.40, 172.57, 68.28, 55.79, 50.25, 45.59, 43.19, 42.65, 41.15, 39.46, 39.29, 36.93, 36.77, 35.41, 35.25, 33.82, 33.69, 33.16, 31.69, 23.60, 22.79, 22.76, 21.88, 20.91, 18.34, 11.73. Yld: 58%. C$_{27}$H$_{45}$NO$_3$

Example 2.3 3-oxo-N-isopropylcholamide 10

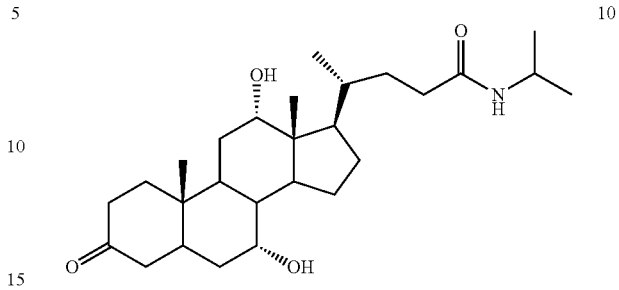

$^1$H NMR (250 MHz, CDCl$_3$): δ (ppm)=3.99-3.86 (m, 3H), 2.41-0.62 (m, 42H). $^{13}$C NMR (63 MHz, CDCl$_3$): δ (ppm)=213.74, 173.30, 72.97, 68.97, 46.55, 46.39, 45.37, 43.01, 41.55, 41.08, 39.11, 36.68, 36.54, 35.35, 34.82, 33.93, 32.99, 31.41, 28.29, 27.51, 26.70, 23.14, 22.54, 21.38, 17.20, 12.34. Yld: 58%. C$_{27}$H$_{45}$NO$_4$

Example 2.4 3-oxo-N-isopropylursodeoxycholamide 11

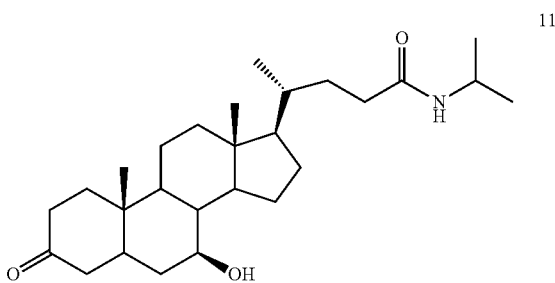 [SMILES: CC(C)NC(=O)CC[C@@H](C)[C@H]1CCC2C3C(CC[C@@]21C)[C@@]1(C)CCC(=O)CC1C[C@@H]3O]

$^1$H NMR (250 MHz, CDCl$_3$): δ (ppm)=4.07 (m, 1H), 3.58 (m, 1H), 2.56-0.67 (m, 43H). $^{13}$C NMR (63 MHz, CDCl$_3$): δ (ppm)=212.12, 172.65, 70.58, 55.61, 54.87, 44.31, 43.64, 43.20, 43.04, 41.13, 39.90, 39.27, 36.93, 36.28, 36.15, 35.27, 34.30, 33.67, 31.71, 28.53, 26.72, 22.69, 22.66, 22.57, 21.54, 18.40, 12.04. Yld: 67%. C$_{27}$H$_{45}$NO$_3$

Example 2.5 3-oxo-N,N-diethylchenodeoxycholamide 12

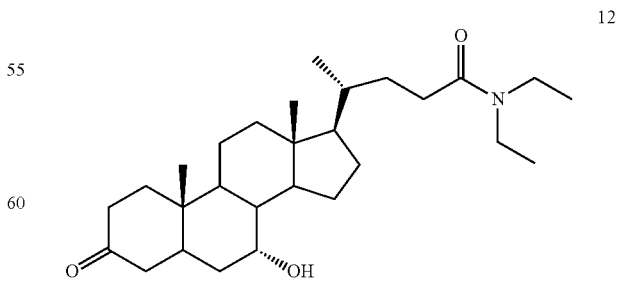

$^1$H NMR (250 MHz, CDCl$_3$): δ (ppm)=3.89 (m, 1H), 3.29 (m, 4H), 2.43-0.67 (m, 42H). $^{13}$C NMR (63 MHz, CDCl$_3$): δ (ppm)=213.48, 172.63, 68.08, 55.85, 50.21, 45.59, 43.25, 42.57, 41.90, 39.97, 39.43, 39.29, 36.90, 36.77, 35.52, 35.22, 33.83, 33.10, 31.42, 29.82, 28.14, 23.57, 21.86, 20.90, 18.43, 14.34, 13.01, 11.71. Yld: 65%. $C_{28}H_{47}NO_3$ Compounds 13 and 14 were produced from N-methylchenodeoxycholamide 3 and N-isopropyllithocholamide 4, respectively, according to the same procedure as that used for the synthesis of compound 8 described above, with the exception of the purification conditions by chromatography on silica gel of the crude products, which were modified (eluent: ethyl acetate/petroleum ether (1/1)).

Example 2.6 3-oxo-N-methylchenodeoxycholamide 13

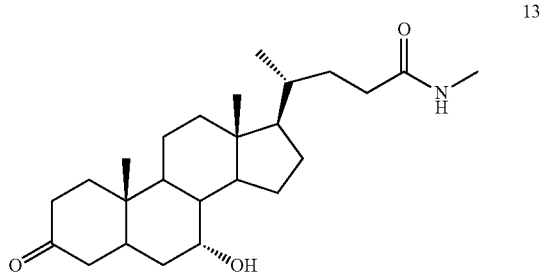 [SMILES: CNC(=O)CC[C@@H](C)[C@H]1CCC2C3C(CC[C@@]21C)[C@@]1(C)CCC(=O)CC1C[C@H]3O]

$^1$H NMR (250 MHz, CDCl$_3$): δ (ppm)=3.79 (m, 1H), 3.54 (s, 3H), 2.34-0.58 (m, 37H). $^{13}$C NMR (63 MHz, CDCl$_3$): δ (ppm)=213.33, 174.42, 67.69, 55.44, 51.18, 49.90, 45.30, 42.99, 42.28, 39.17, 39.02, 36.60, 36.52, 35.00, 34.96, 33.63, 32.83, 30.61, 27.84, 23.26, 21.61, 20.65, 17.95, 11.45. Yld: 42%. $C_{25}H_{41}NO_3$ Example 2.7 3-oxo-N-isopropyllithocholamide 14

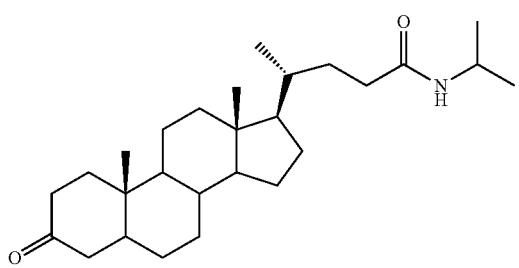

$^1$H NMR (250 MHz, CDCl$_3$): δ (ppm)=4.06 (m, 1H), 2.67-0.65 (m, 44H). $^{13}$C NMR (63 MHz, CDCl$_3$): δ (ppm)=213.44, 172.55, 56.32, 55.93, 44.23, 42.66, 42.26, 41.06, 40.58, 39.94, 37.12, 36.90, 35.38, 34.77, 33.70, 31.69, 28.11, 26.50, 25.65, 24.05, 22.74, 22.71, 22.55, 21.08, 18.30, 11.96. Yld: 37%. $C_{27}H_{45}NO_2$ Example 3: Preparation of the Compounds of Formula (I)

The compounds according to the invention were all prepared by reductive amination of the ketone precursors prepared previously in example 2 (compounds 8-14) in the presence of the appropriate polyamine chain.

Example 3.1: Preparation of Compound (1)

100 mg of 3-oxo-N-isopropyldeoxycholamide 8 (0.23 mmol) are dissolved in 7 mL of methanol in a three-necked round-bottomed flask equipped with a magnetic stirrer. 3 equivalents of titanium tetraisopropoxide (205 μL, 0.7 mmol) and 2 equivalents of norspermine (95 μL, 0.46 mmol) are then added. After stirring for 12 hours at room temperature, the flask is placed in an ice bath and 4 equivalents of sodium borohydride (35 mg, 0.92 mmol) are added with stirring. After stirring for 2 hours and warming to room temperature, 300 μL of water are added to complete the reaction. After stirring for a further 1 hour, the mixture is filtered through Celite, rinsed with aqueous ammonia and then with methanol, and evaporated under vacuum. The crude product thus obtained is purified by chromatography on silica gel (eluent: dichloromethane/methanol/aqueous ammonia (7/3/1)). Compound (1) is obtained in the form of a yellow oil. Yld: 40%. $C_{36}H_{69}N_5O_2$ Example 3.2: Preparation of Compounds (2), (25), (3), (20) and (30)

Compounds (2), (25), (3), (20) and (30) were prepared according to the same procedure developed for the synthesis of compound (1) using 3-oxo-N-isopropyldeoxycholamide 8 as starting precursor and taking the appropriate polyamine chain.

Compound (2) is obtained in a yield of 36% ($C_{33}H_{62}N_4O_2$). Compounds (25), (3), (20) and (30) are obtained in respective yields of 70% ($C_{34}H_{64}N_4O_2$), 58% ($C_{37}H_{69}N_5O_2$), 43% ($C_{37}H_{73}N_7O_2$) and 38% ($C_{37}H_{71}N_5O_2$).

Example 3.3: Preparation of Compounds (31), (4), (5), (26), (6) and (21)

Compounds (31), (4), (5), (26), (6) and (21) were prepared according to the same procedure developed for the synthesis of compound (1) using 3-oxo-N-isopropylcholamide 10 as starting precursor and taking the appropriate polyamine chain.

Compound (31) is obtained in a yield of 37% ($C_{37}H_{71}N_5O_3$). Compounds (31), (4), (5), (26), (6) and (21) are obtained in respective yields of 38% ($C_{36}H_{69}N_5O_3$), 47% ($C_{33}H_{62}N_4O_3$), 24% ($C_{34}H_{64}N_4O_3$), 40% ($C_{37}H_{69}N_5O_3$) and 32% $C_{37}H_{73}N_7O_3$.

Example 3.4: Preparation of Compounds (32), (7), (8), (27), (9) and (22)

Compounds (32), (7), (8), (27), (9) and (22) were prepared according to the same procedure developed for the synthesis of compound (1) using 3-oxo-N-isopropylchenodeoxycholamide 9 as starting precursor and taking the appropriate polyamine chain.

Compound (32) is obtained in a yield of 51% ($C_{37}H_{71}N_5O_2$). Compounds (7), (8), (27), (9), (6) and (22) are obtained in respective yields of 20% ($C_{36}H_{69}N_5O_2$), 55% ($C_{33}H_{62}N_4O_2$), 65% ($C_{34}H_{64}N_4O_2$), 15% ($C_{37}H_{69}N_5O_2$) and 26% ($C_{37}H_{73}N_7O_2$).

Example 3.5: Preparation of Compounds (33), (10), (11) and (12)

Compounds (33), (10), (11) and (12) were prepared according to the same procedure developed for the synthesis of compound (1) using 3-oxo-N-methylchenodeoxycholamide 13 as starting precursor and taking the appropriate polyamine chain.

Compound (33) is obtained in a yield of 36% ($C_{35}H_{67}N_5O_2$). Compounds (10), (11) and (12) are obtained in respective yields of 58% ($C_{34}H_{65}N_5O_2$), 51% ($C_{31}H_{58}N_4O_2$) and 48% ($C_{35}H_{65}N_5O_2$).

Example 3.6: Preparation of Compounds (34) and (13)

Compounds (34) and (13) were prepared according to the same procedure developed for the synthesis of compound (1) using 3-oxo-N,N-diethylchenodeoxycholamide 12 as starting precursor and taking the appropriate polyamine chain.

Compound (34) is obtained in a yield of 44% ($C_{38}H_{73}N_5O_2$) and compound (13) is obtained in a yield of 58% ($C_{34}H_{64}N_4O$).

Example 3.7: Preparation of Compounds (35), (14), (15), (28), (16) and (23)

Compounds (35), (14), (15), (28), (16) and (23) were prepared according to the same procedure developed for the synthesis of compound (1) using 3-oxo-N-isopropylursodeoxycholamide 11 as starting precursor and taking the appropriate polyamine chain.

Compound (35) is obtained in a yield of 36% ($C_{37}H_{71}N_5O_2$). Compounds (14), (15), (28), (16) and (23) are obtained in respective yields of 44% ($C_{36}H_{69}N_5O_2$), 34% ($C_{33}H_{62}N_4O_2$), 30% ($C_{34}H_{64}N_4O_2$), 53% ($C_{37}H_{69}N_5O_2$) and 38% ($C_{37}H_{73}N_7O_2$).

Example 3.8: Preparation of Compounds (36), (17), (18), (29), (19) and (24)

Compounds (36), (17), (18), (29), (19) and (24) were prepared according to the same procedure developed for the synthesis of compound (1) using 3-oxo-N-isopropyllithocholamide 14 as starting precursor and taking the appropriate polyamine chain.

Compound (36) is obtained in a yield of 28% ($C_{37}H_{71}N_5O$). Compounds (17), (18), (29), (19) and (24) are obtained in respective yields of 22% ($C_{36}H_{69}N_5O$), 32% ($C_{33}H_{62}N_4O$), 39% ($C_{34}H_{64}N_4O$), 18% ($C_{37}H_{69}N_5O$) and 45% ($C_{37}H_{73}N_7O$).

Example 4: Intrinsic Antibacterial Activities of the Compounds of Formula (I)

1) Preparation of the Preculture
Two tubes were prepared:
A negative control (2 mL of sterile culture medium)
A positive control (1940 µL of culture medium+40 µL of DMSO+20 µL of the bacterial suspension) from a thawed biological strain (the biological strains are stored at −80° C. in glycerol).

The tubes were incubated at 37° C. for 24 hours at 100 rpm.

The microorganisms were handled under a type L2 laboratory fume cupboard and, before any handling, a UV cycle was programmed and only sterile material was used. A test of toxicity of the solvents (methanol, ethanol, DMSO) was performed and these solvents proved to be nontoxic at concentrations of less than or equal to 2%. The chemical compounds to be tested were prepared in a DMSO/methanol mixture (50/50) at a concentration of 5 mg/mL.

2) Preparation of the Microplate for the Determination of the Minimum Inhibitory Concentration (MIC)

After 24 hours of incubation, a measurement of the optical density was taken using a spectrophotometer at 600 nm, collecting 100 µL of the bacterial suspension diluted in 900 µL of the sterile culture medium. This test required the use of a 96-well plate and the required volume of the microbial suspension to be seeded was calculated for an OD corresponding to a value equal to 0.01 in each well. In this plate, the first line corresponded to the negative control (195 µL of sterile culture medium in each well), the second line corresponded to the positive control (seeded culture medium supplemented with 2% of DMSO), and the third line was loaded twice with bacterial suspension; 8 µL of test product were placed in each well. Thereafter, a 0.5 cascade dilution was performed from this line.

The first column served as inhibition control. A sterile filter was then placed on the microplate, allowing the passage of gases but not of contaminants. The microplate was incubated at 37° C. under a humid atmosphere for 24 hours.

NB: The medium used is Mueller-Hinton (MH) medium for bacteria. All the tests were performed in duplicate.

3) Cytotoxicity

Test WST1 was used to measure the cytotoxic activity of the products. This is a colorimetric test which makes it possible to measure the viability and the degree of cell proliferation. It is based on cleavage of the colorless tetrazolium salts WST-1 (4-[3-(4-iodophenyl)-2-(4-nitrophenyl)-2H-5-tetrazolio]-1,3-benzene disulfonate) with mitochondrial dehydrogenases to the yellow-colored formazan derivative, which may be quantified by spectrophotometry at 420-480 nm.

The WST1 test was performed on Chinese hamster ovary cells. The CHO-K1 cells (ATCC, USA) are kept in culture in McCoy's 5A medium supplemented with 10% fetal calf serum, 2 mM of L-glutamine and a mixture of penicillin-streptomycin (100 U/ml: 10 µg/ml). The culture is incubated at 37° C. under an atmosphere enriched in $CO_2$ (5%), and subcultured every two days.

The cells are transferred into 96-well plates (25000 cells/mL) in whole McCoy's 5A medium, and maintained for 24 hours at 37° C. under a humid atmosphere enriched in $CO_2$ (5%). Increasing concentrations of test products are added to the wells in double tests and 8 growth controls containing the cells in the medium alone are included in each series of tests. After 24 hours at 37° C. (5% $CO_2$), the culture medium is removed, the cells are rinsed in phosphate buffer (PBS) and 50 µL of PBS containing 10% of reagent WST1 are added to each well. After 20 minutes of incubation at 37° C., the results are read by spectrophotometry at 450 nm.

The results are expressed in dose-response relationships, modeled by nonlinear regression analysis using the Table-Curve software. The 50% inhibitory concentration ($IC_{50}$) represents the concentration of product that is capable of reducing the cell viability by 50%.

4) Reading of the Results

After incubation, the filter was replaced with a transparent film, and an OD reading was then taken in an iEMS plate spectrophotometer at 620 nm. Calculation of the minimum inhibitory concentration (MIC) was performed.

The results are collated in table III below.

TABLE III

Intrinsic antibacterial activities of the compounds of formula (I)

MIC (µg/mL)

| | Gram-positive bacteria | | | | Gram-negative bacteria | | | | |
|---|---|---|---|---|---|---|---|---|---|
| | S. aureus | | S. intermedius | E. faecalis | E. coli | | P. aeruginosa | | IC$_{50}$ |
| | Human ATCC 25923 | Animal (340) | Animal (1051997) | Human ATCC 29212 | Human ATCC 28922 | Animal (1956) | Human ATCC 27853 | Animal (1051575) | (µg/mL) CHO |
| (1) | 4 | 2 | 0.5 | 8 | 8 | 8 | 8 | 8 | 42 |
| (2) | 4 | 2 | 1 | 14 | 14 | 14 | 28 | 14 | 35 |
| (25) | 7 | 14 | 2 | 14 | 14 | 14 | 28 | 28 | 48 |
| (3) | 15 | 15 | 4 | 124 | 124 | >124 | 124 | 62 | 120 |
| (20) | 8 | 8 | 4 | 8 | 8 | 16 | 32 | 32 | 18 |
| (30) | 8 | 8 | 1 | 15 | 15 | 30 | 4 | 4 | 30 |
| (31) | 4 | 8 | 4 | 8 | 16 | 32 | 64 | 32 | 40 |
| (4) | 8 | 16 | 4 | 32 | 16 | 32 | 64 | 32 | 65 |
| (5) | 8 | 16 | 4 | 16 | 16 | 32 | 64 | 64 | 70 |
| (26) | 28 | 28 | 14 | 56 | 28 | 56 | 112 | 56 | 80 |
| (6) | 16 | 32 | 16 | 32 | 32 | 64 | 218 | 64 | 100 |
| (21) | 17 | 17 | 8 | 30 | 130 | 30 | 130 | 30 | 60 |
| (32) | 7 | 2 | 0.5 | 7 | 15 | 31 | 30 | 15 | 34 |
| (7) | 4 | 2 | 1 | 4 | 15 | 8 | 30 | 15 | 55 |
| (8) | 6 | 3 | 1 | 8 | 14 | 14 | 54 | 27 | 50 |
| (27) | 8 | 8 | 4 | 16 | 16 | 32 | 32 | 128 | 100 |
| (9) | 16 | 8 | 8 | 62 | 15 | 15 | 124 | 62 | 90 |
| (22) | 8 | 8 | 2 | 32 | 32 | 32 | 130 | 65 | 120 |
| (33) | 3.5 | 1 | 0.8 | 14 | 14 | 7 | 7 | 2 | 35 |
| (10) | 7 | 1 | 1 | 14 | 14 | 7 | 28 | 5 | 35 |
| (11) | 6 | 3 | 1 | 13 | 13 | 13 | 12 | 6 | 20 |
| (12) | 8 | 4 | 2 | 15 | 30 | 15 | 60 | 30 | 50 |
| (34) | 4 | 4 | 2 | 2 | 8 | 8 | 16 | 16 | 50 |
| (13) | 2 | 4 | 2 | 2 | 8 | 8 | 16 | 16 | 22 |
| (35) | 16 | 16 | 8 | 64 | 64 | 64 | 32 | 64 | 55 |
| (14) | 16 | 32 | 4 | 128 | 128 | 128 | 64 | 128 | 90 |
| (15) | 28 | 56 | 7 | 112 | 56 | 112 | 56 | 112 | 140 |
| (28) | 28 | 28 | 14 | 56 | 56 | 112 | 112 | 112 | 28 |
| (16) | 60 | 60 | 15 | 120 | 60 | 120 | >120 | >120 | — |
| (23) | 32 | 32 | 16 | 64 | 128 | 128 | 128 | 128 | 115 |
| (36) | 3.75 | 3.75 | 1.87 | 7.5 | 7.5 | 15 | 15 | 30 | 36 |
| (17) | 8 | 8 | 4 | 8 | 16 | 32 | 64 | 32 | 17 |
| (18) | 6 | 3 | 0.8 | 12 | 26 | 3 | 104 | 26 | 20 |
| (29) | 14 | 14 | 7 | 28 | 28 | 28 | 112 | 112 | 6 |
| (19) | 8 | 4 | 4 | 15 | 30 | 30 | 120 | 30 | 12 |
| (24) | 8 | 8 | 4 | 16 | 32 | 64 | 128 | 128 | 35 |
| (42) | 4 | 4 | 1 | 30 | >120 | 30 | 30 | 60 | 40 |
| (43) | 16 | 16 | 8 | 60 | 125 | 60 | 125 | 60 | 38 |
| (44) | 2 | 4 | 2 | n.d. | 15 | 30 | 60 | 60 | 75 |
| (53) | 4 | 4 | 2 | 2 | 60 | 15 | 30 | 15 | 30 |
| (45) | 7 | 4* | 2 | 14 | 110 | 14* | 110 | 28* | 60 |
| (46) | 8 | 2 | 2 | 30 | >120 | 30 | 60 | 120 | 50 |
| (37) | 4 | 2 | 1 | 4 | 15 | 4 | 30 | 15 | 35 |
| (50) | 4 | 2 | 2 | 4 | >130 | 17 | 17 | 17 | 25 |
| (54) | 4 | 4 | 2 | 2 | 125 | 8 | 32 | 16 | 22 |
| (38) | 4 | 4 | 2 | 4 | 30 | 15 | 30 | 30 | 12 |
| (51) | 4 | 2 | 1 | 2 | 105 | 16 | 16 | 16 | 13 |
| (55) | 2 | 4 | 2 | n.d. | 112 | 55 | 14 | 112 | 80 |
| (52) | 7 | 4 | 2 | 14 | 112 | 28 | 56 | 112 | 80 |
| (39) | 2 | 1 | 1 | n.d. | 120 | 4 | 15 | 8 | n.d. |
| (40) | 4 | 2 | 2 | 2 | 32 | 8 | 8 | 8 | n.d. |
| (56) | 4 | 4 | 4 | 2 | 65 | 16 | 130 | 65 | n.d. |
| (47) | 4 | 8 | 8 | 8 | 130 | 32 | 130 | 32 | n.d. |
| (48) | 30 | 15 | 8 | 60 | >120 | 120 | 120 | 120 | 42 |
| (49) | 4 | 4 | 2 | 15 | 120 | 30 | 120 | 60 | 6 |

Example 5: Antibacterial Activities of the Compounds of Formula (I) in Combination with Doxycycline Preparation of the Microplate for the Determination of the Minimum Inhibitory Concentration (MIC) of the Combination of a Compound of Formula (I) and of Doxycycline This method requires the use of a 96-well plate: 100 µL of a liquid culture medium are placed in each well and then seeded with the microbial suspension prepared previously. The required volume to be seeded is calculated for an OD of 0.01, which corresponds to about 5×10$^6$ bacteria in each well. In this plate, the first line corresponds to a negative control (200 µL of sterile culture medium in each well), the second line corresponds to a positive control (100 µL of sterile culture medium+100 µL of the bacterial suspension), and the third line contains 192 µL of culture medium; 8 µL of compound of formula (I) to be tested are placed in each well. Thereafter, a cascade dilution is performed from this line. L of a doxycycline solution (1 mg dissolved in 20 mL) are then added to each well of lines 3 to 8 to obtain a final antibiotic concentration of 2 µg/mL. 92 µL of bacterial suspension are then added to lines 3 to 8. The results are read (the determination of the MIC (2 µg/mL of doxycycline) in the presence of X g/mL of compound of formula (I)) after 24 hours of incubation at 37° C. under a humid atmosphere. After 24 hours of incubation at 37° C., 40 µL of nitro tetrazolium iodide are added to each well to reveal the presence of live bacteria by staining the medium pink.

On the Gram-negative strain of *P. aeruginosa* (PAO1), doxycycline has an MIC of 40 µg/mL.

The results are given in table IV. They indicate the concentration of compounds of formula (I) required to be able to restore the doxycycline activity (2 µg/mL).

TABLE IV

Potentiation of the doxycycline activity at 2 µg/mL in the presence of the compounds of formula (I)

| Compound No. | MIC - *P. aeruginosa* (1051575) µg/mL Content of compound of formula (I) to restore the doxycycline activity (at 2 µg/mL) (µg/mL) |
|---|---|
| (1) | 1 |
| (2) | 0.9 |
| (25) | 2 |
| (3) | 2 |
| (20) | 4 |
| (30) | 1 |
| (31) | 1 |
| (4) | 1 |
| (5) | 1 |
| (26) | 4 |
| (6) | 8 |
| (32) | 1 |
| (7) | 1 |
| (8) | 2 |
| (27) | 2 |
| (9) | 2 |
| (22) | 4 |
| (33) | 1 |
| (10) | 1 |
| (11) | 2 |
| (12) | 8 |
| (34) | 2 |
| (13) | 2 |
| (35) | 2 |
| (14) | 1 |
| (15) | 1 |
| (28) | 7 |
| (36) | 0.5 |
| (17) | 2 |
| (18) | 0.8 |
| (29) | 7 |
| (19) | 8 |
| (24) | 8 |
| (42) | 1 |
| (43) | 1 |
| (44) | 2 |
| (53) | 2 |
| (45) | 7 |
| (46) | 2 |
| (37) | 2 |
| (50) | 2 |
| (54) | 2 |
| (38) | 2 |
| (51) | 2 |
| (55) | 2 |
| (52) | 3.5 |
| (39) | 2 |
| (40) | 2 |
| (56) | 2 |
| (47) | 2 |

TABLE IV-continued

Potentiation of the doxycycline activity at 2 µg/mL in the presence of the compounds of formula (I)

| Compound No. | MIC - *P. aeruginosa* (1051575) µg/mL Content of compound of formula (I) to restore the doxycycline activity (at 2 µg/mL) (µg/mL) |
|---|---|
| (48) | 4 |
| (49) | 4 |

The use of small amounts of compounds of formula (I) makes it possible to restore (to reduce) the concentration of antibiotic required to kill the strain under consideration. Very good synergism of certain compounds with doxycycline is thus observed, thus restoring the activity of this antibiotic at low concentrations of use (2 µg/mL).

In particular, compounds (2), (9), (25) and (36) make it possible to achieve noteworthy synergism when they are administered with doxycycline at 2 µg/mL.

Example 6: Antibacterial Activity of the Compounds of Formula (I) in Combination with Ampicillin, Erythromycin and Chloramphenicol (Bacterial Strain: *P. aeruginosa* 1051575)

The procedure is identical to that indicated in Example 5 above. 8 µL of an antibiotic solution under consideration (1 mg dissolved in 20 mL) are added to obtain a final antibiotic concentration of 2 µg/mL instead of 8 µL of a doxycycline solution.

The results are given in table V. They indicate the concentration of compound of formula (I) required to be able to restore the activity of the antibiotic under consideration.

TABLE V

Potentiation of the activity of the antibiotic under consideration at 2 µg/mL in the presence of the compounds of formula (I)

| | MIC *P. aeruginosa* (1051575) (µg/mL) | | | |
|---|---|---|---|---|
| | compound + ampicillin[2] | compound + erythromycin[3] | compound + chloramphenicol[4] | |
| | 4 µg/mL | 2 µg/mL | 4 µg/mL | 2 µg/mL |
| (2) | 28 | 3* | 0.9 | 0.9 |
| (25) | 56 | 28 | 2 | n.d. |
| (42) | n.d. | 8 | n.d. | 2 |
| (5) | 64 | 32* | 2 | 4 |
| (21) | n.d. | 30 | n.d. | 8 |
| (43) | n.d. | 30 | n.d. | 4 |
| (7) | 15 | 15 | 2 | n.d. |
| (8) | 27 | 27 | 2 | n.d. |
| (27) | 64 | 28 | 1 | 4 |
| (44) | n.d. | 8 | n.d. | 4 |
| (45) | n.d. | 28 | n.d. | 7 |
| (37) | n.d. | 7 | n.d. | 2 |
| (50) | n.d. | 4 | n.d. | 2 |
| (51) | n.d. | 8 | n.d. | 2 |
| (55) | n.d. | 7 | n.d. | 2 |
| (35) | 64 | 32 | 2 | n.d. |
| (15) | 110 | 55 | 2 | 7 |
| (49) | n.d. | 30 | n.d. | 4 |

[2]MIC ampicillin: 200 µg/mL
[3]MIC erythromycin: 200 µg/mL
[4]MIC chloramphenicol: 200 µg/mL
n.d.: not determined Very good synergism of certain compounds with various standard antibiotics, at low concentrations of use, is thus observed.

Example 7: Antifungal Activity of the Compounds of Formula (I)

1) Preparation of the Preculture

Two tubes were prepared:

A negative control (2 mL of sterile Mueller Hinton MH culture medium)

A positive control (1980 µL of culture medium+20 µL of the yeast or fungal suspension) from a thawed biological strain (the biological strains are stored at −80° C. in glycerol).

The tubes were incubated at 37° C. for 24 hours at 100 rpm.

The chemical compounds to be tested were prepared at a concentration of 5 mg/mL (in the form of the hydrochloride in water).

2) Preparation of the Microplate for the Determination of the Minimum Inhibitory Concentration (MIC)

The MIC is obtained by using the cascade microdilution method in sterile 96-well plates. 100 µL of MH culture medium are first placed in each well, and 8 µL of the solution (5 mg/mL) of the test molecule are then added to the first wells. The volume is made up with medium to obtain a total volume of 200 µL in these wells. Serial dilution is then performed by taking 100 µL from the first well, and so on successively from well to well. 100 µL of inoculate containing 2-6×10$^5$ CFU of yeast or fungi are then added to each well. Certain wells are reserved for positive and negative controls. After 24 hours of incubation, the MIC is measured as being the lowest concentration capable of inhibiting the fungal growth.

3) Reading of the Results

After incubation, an optical density (OD) reading was taken in an iEMS plate spectrophotometer at 620 nm. Calculation of the minimum inhibitory concentration (MIC) was performed.

| | IC$_{50}$ (µg/mL) C. albicans | IC$_{50}$ (µg/mL) CHO |
|---|---|---|
| (1) | 0.5 | 33 |
| (4) | 8 | 170 |
| (5) | 4 | 70 |
| (32) | 2 | 13 |
| (8) | 1 | 50 |
| (27) | 2 | 100 |
| (11) | 3 | 20 |
| (34) | 0.5 | 50 |
| (44) | 0.5 | 75 |
| (46) | 1 | 50 |
| (52) | 4 | 48 |
| (40) | 1 | n.d. |
| (56) | 4 | n.d. |
| (47) | 2 | n.d. |
| (35) | 1 | 55 |
| (15) | 14 | 85 |
| (19) | 4 | 12 | n.d.: not determined

These results demonstrate advantageous antifungal activity on two strains for a certain number of compounds of formula (I).

Thus, the compounds of the invention of formula (I), (I'), (Ia), (Ib) or (Ic), and more particularly compounds (1) to (56) or a pharmaceutically acceptable salt thereof, demonstrate antibacterial and antifungal activity. These compounds are useful for treating bacterial infections, especially bacterial infections with Gram-positive bacteria such as infections with *Staphylococcus aureus*, *Staphylococcus intermedius* or *Staphylococcus faecalis* and/or with Gram-negative bacteria such as *Escherichia Coli* and *Pseudonomas aeruginosa*.

The compounds of formula (I), (I'), (Ia), (Ib), (Ic) or (Id), and more particularly compounds (1) to (56) or a pharmaceutically acceptable salt thereof, according to the invention are especially useful for the antibiotic treatment of bacterial infections, especially of strains of Gram-positive or Gram-negative bacteria, in man or animals. By way of example, the compounds according to the invention are useful for treating mammitis, metritis, dental infections, urinary infections, digestive complaints, pyodermatitis or otitis in man or animals. The compounds according to the invention are also useful as a coating preventing bacterial proliferation, for the manufacture of products for destroying biofilms or for preventing their formation. These compounds may be used in a medical device, for example: catheters, prostheses, implants, dialysis machines, surgical instruments, sutures or dressings.

Mammitis or mastitis is inflammation of the udder in mammals, and is a common infection in the rearing of female dairy animals (cows, sheep, goats, buffaloes and camels). It is characterized by the presence in the milk of inflammatory cells (leukocytes) and possibly bacteria. This inflammation can have clinical consequences, with modification of the appearance of the milk, visible inflammation of the udder (tumefaction, pain, edema) and possibly an effect on the general state of health. Usually, the disease remains subclinical with impairment of the composition of the milk and a reduction in production. Mammitis results from infection of the udder with bacteria that are more or less adapted to this biotope. In specialized dairy rearing, mammitis causes substantial economic losses (milk not produced or unsuitable for use, impairment in milk quality) and constitutes a public health risk (pathogenic bacteria and antibiotic residues). Mammitis is caused by the penetration into and then the growth of a bacterium in the mammary gland. The microorganism generally enters via the end of the teat. A mammitis therefore does not generally concern all the quarters of the animal's udder. The main bacteria responsible for mammitis may be grouped into two sets, as a function of their contamination reservoir. Microorganisms which are found at the surface of the udder: Staphylocoques, *Streptococcus agalactiae*, *Streptococcus disgalactiae*, *Streptococcus uberis*. These bacteria are mainly responsible for subclinical mammitis (not detectable with the naked eye) which it is occasionally difficult to cure during lactation, so the drying-up period is exploited to treat the infected quarters with antibiotics. Microorganisms which are found in the environment (litter): for example *Streptococcus uberis*, *Escherichia coli*. These bacteria generally cause clinical mammitis, which may go as far as the rapid death of the animal in the absence of suitable treatment. Mycoplasma-mediated mammitis still causes problems in goat herds, although it has all but disappeared from cattle herds.

Metritis is an inflammation of all of the uterine wall. It may affect various species of domestic mammals (ruminants, horses, pigs, dogs and cats), wild animals and humans. It is caused by a bacterial infection and is almost always observed after an abnormal parturition or a substantial uterine infection. Its gravity ranges from a subclinical infection to a declared disease with fever and reduction of milk production. In the case of cows, metritis can predispose to ketosis, to displacement of the rennet stomach and to other post-partum disorders. It may also result in a temporary or permanent lowering of fertility, and even, in certain cases, to the death of the animal. Metritis is often associated with a contamination of the uterus with the bacterium

*Arcanobacterium pyogenes*, either alone or in conjunction with other pathogenic microorganisms such as: *Fusobacterium necrophorum, Bacteroides* spp. or *Escherichia coli*. Just after calving, the uterus is an ideal environment for bacterial growth. During the first week post-partum, up to 90% of cows are victim to a uterine infection of bacterial origin.

Pyodermatitis is a purulent cutaneous disease, which may be acute or chronic, and local or diffuse. Pyodermatitis is etymologically a skin infection. It is of external origin, caused by a bacterium, generally *Staphylococcus* or *Streptococcus pyogenes*. A pyodermatitis may be circumscribed or generalized. This disease is common in dogs, but may affect all species having similar pathogens, including the human species. In dogs, a pyotraumatic dermatitis is often observed. This is a cutaneous lesion resulting from a compulsion to scratch, nibble and lick a part of the body. Once the lesion is relatively large, a secondary infection with opportunist bacteria may occur, causing the animal to nibble or scratch itself even more. Most of the animals often affected have allergies: particularly animals which are allergic to fleas. However, any cutaneous irritation can cause a pyotraumatic dermatitis.

Periodontal disease or dental infection is a disease which can affect all species, including man. It is the main cause of dental disease in dogs and is common in cats. Although characterized by bad breath, it is often unnoticed by the owner. Its prevention proceeds through regular care, since it can lead to the loss of teeth or even to serious infections. The presence of bacteria in the mouth is normal, but when they grow too quickly, they can lead to the formation of dental plaque. If plaque accumulates and is not removed, gingivitis (inflammation of the gums) may appear. At this stage, the treatment may be completely curative. However, in the absence of treatment, the disease evolves into periodontitis, characterized by a more substantial inflammation of the gums, tartar deposits on the teeth and the disappearance of bone and of the support structures surrounding the tooth. The attack can be dealt with, but is irreversible. Periodontitis may lead to the loss of teeth and the propagation of serious infections in the liver, heart or lungs.

Cystitis, or urinary infection, is a disease which can affect all species, including man. This pathology is particularly common in cats, but is also frequently encountered in dogs. It may be consecutive to local traumas such as urinary stones or infections of exogenous origin.

Digestive complaints, and more particularly those leading to diarrhea, are very common complaints in man and animals, in particular in cats and dogs. These complaints are often due to contaminations and increased bacterial proliferation of aerobic or anaerobic microorganisms, or contamination with protozoans.

Otitis is an inflammation of the auditory canal. Otitis may affect all animal species, and also man. It is an extremely frequent pathology in domestic carnivores, in particular dogs. It may have many origins, some of which will be responsible for recurrent otitis. Several types of bacteria (*Staphylococcus, Pseudomonas*, etc.) and of yeast (*Malassezia*) may grow in the auditory canal, causing the onset of otitis. These otitis attacks are then combined with purulent secretions and a very unpleasant odor.

According to a particular aspect of the invention, the compounds of formula (I) are administered in combination with another antibiotic compound, especially of the beta-lactamine family (penicillins/cephalosporins), aminosides, macrolides, polypeptides, sulfamides, quinolones, nitro-imidazoles, nitrofuran derivatives, benzyl-pyrimidine nucleus derivatives, tetracyclines or phenicols, such as doxycycline or chloramphenicol, penicillin, ampicillin, amoxicillin, cloxacillin, dicloxacillin, oxacillin, nafcillin, cephalexin, cephapirin, cefazolin, ceftiofur, cefoperazone, cefovecin, cefquinome, thimaphenicol, florfenicol, terramycin, erythromycin, spiramycin, tylosin, josamycin, tilmicosin, tulathromycin, gamithromycin, tildipirosin, clindamycin, lincomycin, pirlimycin, tiamulin, valnemulin, oxolinic acid, flumequine, enrofloxacin, danofloxacin, ibafloxacin, marbofloxacin, difloxacin, obifloxacin, pradofloxacin, rifampicin, rifaximin, sulfamethizole, sulfathiazole, sulfadimidine, sulfamethoxazole, sulfadiazine, sulfadimethoxine, sulfamethoxypyridazine, trimethoprim, baquiloprim, metronidazole, dimetridazole, ronidazole, nitrofurantoin, furazolidone or furaltadone. In a particularly advantageous use of the compounds of the invention, synergism is observed during the combined use of the compounds of the invention with antibiotics.

Specifically, it has been observed that when the compounds of formula (I) were combined with another antibiotic compound, for example doxycycline, ampicillin, erythromycin or chloramphenicol on a Gram-negative strain of *Pseudonomas aeruginosa*, synergism was observed, as illustrated in example 5 above. This property makes it possible, for example, to efficiently treat patients with a smaller amount of antibiotic, which can reduce the appearance of resistance to the antibiotics.

The present invention thus also relates to pharmaceutical or veterinary compositions comprising at least one compound chosen from the compounds of formulae (I), (Ia), (Ib), (Ic), (Id) and (Ie) as defined above and compounds (1) to (56) as defined above, or a pharmaceutically acceptable salt thereof, and at least one antibiotic other than an abovementioned compound, more particularly as defined previously, and even more particularly doxycycline.

According to one aspect of the invention, the pharmaceutical or veterinary compositions also comprise a second antibiotic compound, especially of the beta-lactamine family (penicillins/cephalosporins), aminosides, macrolides, polypeptides, sulfamides, quinolones, nitro-imidazoles, nitrofuran derivatives, benzyl-pyrimidine nucleus derivatives, tetracyclines or phenicols.

The present invention also relates to the use of the compounds of formula (I), (I'), (Ia), (Ib), (Ic), (Id) or (Ie) or a compound of formula (1) to (56) or a pharmaceutically acceptable salt thereof, for potentiating the antibiotic activity of antibiotic compounds which may be chosen from the antibiotic compounds mentioned previously.

The compounds in accordance with the invention are also compounds of choice as antibiotic substitutes. The compounds according to the invention afford excellent activity against bacteria, while at the same time preventing the appearance of resistance, which is a major advantage since the problem of the appearance of resistance to conventional antibiotics has become a public health problem. By virtue of their mechanism of action, which is different from that of antibiotics, the compounds of the invention are thus excellent substitutes for antibiotics.

According to another aspect, the compounds of formula (I), (I'), (Ia), (Ib), (Ic) or (Id), and more particularly compounds (1) to (56), or a pharmaceutically acceptable salt thereof, according to the invention are especially useful for combating fungal diseases.

Fungal diseases are generally referred to by the term mycosis. Many types of mycoses exist, which differ by the fungal species in question, the localization of the infection, its acute or chronic nature, the mode of infection, etc. These diseases are, for example, ringworm, candidiasis or onyxis, blastomycosis, aspergillosis, coccidioidomycosis, cryptococcosis and sporotrichosis. They may affect man or animals. The treatments are either local topical treatments or oral-route treatments, depending on the seriousness and the type of attack. Among the fungi frequently involved in mycoses, in particular human mycoses, the ones mainly found are:

"yeasts" (microscopic round fungi), including *Candida, Cryptococcus, Pityrosporum* and *Pneumocystis*, which are responsible, respectively, for candidiasis, cryptococcosis, pityrosporosis and pneumocystosis, "filamentous" fungi, including dermatophytes (which are the cause of dermatophytosis), *Aspergillus* (causing respiratory aspergillosis), etc., and dimorphic fungi (histoplasmosis). The infections caused by *Candida* represent the main cause of fungal infections ranging from mild skin or mucosal infections to serious infections affecting an organ. Fungi of *Aspergillus* type are responsible for the majority of the infections after *Candida*.

According to yet another aspect of the invention, the pharmaceutical or veterinary compositions also comprise a second antiparasitic compound, especially an antimalaria compound.

According to another aspect, the invention provides compounds of formula (I), (I'), (Ia), (Ib), (Ic), (Id) or (Ie) or a compound of formula (1) to (56), or a pharmaceutically acceptable salt thereof, for the use thereof in the treatment of parasitic or viral infections in man or animals, such as malaria, feline immunodeficiency virus (FIV), feline infectious peritonitis (FIP), toxoplasmosis, leishmaniasis, echinococcosis, ehrlichiosis, Rubarth's hepatitis, leptospirosis, Carré's disease, canine parvovirosis, piroplasmosis, kennel cough or whooping cough, dirofilariasis, feline leukemia (FeLV), coryza, typhus or feline panleukopenia. The compounds according to the invention may also be used as antiviral agents.

According to a particular aspect, the compounds of formula (I) are administered in combination with another antimalaria compound. Advantageously, the compounds of formula (I) make it possible to potentiate the activity of the antiparasitic compounds, especially antimalaria compounds.

The present invention also relates to a method for treating a human or an animal suffering from bacterial, fungal, viral or parasitic infections, which comprises at least one step of administering an effective amount of a compound according to any one of the formulae (I), (I'), (Ia), (Ib), (Ic), (Id) and (Ie) as defined above and (1) to (56), or a pharmaceutically acceptable salt thereof.

The present invention also relates to pharmaceutical or veterinary compositions comprising at least one compound chosen from the compounds of formulae (I), (Ia), (Ib), (Ic), (Id) and (Ie) as defined above and compounds (1) to (56) as defined above, or a pharmaceutically acceptable salt thereof, and a pharmaceutically acceptable excipient.

The pharmaceutical or veterinary compositions according to the invention may be in solid or liquid forms intended, for example, for parenteral (intravenous, intramuscular or subcutaneous), oral, general, local, transmucosal, percutaneous, cutaneous, ocular, pulmonary or topical administration.

They are thus in the form of injectable solutions or suspensions or single-dose or multi-dose bottles, in the form of plain or coated tablets, sugar-coated tablets, wafer capsules, gel capsules, pills, cachets, powders, suppositories or rectal capsules, granules or solutions.

Advantageously, the product according to the invention also comprises one or more additional ingredients that are well known to those skilled in the art, especially such as binders, granulating agents, lubricants, colorants, fillers, emulsifiers, minerals, film-forming agents, salts, stabilizers, buffers or vitamins. The stabilizers comprise substances which have a tendency to increase the shelf life of the composition, such as preserving agents, emulsifiers, thickeners, packaging gases, gelling agents, humectants, sequestrants, synergists or stabilizers.

For oral administration, the excipients that may be suitable for use may be cellulose or microcrystalline cellulose derivatives, alkaline-earth metal carbonates, magnesium phosphate, starches, modified starches or lactose for the solid forms.

For injectable use, the formulation may comprise an aqueous solvent, an organic solvent or a mixture of the two or a plant oil, an organic solvent or a mixture of the two. Among the aqueous solvents, water, aqueous solutions, physiological saline and isotonic solutions are the excipients most usually used. Among the plant oils, examples that may be mentioned include palm oil, maize oil, cotton oil, sunflower oil, groundnut oil, olive oil, soybean oil, safflower oil, coconut kernel oil, sesame oil, or semi-synthetic plant oils obtained by fractionation and/or hydrolysis and/or total esterification of natural plant oils, for instance fatty acid triglycerides derived from plant oils, such as caprylic, capric, linoleic or succinic acid triglycerides (sold under the trade names Miglyol® 810, 812, 818, 820, 829), propylene glycol esters of a fatty acid derived from plant oil, for instance propylene glycol esters of caprylic and capric acids (sold under the trade names Miglyol® 840), and also a mixture thereof, and also esters, among which are triacetin (glyceryl triacetate) and ethyl oleate, for example. Among the organic solvents, examples that may be mentioned include benzyl alcohol, ethanol, N-methylpyrrolidone, glycerol-formaldehyde, glycofurol, diethylene glycol monoethyl ether, propylene glycol, and polyethylene glycol, for example PEG 300, PEG 200 and PEG 400. The choice of the vehicle is made so as to form liquid solutions, as a function of its capacity to dissolve the active substance at room temperature without modifying the chemical structure and stability thereof. The chosen vehicle must be biocompatible and suitable for the injectable route. The vehicle will be chosen from polar solvents, apolar aprotic solvents, or a mixture thereof. The liquid injectable composition may also comprise at least one antioxidant chosen from butylhydroxyanisole (BHA), butylhydroxytoluene (BHT), vitamin E and derivatives thereof, propyl gallate, and mixtures thereof.

For transmucosal administration, especially rectal administration, cocoa butter or polyethylene glycol stearates are preferred excipients.

For percutaneous or cutaneous use, especially on the skin, mucous membranes or bodily hair, in particular for pouring solutions of pour-on or spot-on type in veterinary medicine, the usual excipients are aqueous, alcoholic, polar or nonpolar solvents, which promote transcutaneous passage, such as water, benzyl alcohol, plant oils and mineral oils, suspension agents, antioxidants, surfactants, especially a mixture constituted of benzyl alcohol and/or labrasol and/or propylene glycol laurate, as penetrant, may be used.

For ocular use, the appropriate excipients may also be chosen by a person skilled in the art depending on the required specificities.

The dosage may vary within wide limits (0.05 mg to 1000 mg) as a function of the therapeutic indication and of the administration route, and also of the individual's age and weight.

Other uses of the compounds of the invention are envisaged, for example as agents for restricting contaminations, such as formulation in a nasal ointment.

The present invention also relates to the use of at least one compound chosen from a compound of any one of the formulae (I), (I'), (Ia), (Ib), (Ic), (Id) and (Ie) as defined above, and compounds (1) to (56) as defined above, or a pharmaceutically acceptable salt thereof, according to the present invention for the manufacture of a pharmaceutical or veterinary composition for preventing and/or treating a bacterial, fungal, viral or parasitic infection.

The invention claimed is:
1. A compound of formula (I)

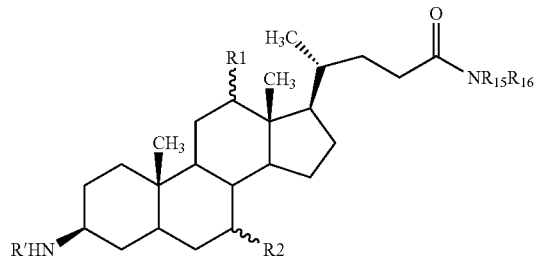

(I)

in which
R1 and R2 independently represent a hydrogen atom, an $SO_3H$ group or a hydroxyl group, R' represents a group —$(CR_aR_b)$—X—$(CR_cR_d)_m$—[Y—$(CR_eR_f)_o]_t$—$NR_9R_{10}$, $R_a$, $R_b$, $R_c$, $R_d$, $R_e$ and $R_f$ independently represent a hydrogen atom, a ($C_1$-$C_8$)alkyl group or a ($C_6$-$C_{10}$)aryl group, X and Y independently represent a group —NR11-, a group —O— or a divalent 5-membered or 6-membered heterocyclic group comprising at least one nitrogen atom, $R_9$ and $R_{10}$ independently represent a hydrogen atom, a ($C_1$-$C_8$)alkyl group or form, together with the nitrogen atom that bears them, a 5-membered or 6-membered heterocyclic group, optionally substituted with one or two groups =O or =S, R11 represents a hydrogen atom, a ($C_1$-$C_8$)alkyl group or a —$(CH_2)_s$—$NH_2$ group, $R_{15}$ and $R_{16}$ independently represent a hydrogen atom, a ($C_1$-$C_8$)alkyl group or a ($C_6$-$C_{10}$)aryl group, n is equal to 2, 3, 4, or 5, m is equal to 2, 3, 4, or 5, o is equal to 2, 3, or 4 and s is equal to 1, 2, 3, or 4, t is equal to 0, 1, 2 or 3, and also the stereoisomers, mixtures of stereoisomers, and/or pharmaceutically acceptable salts thereof.

2. The compound as claimed in claim 1, wherein it is defined by at least one of the following subgroups:

first subgroup of compounds of formula (I) for which $R^1$ and $R^2$ independently represent a hydrogen atom or a hydroxyl group, second subgroup of compounds of formula (I) for which $R_{15}$ and $R_{16}$ independently represent a hydrogen atom or a ($C_1$-$C_4$)alkyl group, third subgroup of compounds of formula (I) for which X is an —NH— group, a 6-membered heterocyclic group including one or two nitrogen atoms, fourth subgroup of compounds of formula (I) for which $R_9$ and $R_{10}$ represent a hydrogen atom, fifth subgroup of compounds of formula (I) for which $R_a$, $R_b$, $R_c$, $R_d$, $R_e$ and $R_f$ represent a hydrogen atom, sixth subgroup of compounds of formula (I) for which Y is a group —NR11-, with R11 representing a hydrogen atom, a ($C_1$-$C_4$)alkyl group or a —$(CH_2)_s$—$NH_2$ group in which s is equal to 1, 2 or 3, seventh subgroup of compounds of formula (I) for which m is equal to 2, 3, 4 or 5, eighth subgroup of compounds of formula (I) for which n is equal to 2, 3, 4 or 5, ninth subgroup of compounds of formula (I) for which m is other than 4, tenth subgroup of compounds of formula (I) for which o is equal to 2 or 3, eleventh subgroup of compounds of formula (I) for which the group —NHR' is chosen from:

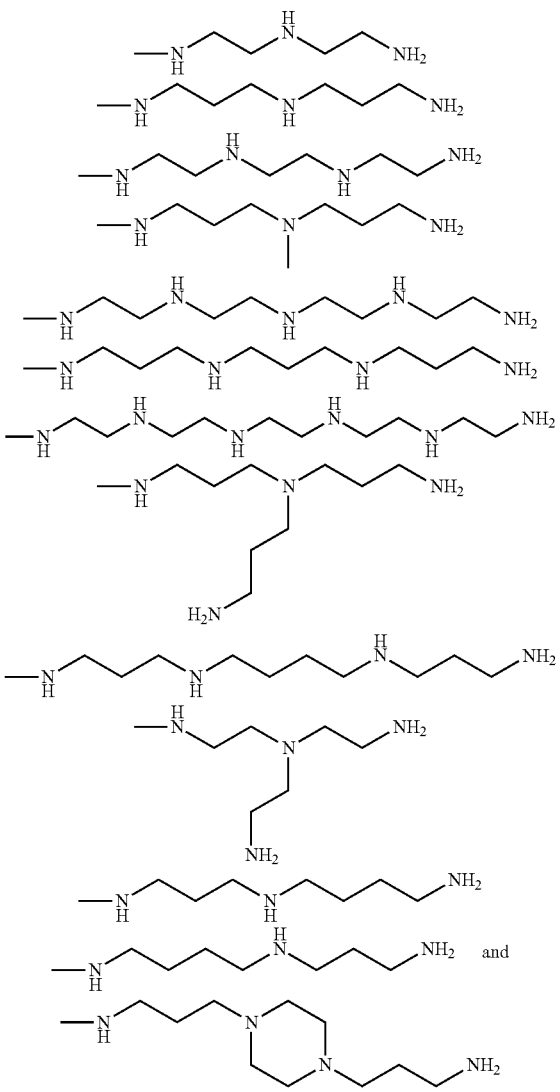

or by the combination of the subgroups as defined above.

3. The compound as claimed in claim 1, wherein it represents formula (I')

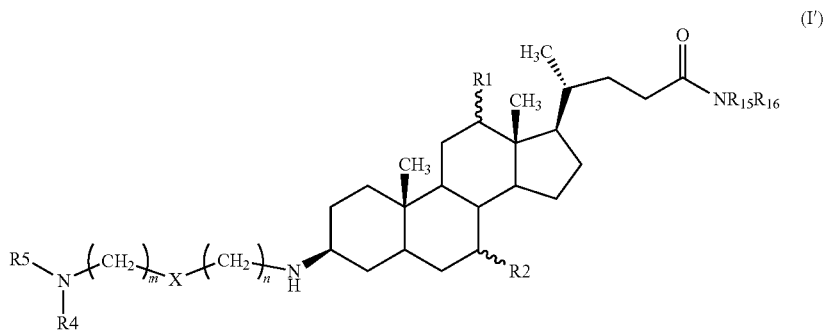

in which
R1 and R2 independently represent a hydrogen atom, an SO$_3$H group or a hydroxyl group,
R$_{15}$ and R$_{16}$ independently represent a hydrogen atom or a (C$_1$-C$_8$)alkyl group,
n represents the integer 2, 3 or 4,
m represents the integer 2, 3 or 4,
X represents a group —NR11- or a divalent 5-membered or 6-membered heterocyclic group comprising one or two nitrogen atoms,
R4 and R11 independently represent a hydrogen atom, a (C$_1$-C$_8$)alkyl group or a —(CH$_2$)$_s$—NH$_2$ group,
R5 represents a hydrogen atom, a —(CH$_2$)$_p$—NH$_2$ group, a —(CH$_2$)$_p$—NH—(CH$_2$)$_q$—NH$_2$ group or a —(CH$_2$)$_p$—NH—(CH$_2$)$_q$—NH—(CH$_2$)$_r$—NH$_2$ group,
p is equal to 2, 3, or 4, q is equal to 2, 3, or 4, r is equal to 2, 3, or 4 and s is equal to 1, 2, 3, or 4,
and also the stereoisomers, mixtures of stereoisomers, and/or pharmaceutically acceptable salts thereof.

4. The compound as claimed in claim 1, wherein R$_{15}$ and R$_{16}$ independently represent a hydrogen atom or a (C$_1$-C$_4$) alkyl group.

5. The compound as claimed in claim 1, wherein n is equal to 2 and m is equal to 3, n is equal to 2 and m is equal to 2, n is equal to 3 and m is equal to 4 or n is equal to 3 and m is equal to 3.

6. The compound as claimed in claim 3, wherein X represents a group —NR11- or a 1,4-piperazinylene group and R4 and R11 independently represent a hydrogen atom, a methyl group or a —(CH$_2$)$_s$—NH$_2$ group, in which s is equal to 2 or 3.

7. The compound as claimed in claim 3, wherein R5 represents a hydrogen atom, a —(CH$_2$)$_p$—NH$_2$ group, a —(CH$_2$)$_p$—NH—(CH$_2$)$_q$—NH$_2$ group or a —(CH$_2$)$_p$—NH—(CH$_2$)$_q$—NH—(CH$_2$)$_r$—NH$_2$ group, in which p is equal to 2 or 3, q is equal to 2 and r is equal to 2.

8. The compound as claimed in claim 1, wherein it alternatively represents formula (Ia)

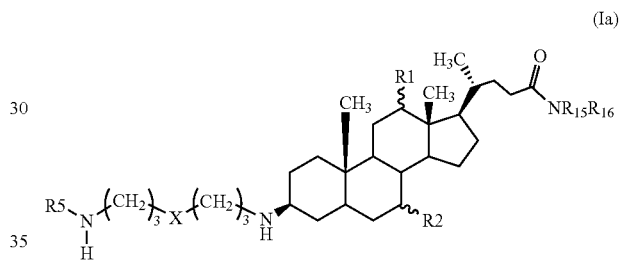

in which
R$_{15}$ and R$_{16}$ independently represent a hydrogen atom or a (C$_1$-C$_8$)alkyl group,
R1 and R2 independently represent a hydrogen atom, an SO$_3$H group or a hydroxyl group,
X represents an —NH— group or a 1,4-piperazinylene group,
R5 represents a hydrogen atom or a —(CH$_2$)$_p$—NH$_2$ group, in which p is equal to 2 or 3,
and also the stereoisomers, mixtures of stereoisomers, and/or pharmaceutically acceptable salts thereof, formula (Ib)

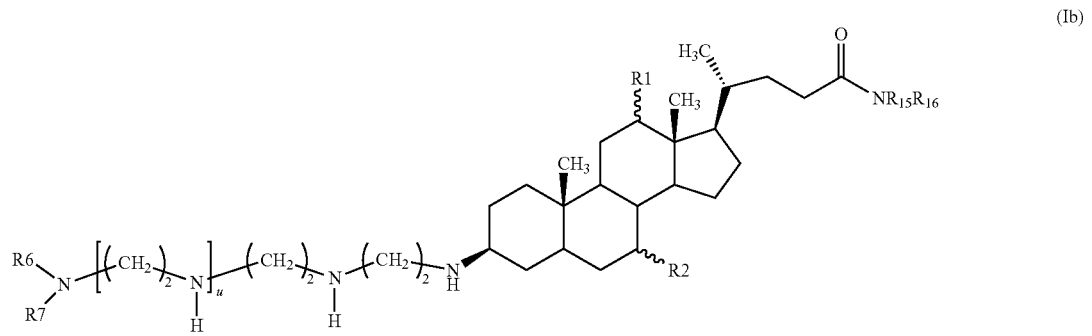

in which $R_{15}$ and $R_{16}$ independently represent a hydrogen atom or a $(C_1-C_8)$alkyl group, R1 and R2 independently represent a hydrogen atom, an $SO_3H$ group or a hydroxyl group, u is equal to 0, 1, 2 or 3, R6 and R7 independently represent a hydrogen atom or a $(C_1-C_8)$alkyl group, and also the stereoisomers, mixtures of stereoisomers, and/or pharmaceutically acceptable salts thereof, formula (Ic)

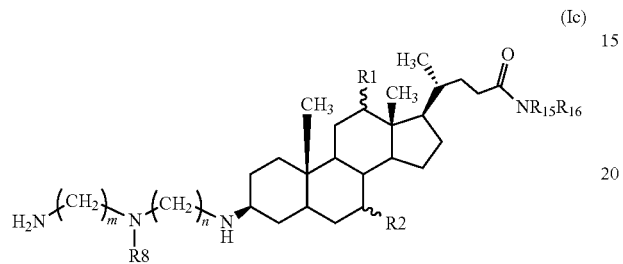

in which $R_{15}$ and $R_{16}$ independently represent a hydrogen atom or a $(C_1-C_8)$alkyl group, R1 and R2 independently represent a hydrogen atom, an $SO_3H$ group or a hydroxyl group, n represents the integer 2, 3 or 4, m represents the integer 2, 3 or 4, and R8 represents a $(C_1-C_8)$alkyl group, or a —$(CH_2)_s$—$NH_2$ group, with s is equal to 1, 2, 3, or 4, and also the stereoisomers, mixtures of stereoisomers, and/or pharmaceutically acceptable salts thereof, formula (Id)

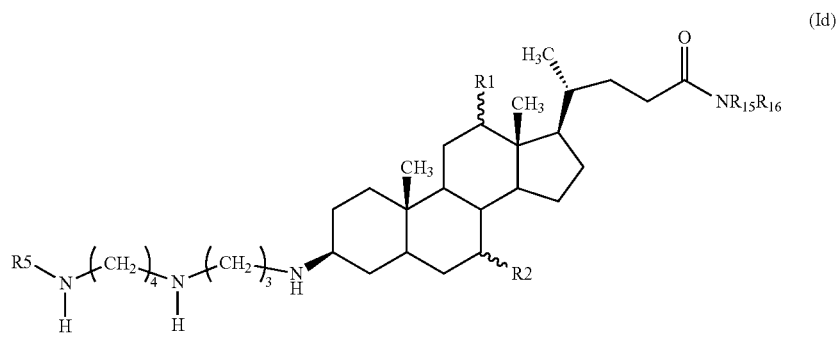

in which $R_{15}$ and $R_{16}$ independently represent a hydrogen atom or a $(C_1-C_8)$alkyl group, R1 and R2 independently represent a hydrogen atom, an $SO_3H$ group or a hydroxyl group, R5 represents a —$(CH_2)_p$—$NH_2$ group, in which p is equal to 2 or 3, and also the stereoisomers, mixtures of stereoisomers, and/or pharmaceutically acceptable salts thereof, or formula (Ie)

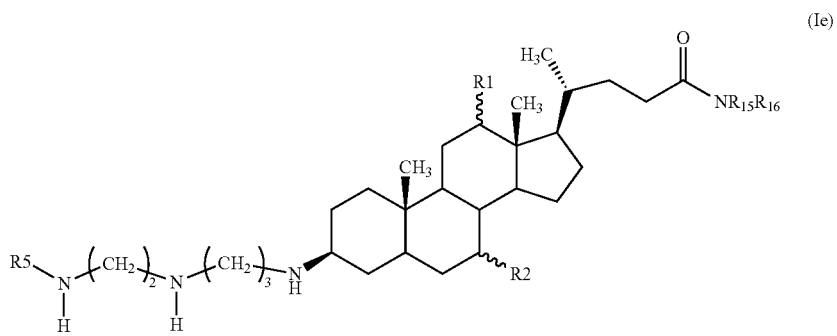

in which

R$_{15}$ and R$_{16}$ independently represent a hydrogen atom or a (C$_1$-C$_8$)alkyl group, R1 and R2 independently represent a hydrogen atom, an SO$_3$H group or a hydroxyl group, R5 represents a —(CH$_2$)$_p$—NH$_2$ group, in which p is equal to 2 or 3, and also the stereoisomers, mixtures of stereoisomers, and/or pharmaceutically acceptable salts thereof.

9. A compound chosen from the following compounds:
(1) 3β-norspermino-N-isopropyldeoxycholamide,
(2) 3β-norspermidino-N-isopropyldeoxycholamide,
(3) 3β-(1,4-bis(3-aminopropyl)piperazine)-N-isopropyldeoxycholamide,
(4) 3β-norspermino-N-isopropylcholamide,
(5) 3β-norspermidino-N-isopropylcholamide,
(6) 3β-(1,4-bis(3-aminopropyl)piperazine)-N-isopropyldeoxycholamide,
(7) 3β-norspermino-N-isopropylchenodeoxycholamide,
(8) 3β-norspermidino-N-isopropylchenodeoxycholamide,
(9) 3β-(1,4-bis(3-aminopropyl)piperazine)-N-isopropyldeoxycholamide,
(10) 3β-norspermino-N-methylchenodeoxycholamide,
(11) 3β-norspermidino-N-methylchenodeoxycholamide,
(12) 3β-(1,4-bis(3-aminopropyl)piperazine)-N-methylchenodeoxycholamide,
(13) 3β-norspermidino-N,N-diethylchenodeoxycholamide,
(14) 3β-norspermino-N-isopropylursodeoxycholamide,
(15) 3β-norspermidino-N-isopropylursodeoxycholamide,
(16) 3β-(1,4-bis(3-aminopropyl)piperazine)-N-isopropylursodeoxycholamide,
(17) 3β-norspermino-N-isopropyllithocholamide,
(18) 3β-norspermidino-N-isopropyllithocholamide,
(19) 3β-(1,4-bis(3-aminopropyl)piperazine)-N-isopropyllithocholamide,
(20) 3β-(pentaethylenehexamine)-N-isopropyldeoxycholamide,
(21) 3β-(pentaethylenehexamine)-N-isopropylcholamide,
(22) 3β-(pentaethylenehexamine)-N-isopropylchenodeoxycholamide,
(23) 3β-(pentaethylenehexamine)-N-isopropylursodeoxycholamide,
(24) N-isopropyl-3β-pentaethylenehexaminedeoxycholamide,
(25) 3β-(1,4-bis(3-aminopropyl)piperazine)-N-isopropyldeoxycholamide,
(26) 3β-(bis(3-aminopropyl)methylamine)-N-isopropylcholamide,
(27) 3β-(bis(3-aminopropyl)methylamine)-N-isopropylchenodeoxycholamide,
(28) 3β-(bis(3-aminopropyl)methylamine)-N-isopropylursodeoxycholamide,
(29) 3β-(bis(3-aminopropyl)methylamine)-N-isopropyllithocholamide,
(30) 3β-spermino-N-isopropyldeoxycholamide,
(31) 3β-spermino-N-isopropylcholamide,
(32) 3β-spermino-N-isopropylchenodeoxycholamide,
(33) 3β-spermino-N-methyldeoxycholamide,
(34) 3β-spermino-N,N-diethylchenodeoxycholamide,
(35) 3β-spermino-N-isopropylursodeoxycholamide,
(36) 3β-spermino-N-isopropyllithocholamide,
(37) 3β-norspermidino-N-diisopropylchenodeoxycholamide,
(38) 3β-norspermidino-N-cyclohexylchenodeoxycholamide,
(39) 3β-norspermino-N,N-diethylchenodeoxycholamide,
(40) 3β-norspermino-N,N-diisopropylchenodeoxycholamide,
(42) 3β-(tris(3-aminopropyl)amine)-N-isopropyldeoxycholamide,
(43) 3β-(tris(3-aminopropyl)amine)-N-isopropylcholamide,
(44) 3β-(tris(3-aminopropyl)amine)-N,N-diethylchenodeoxycholamide,
(45) 3β-(tris(2-aminoethyl)amine)-N-isopropylchenodeoxycholamide,
(46) 3β-(tris(3-aminopropyl)amine)-N-isopropylchenodeoxycholamide,
(47) 3β-(tris(3-aminopropyl)amine)-N-cyclohexylchenodeoxycholamide,
(48) 3β-(tris(3-aminopropyl)amine)-N-isopropylursodeoxycholamide,
(49) 3β-(tris(3-aminopropyl)amine)-N-isopropyllithocholamide,
(50) 3β-spermino-N,N-diisopropylchenodeoxycholamide,
(51) 3β-spermino-N-cyclohexylchenodeoxycholamide,
(52) 3β-spermidino-N-isopropylchenodeoxycholamide,
(53) 3β-(bis(3-aminopropyl)ethylenediamine)-N,N-diethylchenodeoxycholamide,
(54) 3β-(bis(3-aminopropyl)ethylenediamine)-N,N-diisopropylchenodeoxycholamide,
(55) 50/50 mixture of 3β-spermidino-N-isopropylchenodeoxycholamide and of 3β-N-[4'N-(3'-aminopropyl)aminobutyl]amino-N-isopropylchenodeoxycholamide,
(56) 3β-(tris(3-aminopropyl)amine)-N,N-diisopropylchenodeoxy cholamide, or a pharmaceutically acceptable salt thereof.

10. A compound chosen from the following compounds:
(1) 3β-norspermino-N-isopropyldeoxycholamide, (2) 3β-norspermidino-N-isopropyldeoxycholamide, (5) 3β-norspermidino-N-isopropylcholamide, (13) 3β-norspermidino-N,N-diethylchenodeoxycholamide, (15) 3β-norspermidino-N-isopropylursodeoxycholamide, (33) 3β-spermino-N-methyldeoxycholamide, and (34) 3β-spermino-N,N-diethylchenodeoxycholamide.

11. A pharmaceutical or veterinary composition comprising a compound of formula (I) as defined in claim 1 and a pharmaceutically acceptable excipient.

12. The pharmaceutical or veterinary composition according to claim 11, wherein the composition further comprises an antibiotic selected from doxycycline, ampicillin, erythromycin and chloramphenicol.

13. A method for treating a human or an animal suffering from bacterial or fungal infections, which comprises at least one step of administering an effective amount of a compound according to any one of the formula (I) as defined in claim 1.

14. A method for potentiating the antibiotic activity of antibiotic compounds which may be chosen from the antibiotic compounds selected from ampicillin, erythromycin, and chloramphenicol, which comprises at least one step of administering an effective amount of a compound according to formula (I), wherein formula (I) comprises:

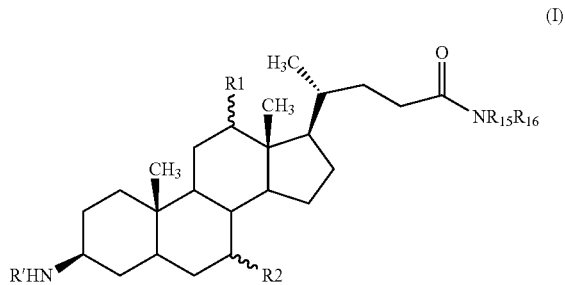 (I)

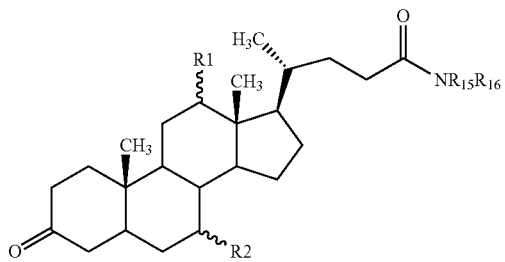 (II)

in which

R1 and R2 independently represent a hydrogen atom, an $SO_3H$ group or a hydroxyl group, R' represents a group —$(CR_aR_b)_n$—X—$(CR_cR_d)_m$—$[Y—(CR_eR_f)_o]_t$—$NR_9R_{10}$, $R_a$, $R_b$, $R_c$, $R_d$, $R_e$ and $R_f$ independently represent a hydrogen atom, a ($C_1$-$C_8$)alkyl group or a ($C_6$-$C_{10}$)aryl group, X and Y independently represent a group —$NR_{11}$—, a group —O— or a divalent 5-membered or 6-membered heterocyclic group comprising at least one nitrogen atom, $R_9$ and $R_{10}$ independently represent a hydrogen atom, a ($C_1$-$C_8$)alkyl group or form, together with the nitrogen atom that bears them, a 5-membered or 6-membered heterocyclic group, optionally substituted with one or two groups =O or =S, $R_{11}$ represents a hydrogen atom, a ($C_1$-$C_8$) alkyl group or a —$(CH_2)_5$—$NH_2$ group, $R_{15}$ and $R_{16}$ independently represent a hydrogen atom, a ($C_1$-$C_8$)alkyl group or a ($C_6$-$C_{10}$)aryl group, n is equal to 2, 3, 4, or 5, m is equal to 2, 3, 4, or 5, o is equal to 2, 3, or 4 and s is equal to 1, 2, 3, or 4, t is equal to 0, 1, 2 or 3, and also the stereoisomers, mixtures of stereoisomers, and/or pharmaceutically acceptable salts thereof.

15. A process for preparing a compound of formula (I) as defined in claim 1, comprising a step of reductive amination of the compound of formula (II)

in which $R_{15}$ and $R_{16}$, independently represent a hydrogen atom, a ($C_1$-$C_8$)alkyl group or a ($C_6$-$C_{10}$)aryl group, R1 and R2 independently represent a hydrogen atom, an $SO_3H$ group or a hydroxyl group, with an amine of formula $R'NH_2$ in which R' is as defined in claim 1, in the presence of a reducing agent which may be chosen from titanium tetraisopropoxide, zirconium tetraisopropoxide, $NaBH_3CN$, $NaBH_4$ or a mixture thereof, to obtain said compound of formula (I).

16. The pharmaceutical or veterinary composition according to claim 11, wherein the antibiotic is chosen from doxycycline or chloramphenicol, penicillin, ampicillin, amoxicillin, cloxacillin, dicloxacillin, oxacillin, nafcillin, cephalexin, cephapirin, cefazolin, ceftiofur, cefoperazone, cefovecin, cefquinome, thimaphenicol, florfenicol, terramycin, erythromycin, spiramycin, tylosin, josamycin, tilmicosin, tulathromycin, gamithromycin, tildipirosin, clindamycin, lincomycin, pirlimycin, tiamulin, valnemulin, oxolinic acid, flumequine, enrofloxacin, danofloxacin, ibafloxacin, marbofloxacin, difloxacin, obifloxacin, pradofloxacin, rifampicin, rifaximin, sulfamethizole, sulfathiazole, sulfadimidine, sulfamethoxazole, sulfadiazine, sulfadimethoxine, sulfamethoxypyridazine, trimethoprim, baquiloprim, metronidazole, dimetridazole, ronidazole, nitrofurantoin, furazolidone and furaltadone.

\* \* \* \* \*